United States Patent
Xie et al.

(10) Patent No.: US 12,275,790 B2
(45) Date of Patent: Apr. 15, 2025

(54) HUMANIZED ANTI-PD-1 ANTIBODY AND THE USE THEREOF

(71) Applicant: SinoCellTech Ltd., Beijing (CN)

(72) Inventors: Liangzhi Xie, Beijing (CN); Chunyun Sun, Beijing (CN); Juan Ma, Beijing (CN)

(73) Assignee: SinoCellTech Ltd., Beijing (CN)

( * ) Notice: Subject to any disclaimer, the term of this patent is extended or adjusted under 35 U.S.C. 154(b) by 769 days.

(21) Appl. No.: 17/353,617

(22) Filed: Jun. 21, 2021

(65) Prior Publication Data

US 2022/0002412 A1    Jan. 6, 2022

Related U.S. Application Data

(63) Continuation of application No. PCT/CN2019/126594, filed on Dec. 19, 2019.

(30) Foreign Application Priority Data

Dec. 21, 2018 (CN) .......................... 201811573605.4

(51) Int. Cl.
C07K 16/28 (2006.01)
A61K 39/00 (2006.01)
A61K 47/68 (2017.01)

(52) U.S. Cl.
CPC ...... *C07K 16/2818* (2013.01); *A61K 47/6849* (2017.08); *A61K 2039/505* (2013.01); *C07K 2317/24* (2013.01); *C07K 2317/567* (2013.01); *C07K 2317/76* (2013.01); *C07K 2317/92* (2013.01)

(58) Field of Classification Search
CPC ............ C07K 16/2818; C07K 2317/24; C07K 2317/567; C07K 2317/76; C07K 2317/92; C07K 2317/33; C07K 2317/732; C07K 2317/734; C07K 2317/74; C07K 2317/94; C07K 2317/21; C07K 2317/52; C07K 2317/56; C07K 2317/565; A61K 47/6803; A61K 47/6849; A61K 2039/505; A61K 45/06; A61K 39/39558; A61P 35/00
See application file for complete search history.

(56) References Cited

U.S. PATENT DOCUMENTS

2016/0376367 A1    12/2016    Yuan et al.

FOREIGN PATENT DOCUMENTS

| CN | 106103485 A | 11/2016 |
|---|---|---|
| CN | 106519034 A | 3/2017 |
| CN | 107207593 A | 9/2017 |
| CN | 107847574 A | 3/2018 |
| CN | 108289953 A | 7/2018 |
| CN | 108697791 A | 10/2018 |
| CN | 108840932 A | 11/2018 |
| JP | 2018-529359 A | 9/2016 |
| JP | 2017500889 A | 1/2017 |
| JP | 2017506067 A | 3/2017 |
| JP | 2018-503365 A | 2/2018 |
| JP | 2018-533973 A | 11/2018 |
| WO | 2015085847 A1 | 6/2015 |
| WO | 2015/112900 A1 | 7/2015 |
| WO | 2016/092419 A1 | 6/2016 |
| WO | 2017/019846 A1 | 2/2017 |
| WO | 2017/055547 A1 | 4/2017 |
| WO | 2017/058859 A1 | 4/2017 |
| WO | 2017/079112 A1 | 5/2017 |
| WO | 2017/087599 A1 | 5/2017 |
| WO | 2018/113258 A1 | 6/2018 |

OTHER PUBLICATIONS

Philips et al. Therapeutic uses of anti-PD-1 and anti-PD-L1 antibodies, International Immunology. 2015. 27 (1): 39-46, (Year: 2015).*
International Search Report and Written Opinion dated Mar. 17, 2020 in connection with International Application No. PCT/CN2019/126594, 27 pages.
Auwalin, Muhammad, Indonesian Office Action dated Oct. 3, 2022, 2 pages, Indonesian Patent Office, Jakarta Selatan 12910.
Examiner's Report, Canadian Patent Application No. 3,124,276, Aug. 10, 2022, 7 pages, Canadian Intellectual Property Office, Canada.
Horita, Shoichiro, High-resolution crystal structure of the therapeutic antibody pembrolizumab bound to the human PD-1, Scientific Reports, , Oct. 13, 20126,8 pages, G-35297, DOI:10.1038/srep35297.
Japanese Office Action, Patent Application No. 2021-536399, 7 pages, Japan.
Korean Notice of Preliminary Rejection, Patent No. 520210535719, Apr. 5, 2024, 12 Pages.
Korean Notice of Preliminary Rejection, Patent No. 520210535719, Apr. 5, 2024, 12 Pages (translation).
Lee, Ju Yeon, Structural basis of checkpoint blockade by monoclonal antibodies in cancer immunotherapy , Oct. 31, 2016, 10 pages, 7:13354 DOI:10.1038/ncomms13354, Nature Communications.
Lockard, Joan S. et al., Efficacy and Toxicity of the Solvent Polyethylene Glycol 400 in Monkey Model, Epilepsia, 20:77-84, 1979, Raven Press, New York, U.S.A.
Mariuzza, R.A., The Structural Basis of Antigen-Antibody Recognition, Annual Review Biophys. Chem. 1987. 16:139-159.

(Continued)

*Primary Examiner* — Brad Duffy
*Assistant Examiner* — Amber K Faust
(74) *Attorney, Agent, or Firm* — Smart & Biggar LP

(57) ABSTRACT

The present disclosure provides a recombinant humanized monoclonal antibody against programmed cell death receptor-1 (PD-1) or an antigen-binding fragment thereof, which can be used in tumor or cancer immunotherapy. The disclosure also provides nucleic acid sequences encoding said antibody or antigen-binding fragment thereof, vectors containing said nucleic acid sequences, pharmaceutical compositions and kits.

22 Claims, 21 Drawing Sheets

Specification includes a Sequence Listing.

(56) References Cited

OTHER PUBLICATIONS

Na, Zhenkun et al., Structural basis for blocking PD-1-mediated immune suppression by therapeutic antibody pembrolizumab, Cell Research, Jun. 21, 2016, 27:147-150, 2017.
Office Action, RU2021119613, Feb. 10, 2022, 5 Pages (Translation).
Office Action, RU2021119613, Feb. 10, 2022, 9 pages.
Pflug, Alexander, European Search Report, EP 19 89 8443, European Patent Office, Dec. 8, 2022, 9 pages, The Hague.
Russian Search Report, RU2021772, 2 pages.
Takeuchi, Yuki, Japanese Office Action, Patent Application No. 2021-536399, Jul. 11, 2022, 7 pages, Japanese Patent Office, Japan.
Van Broekhoven, Christina, Examination Report, Patent Application No. 2019409184, Sep. 1, 2023, 4 pages, IP Australia, Australia.
Yahaya, Hasnah binti, Substantive Examination Adverse Report, Feb. 24, 2023, 5 pages, Intellectual Property Corporation of Malaysia, Kuala Lumpur, Malaysia.
Yahaya, Hasnah binti, Substantive Examination Adverse Report, May 31, 2023, 5 pages, Intellectual Property Corporation of Malaysia, Selangor, Malaysia.

* cited by examiner

HUMANIZED ANTI-PD-1 ANTIBODY AND THE USE THEREOF

CROSS-REFERENCE SECTION

This application is a continuation of and claims priority to PCT Application No. PCT/CN2019/126594 filed Dec. 19, 2019, which itself claims priority to Chinese Patent Application No. 201811573605.4 filed Dec. 21, 2018. The contents from all of the above are hereby incorporated in their entirety by reference.

SEQUENCE LISTING

A replacement Sequence Listing in a file named REPLACEMENT Sequence Listing, created on Oct. 8, 2024, the REPLACEMENT Sequence Listing file having a size of 36,031 bytes replaces the Sequences in a file named Sequence Listing, created on Dec. 21, 2018, the file having a size of 36,864 bytes as submitted with the application on Jun. 21, 2021. All sequences in the latter file are hereby incorporated by reference.

TECHNICAL FIELD

The present disclosure relates to the field of oncology or cancer immunotherapy. Specifically, the present disclosure provides a recombinant humanized antibody against programmed cell death receptor-1 (PD-1), which can be used in tumor or cancer immunotherapy. The disclosure also provides nucleic acid sequences encoding said antibody, vectors containing said nucleic acid sequences, pharmaceutical compositions and kits.

BACKGROUND

PD-1 is a type I transmembrane glycoprotein consisting of 288 amino acids with a molecular weight of approximately 50 kDa and is a member of the CD28 family, also known as CD279. It functions as a regulator of programmed cell death and is expressed mainly on the surface of mature $CD4^+$ and $CD8^+$ T cells, but also on natural killer T cells, B cells, monocytes and some dendritic cells.

PD-1 has two ligands, PD-L1 (i.e. B7-H1, also known as CD274) and PD-L2 (i.e. B7-DC, also known as CD273), both of which are transmembrane protein molecules of the B7 family. In terms of amount and action, PD-L1 is the major PD-1 ligand. PD-L1 is widely expressed on the surface of various cell types, including haematopoietic cells such as dendritic cells, B cells and T cells, as well as non-haematopoietic cells such as epithelial and endothelial cells. The expression of PD-L1 on the surface of tumor cells shows high, which can be up-regulated by inflammatory cytokines such as IFN-γ and TNF-α. PD-L2 ligand has high similarity to PD-L1, but its distribution is relatively limited, mainly expressed on the surface of immune cells such as macrophages, dendritic cells and mast cells, and its expression is low. PD-L2 binds PD-1 with higher affinity, about three times that of PD-L1.

PD-1 plays its biological role by binding to its ligands, inhibiting T cell receptor-mediated T cell proliferation, activation and cytokine secretion, thereby suppressing the initial and effector phases of the immune response, maintaining immune stability and preventing the development of autoimmune diseases. When PD-1 binds to its ligand, the tyrosine residues within the immunoreceptor tyrosine-based switch motif (ITSM), one domain of PD-1 cytoplasmic region, is phosphorylated, then the phosphorylated ITSM recruits SHP-2 phosphatase, resulting inhibition of important downstream pathways through dephosphorylation such as the blockage of the activation of phosphoinositide 3-kinase (PI3K) and its downstream protein kinase B (PKB or Akt), the inhibition of glucose metabolism, the production of the cytokine interleukin-2 (IL-2) and the expression of the anti-apoptotic protein Bcl-xl; thus inhibits the proliferation and activation of T and B cells and the secretion of immunoglobulins, as a result, the autoimmune response is suppressed. Tumor cells take advantage of this immunosuppressive mechanism to achieve immune escape, via the binding of PD-L1 highly expressed there into PD-1 molecules on the surface of lymphocytes, they evades from being immune recognized and cleared by organism.

Monoclonal antibodies targeting PD-1 are currently a hot topic in tumor or cancer immunotherapy research. By blocking the binding of PD-1 to its ligand, these monoclonal antibodies can increase secretion of T cells and IFN-γ and IL-2 at tumor sites, reduce the proportion of Myeloid-derived suppressor cells (MDSCs), alter the tumor microenvironment, restore and enhance the immune killing function of T cells, and thus inhibit tumor growth. Currently, the US Food and Drug Administration (FDA) has approved the marketing authorization of PD-1 antibodies, including Bristol-Myers Squibb's Opdivo (generic Nivolumab) and Merck &Co's Keytruda (generic Pembrolizumab). Opdivo is approved for the treatment of melanoma, non-small cell lung cancer, head and neck squamous cell carcinoma, classic Hodgkin's lymphoma, urothelial carcinoma, high microsatellite instability carcinoma, advanced renal cell carcinoma and hepatocellular carcinoma; Keytruda is approved for the treatment of melanoma, non-small cell lung cancer, head and neck squamous cell carcinoma, classic Hodgkin's lymphoma, urothelial carcinoma, high microsatellite instability and gastric cancer. In addition, domestic and international PD-1 target antibodies in clinical research include Regeneron/Sanofi's REGN2810, Top Alliance's JS001, Hengrui's SHR-1210, Beigene's BGB-A317, Cinda's IBI308 and Gloria/WuXiPharmaTech's GLS-010, and many other anti-PD-1 and anti-PD-L1 antibody drugs in preclinical research.

In conclusion, research on monoclonal antibodies targeting PD-1 has made some progress. However, there is still a need for better efficacy, safety and competitive monoclonal biologics in oncology or cancer immunotherapy.

SUMMARY

The technical terms used in the present disclosure and their corresponding abbreviation are shown in Table 1.

TABLE 1

| Glossary of terms | |
|---|---|
| Term | Abbreviation |
| Dendritic cells | DCs |
| Interferon gamma | IFN-γ |
| Transforming growth factor alpha | TNF-α |
| Immunoreceptor tyrosine switch motifs | ITSM |
| Protein tyrosine phosphatase-2 containing the SH2 structural domain | SHP-2 |
| Phosphatidylinositol 3-kinase | PI3K |
| Protein kinase B | PKB |
| Interleukin-2 | IL-2 |
| Myeloid-derived suppressor cells | MDSC |
| Horseradish peroxidase | HRP |
| Complementary determining region | CDR |

TABLE 1-continued

Glossary of terms

| Term | Abbreviation |
| --- | --- |
| Fluorescein isothiocyanate | FITC |
| Antibody-dependent cell-mediated cytotoxicity | ADCC |
| Complement-dependent cytotoxicity | CDC |
| Human peripheral blood mononuclear cells | PBMC |
| Recombinant Human Interleukin-4 | rhIL-4 |
| Recombinant human granulocyte-macrophage colony-stimulating factor | rhGM-CSF |
| Fetal bovine serum | FBS |
| Bovine serum albumin | BSA |

A first aspect of the present disclosure provides an isolated PD-1 antibody or antigen-binding fragment thereof comprising a light chain variable region or a portion thereof and/or a heavy chain variable region or a portion thereof, wherein the light chain variable region or a portion thereof comprises a light chain CDR1 having an amino acid sequence of SEQ ID NO: 10, a light chain CDR2 having an amino acid sequence of SEQ ID NO: 11 and a light chain CDR3 having an amino acid sequence of SEQ ID NO: 12; and the heavy chain variable region or portion thereof comprises heavy chain CDR1 having amino acid sequence of SEQ ID NO: 13, heavy chain CDR2 having amino acid sequence of SEQ ID NO: 14 and heavy chain CDR3 having amino acid sequence of SEQ ID NO: 15.

In a specific embodiment, said PD-1 antibody or antigen-binding fragment thereof comprises, consists of, or consists essentially of: an amino acid sequence having at least 90%, 92%, 95%, 98% or 100% sequence identity to the PD-1 antibody light chain variable region sequence of SEQ ID NO:23 and an amino acid sequence having at least 90%, 92%, 95%, 98% or 100% sequence identity to the PD-1 antibody heavy chain variable region sequence of SEQ ID NO:22.

In a particular embodiment, said antibody further comprises a light chain constant region and a heavy chain constant region; in a particular embodiment, wherein said antibody further comprises a light chain constant region and a heavy chain constant region, preferably said light chain constant region has an amino acid sequence having at least 90%, 92%, 95%, 98% or 100% sequence identity to the kappa light chain constant region of amino acid sequence of SEQ ID NO:25, and/or said heavy chain constant region has an amino acid sequence having at least 90%, 92%, 95%, 98% or 100% sequence identity to the IgG4 heavy chain constant region of amino acid sequence of SEQ ID NO:24.

In a specific embodiment, said antibody is an IgG antibody. In one specific embodiment, said antibody is an IgG4 antibody.

In one specific embodiment, the antibody or antigen-binding fragment thereof is a monoclonal antibody or antigen-binding fragment thereof.

In a specific embodiment, the antibody or antigen-binding fragment thereof binds to the recombinant human PD-1 protein with an affinity KD average of about 10, 20, 30, 40, 50, 60, 70, 80, 90, 100, 110, 120, 130, 140, 150, 160, 170, 180, 190, 200 pM or higher, or any ranges with the foregoing values as endpoints, such as about 20-200 pM, or about 60-70 pM, etc., or any values therein, such as about 64.8 pM or about 108 pM, etc. The method for determining the binding affinity KD is as described in the examples of this application.

In one specific embodiment, the antibody or antigen-binding fragment thereof specifically binds to a PD-1 protein molecule comprising the amino acid sequence of SEQ ID NO:1 or to a protein molecule having an amino acid sequence having at least 90%, 92%, 95%, 98% or 100% sequence identity to SEQ ID NO:1.

A second aspect of the invention provides an isolated PD-1 antibody or antigen-binding fragment thereof that specifically binds to a peptide sequence selected from at least one of the PD-1 protein extracellular region 60SESFV64 (SEQ ID NO: 36), 78KLAAFPEDRSQP89 (SEQ ID NO: 37), 128LAPKAQI134 (SEQ ID NO: 38).

In a specific embodiment, there is provided an isolated antibody or antigen-binding fragment thereof that specifically binds to an amino acid residue selected from at least one of the extracellular regions E61, K78, D85, P130 of the PD-1 protein.

In one specific embodiment, the antigen-binding fragment is in the form of an Fv, Fab, Fab', Fab'-SH, F(ab')2, Fd fragment, Fd' fragment, single chain antibody molecule, or single domain antibody; in one specific embodiment, the single chain antibody molecule is a scFv, di-scFv, tri-scFv, diabody, or scFab.

In a further specific embodiment, the antibody or antigen-binding fragment thereof in the above embodiments forms a covalent or non-covalent conjugate or a recombinant multi-target fusion drug with another molecule, thereby to form a modified drug molecule, said another molecule being selected from a small molecule compound and/or a biomacromolecule.

In one embodiment, a modified drug molecule may include one of a small molecule and a biomacromolecule; and an isolated PD-1 antibody or antigen-binding fragment. The modified drug molecule may include one of a covalent conjugate, a non-covalent conjugate, and a recombinant multi-target fusion drug.

The present disclosure relates to a pharmaceutical composition including an isolated PD-1 antibody or antigen-binding fragment thereof and a modified drug molecule comprising: one of a small molecule and a biomacromolecule, where the modified drug molecule includes one of a covalent conjugate, a non-covalent conjugate, and a recombinant multi-target fusion drug. The pharmaceutical composition may be a therapeutic agent.

A third aspect of the disclosure provides an isolated nucleic acid whose nucleotide sequence encodes the antibody and/or antigen binding fragment of the first and second aspects.

A fourth aspect of the present disclosure provides a vector comprising the nucleic acid of the third aspect.

A fifth aspect of the disclosure provides an isolated cell expressing the antibody and/or antigen-binding fragment of the first and second aspects, and/or comprising the nucleic acid of the third aspect or the vector of the fourth aspect.

In one specific embodiment, said cells are prokaryotic or eukaryotic cells.

A sixth aspect of the present disclosure provides a method for producing the antibody and/or antigen-binding fragment of the first and second aspects, said method comprising culturing the cells of the fifth aspect and purifying said antibodies.

A seventh aspect of the present disclosure provides the use of the antibody and/or antigen-binding fragment and/or modified drug molecule of the first and second aspects for the preparation of medicines for the treatment of tumor or cancer.

In one specific embodiment, said tumor or cancer is colon cancer.

An eighth aspect of the present disclosure provides the use of the antibody and/or antigen-binding fragment and/or modified drug molecule of the first aspect for the treatment of tumor or cancer.

In one specific embodiment, said tumor or cancer is colon cancer.

A ninth aspect of the disclosure provides a pharmaceutical composition comprising the antibody and/or antigen-binding fragment and/or modified drug molecule of the first and second aspects.

A tenth aspect of the present disclosure provides a pharmaceutical combination comprising the pharmaceutical composition of the ninth aspect and one or more therapeutically active compounds.

An eleventh aspect of the present disclosure provides a kit comprising the antibody and/or antigen-binding fragment and/or modified drug molecule of the first and second aspects, or the pharmaceutical composition of the ninth aspect or the pharmaceutical combination of the tenth aspect, preferably further comprising a device for administration.

A twelfth aspect of the present disclosure provides a method of treating a tumor or cancer comprising administering to a subject in need thereof a therapeutically effective amount of the isolated PD-1 antibody or antigen-binding fragment thereof or modified drug molecule of the first and second aspects, or the pharmaceutical composition of the ninth aspect, or a pharmaceutical combination of the tenth aspect, or the kit of the eleventh aspect, thereby treating said tumor or cancer, preferably wherein said tumor or cancer is colon cancer.

DETAILED DESCRIPTION

Definition

Figure 1:
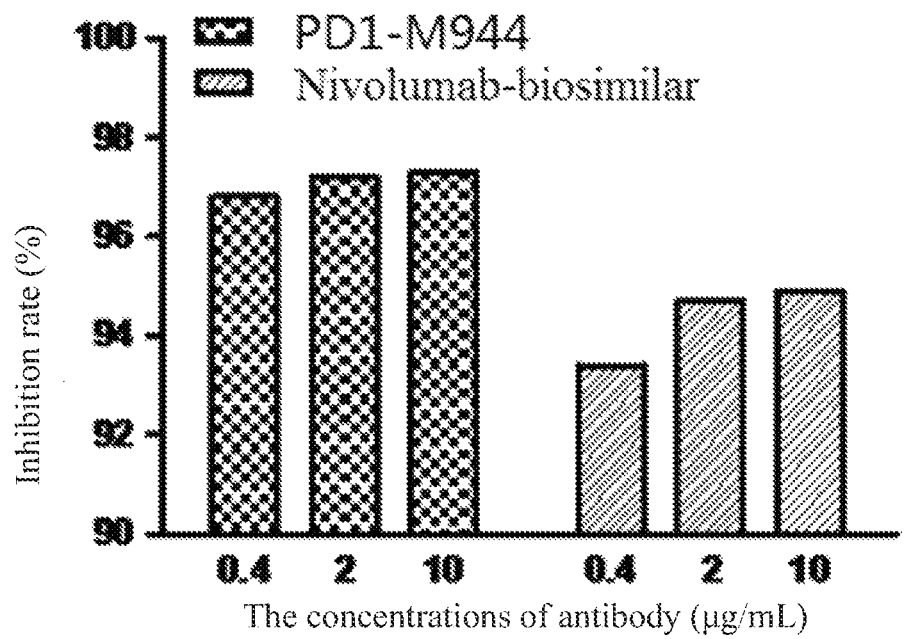
FIG. 1: The blocking of murine antibody PD1-M944 on the binding of PD-L1 (A) and PD-L2 (B) to PD-1 protein.
Figure 1:
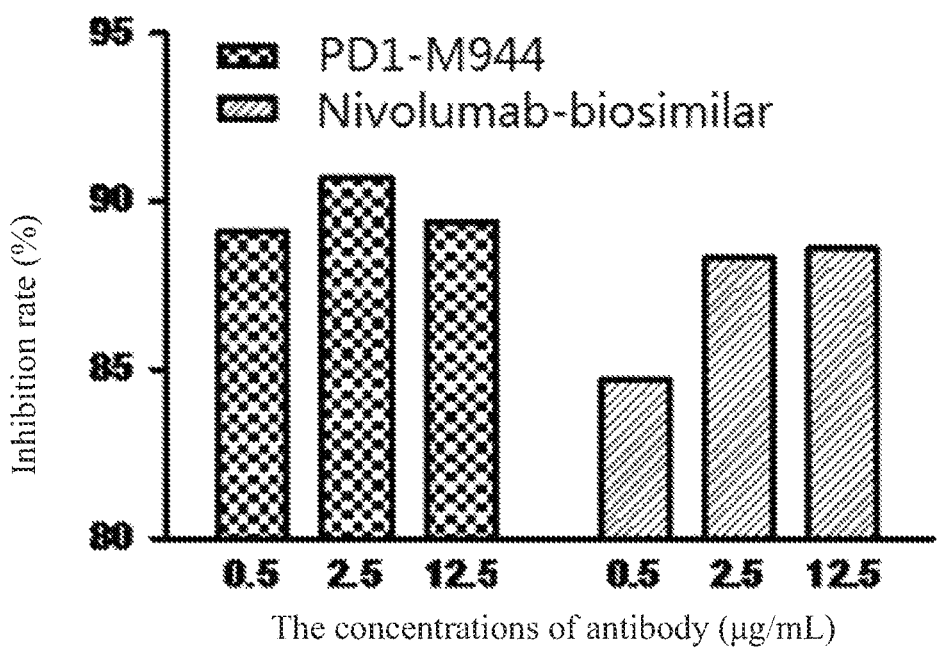

Unless otherwise stated, all technical and scientific terms used herein have the meaning normally understood by a person skilled in the art to which the present disclosure belongs. For the purposes of the present disclosure, the following terms are further defined.

When used herein and in the appended claims, the singular forms "one", "a/an", "another" and "said" include the plural designation of the object unless the context clearly indicates otherwise.

The term "antibody" refers to an immunoglobulin molecule and refers to any form of antibody that exhibits the desired biological activity. These include, but are not limited to, monoclonal antibodies (including full-length monoclonal antibodies), polyclonal antibodies and multispecific antibodies (e.g. bispecific antibodies), and even antibody fragments. Typically, full-length antibody structures preferably comprise four polypeptide chains, two heavy (H) chains and two light (L) chains, typically interconnected by disulfide bonds. Each heavy chain contains a heavy chain variable region and a heavy chain constant region. Each light chain contains a light chain variable region and a light chain constant region. In addition to this typical full-length antibody structure, the structure also includes other derivative forms.

The term "variable region" refers to the domain in the heavy or light chain of an antibody that is involved in the binding of the antibody to the antigen. The variable regions of the heavy and light chains of natural antibodies (VH and VL, respectively) generally have a similar structure and can be further subdivided into highly variable regions (called complementary decision regions (CDRs)) interspersed with more conserved regions (called framework regions (FRs)).

The term 'complementary determining region' (CDR, e.g. CDR1, CDR2 and CDR3) refers to such amino acid residues in the variable region of an antibody whose presence is necessary for antigen binding. Each variable region typically has three CDR regions identified as CDR1, CDR2 and CDR3. Each complementary determining region may contain amino acid residues from a "complementary determining region" as defined by Kabat (Kabat et al., Sequences of Proteins of Immunological Interest, 5th Ed. Public Health Service, National Institutes of Health, Bethesda, MD 1991) and/or those residues from the "high-variable loop" (Chothia and Lesk; J MolBiol 196: 901-917 (1987)).

The term "framework" or "FR" residues are those residues within the variable region other than CDR residues as defined herein.

Each heavy chain variable region and light chain variable region typically contains 3 CDRs and up to 4 FRs, said CDRs and FRs being arranged from the amino terminus to the carboxyl terminus in the following order, for example: FR1, CDR1, FR2, CDR2, FR3, CDR3, and FR4.

The complementary determining region (CDR) and the framework region (FR) of a given antibody can be identified using the Kabat system (Kabat et al: Sequences of Proteins of Immunological Interest, 5th edition, US Department of Health and Human Services, PHS, NIH, NIH Publication No. 91-3242, 1991).

The term "constant region" refers to such amino acid sequences in the light and heavy chains of an antibody that are not directly involved in the binding of the antibody to the antigen but exhibit a variety of effector functions such as antibody-dependent cytotoxicity.

According to the amino acid sequence of the constant region of their heavy chains, intact antibodies can be classified into five classes of intact antibodies: IgA, IgD, IgE, IgG and IgM, of which IgG and IgA can be further divided into subclasses (isoforms), such as IgG1, IgG2, IgG3, IgG4, IgA1 and IgA2. Accordingly, the heavy chains of the five classes of antibodies are classified into $\alpha$, $\delta$, $\epsilon$, $\gamma$ and $\mu$ chains, respectively. The light chains of the antibodies are classified into $\kappa$ and $\lambda$ according to the amino acid sequence of their light chain constant region. The light chains of the antibodies are classified into $\kappa$ and $\lambda$ according to the amino acid sequence of their light chain constant region.

An "antigen-binding fragment of an antibody" comprises a portion of an intact antibody molecule that retains at least some of the binding specificity of the parent antibody and typically includes at least a portion of the antigen-binding region or variable region (e.g. one or more CDRs) of the parent antibody. Examples of antigen-binding fragments include, but are not limited to, Fv, Fab, Fab', Fab'-SH, F(ab')2, Fd fragments, Fd' fragments, single chain antibody molecules (e.g. scFv, di-scFv or tri-scFv, diabody or scFab), single domain antibodies.

An "antibody fragment" is a non-intact antibody molecule that retains at least some of the biological properties of the parent antibody, including, but not limited to, an Fc fragment, in addition to those described above as "antigen-binding fragments".

The term "modified drug molecule" means a conjugate or a recombinant multi-target fusion drug formed by covalent or non-covalent connecting an antibody or fragment thereof, such as an antigen-binding fragment to another molecule which is a small molecule compound or biomacromolecule.

The term "chimeric" antibodies refer to antibodies in which a portion of the heavy and/or light chain is derived from a specific source or species and the remainder is derived from a different source or species. "Humanized antibodies" are a subset of "chimeric antibodies".

The term "humanized antibody" or "humanized antigen-binding fragment" is defined herein as an antibody or antibody fragment that is: (i) derived from a non-human source (e.g., a transgenic mouse carrying a heterologous immune system) and based on a human germline sequence; or (ii) a chimeric antibody where the variable region is of non-human origin and the constant region is of human origin; or (iii) a CDR transplant where the CDR of the variable region is of non-human origin and one or more frame work regions of the variable region are of human origin and the constant region, if any, is of human origin. The aim of "Humanization" is to eliminate the immunogenicity of antibodies of non-human origin in the human body, while retaining the greatest possible affinity. It is advantageous to select the human framework sequence that is most similar to the framework sequence of the non-human source antibody as the template for humanization. In some cases, it may be necessary to replace one or more amino acids in the human framework sequence with corresponding residues in the non-human construct to avoid loss of affinity.

The term "monoclonal antibody" refers to an antibody derived from a substantially homogeneous population of antibodies, i.e. every single antibody comprised in the population is identical except for possible mutations (e.g. natural mutations) which may be present in very small quantities. The term "monoclonal" therefore indicates the nature of the antibody in question, i.e. not a mixture of unrelated antibodies. In contrast to polyclonal antibody preparations, which usually comprise different antibodies against different epitopes, each monoclonal antibody in a monoclonal antibody preparation is directed against a single epitope on the antigen. In addition to their specificity, monoclonal antibody preparations have the advantage that they are usually not contaminated by other antibodies. The term "monoclonal" should not be understood as requiring the production of said antibodies by any particular method. The term monoclonal antibody specifically includes chimeric antibodies, humanized antibodies and human antibodies.

The antibody "specifically binds" to a target antigen such as a tumor-associated peptide antigen target (in this case, PD-1), i.e. binds said antigen with sufficient affinity to enable said antibody to be used as a therapeutic agent, targeting a cell or tissue expressing said antigen, and does not significantly cross-react with other proteins, or does not significantly cross-react with proteins other than the homologues and variants of the target proteins mentioned above (e.g. mutant forms, splice variants, or protein hydrolysis truncated forms).

The term "binding affinity" refers to the strength of the sum of the non-covalent interactions between a molecule's individual binding sites and its binding partners. Unless otherwise stated, "binding affinity", when used herein, refers to the intrinsic binding affinity, which reflects a 1:1 interaction between members of a binding pair (e.g. antibody and antigen). "KD", "binding rate constant $k_{on}$" and "dissociation rate constant $k_{off}$" are commonly used to describe the affinity between a molecule (e.g. an antibody) and its binding partner (e.g. an antigen). Affinity, i.e. the tight degree at which a ligand binds a particular protein. Binding affinity is influenced by non-covalent intermolecular interactions such as hydrogen bonding, electrostatic interactions, hydrophobic and van der Waals forces between two molecules. In addition, the binding affinity between a ligand and its target molecule may be influenced by the presence of other molecules. Affinity can be analyzed by conventional methods known in the art, including the ELISA described herein.

The term "epitope" includes any protein determinant cluster that specifically binds to an antibody or T-cell receptor. Epitope determinant clusters typically consist of a molecule's chemically active surface groups (e.g. amino acid or sugar side chains, or a combination thereof) and often have specific three-dimensional structural features as well as specific charge characteristics.

An "isolated" antibody is an antibody that has been identified and isolated from a cell that naturally expresses the antibody. Isolated antibodies include in situ antibodies in recombinant cells and antibodies that are typically prepared by at least one purification step.

"Sequence identity" between two polypeptide or nucleic acid sequences indicates the number of residues that are identical between said sequences as a percentage of the total number of residues. When calculating the percentage identity, the sequences being aligned are matched in such a way as to produce a maximum match between the sequences, with the gaps in the match (if present) being resolved by a specific algorithm. Preferred computer program methods for determining identity between two sequences include, but are not limited to, GCG program packages including GAP, BLASTP, BLASTN and FASTA (Altschul et al., 1990, J. Mol. Biol. 215: 403-410). The above procedures are publicly available from the International Center for Biotechnology Information (NCBI) and other sources. The well-known Smith Waterman algorithm can also be used to determine identity.

The term "Fc receptor" or "FcR" refers to a receptor that binds to the Fc region of an antibody. Human FcRs of natural sequence are preferred, and preferably receptors that bind to IgG antibodies (gamma receptors), which include the FcγRI, FcγRII and FcγRIII isoforms, as well as variants of these receptors. All other FcRs are included in the term "FcR". The term also includes the neonatal receptor (FcRn), which is responsible for the transport of maternal IgG to the fetus (Guyer et al, Journal of Immunology 117: 587 (1976) and Kim et al, Journal of Immunology 24: 249 (1994)).

The term "neonatal Fc receptor", abbreviated as "FcRn", binds to the Fc region of IgG antibodies. The neonatal Fc receptor (FcRn) plays an important role in the metabolic fate of IgG-like antibodies in vivo. FcRn functions to rescue IgG from the lysosomal degradation pathway, thereby reducing its clearance in serum and lengthening its half-life. Therefore, the in vitro FcRn binding properties/characteristics of IgG are indicative of its in vivo pharmacokinetic properties in the circulation.

The term "effector function" refers to those biological activities attributable to the Fc region of an antibody, which vary from isotype to isotype. Examples of antibody effector functions include C1q binding and complement-dependent cytotoxicity (CDC), Fc receptor binding, antibody-dependent cell-mediated cytotoxicity (ADCC), antibody-dependent cellular phagocytosis (ADCP), cytokine secretion, immune complex-mediated uptake of antigen by antigen-presenting cells, cell surface receptors down-regulation (e.g. B-cell receptors) and B-cell activation.

The term "effector cell" refers to a leukocyte that expresses one or more FcR and performs effector functions. In one aspect, said effector cells express at least FcγRIII and perform ADCC effector functions. Examples of human leukocytes that mediate ADCC include peripheral blood mononuclear cells (PBMCs), natural killer (NK) cells, monocytes, cytotoxic T cells and neutrophils. Effector cells can be isolated from natural sources, for example, blood. Effector cells are usually lymphocytes associated with effector phase and function to produce cytokines (helper T cells), kill cells infected by pathogens (cytotoxic T cells) or secrete antibodies (differentiated B cells).

"Immune cells" include cells that have a haematopoietic origin and play a role in the immune response. Immune cells include: lymphocytes, such as B cells and T cells; natural killer cells; and myeloid cells, such as monocytes, macrophages, eosinophils, mast cells, basophils and granulocytes.

"Antibody-dependent cell-mediated cytotoxicity" or "ADCC" refers to a form of cytotoxicity in which secreted Ig binds to Fcγ receptors presented on certain cytotoxic cells (e.g. NK cells, neutrophils and macrophages) allows these cytotoxic effector cells to specifically bind to target cells bearing antigens and subsequently kill said target cells using, for example, a cytotoxin. To assess the ADCC activity of the target antibody, in vitro ADCC assays can be performed, such as the in vitro ADCC assays documented in U.S. Pat. No. 5,500,362 or 5,821,337 or U.S. Pat. No. 6,737,056 (Presta), the methods documented in embodiments of the present application. Useful effector cells for use in such assays include PBMCs and NK cells.

"Complement-dependent cytotoxicity" or "CDC" refers to the lysis of target cells in the presence of complement. Activation of the classical complement pathway is initiated by the binding of the first component of the complement system (C1q) to an antibody (of the appropriate subclass), in which the antibody binds to its corresponding antigen. To assess complement activation, a CDC assay can be performed, such as the CDC assay recited in Gazzano-Santoro et al., J. Immunol Methods 202: 163 (1996), for example the method documented in embodiments of the present application, for example in U.S. Pat. No. 6,194,551 B1 and WO1999/51642, wherein polypeptide variants having altered amino acid sequences of the Fc region (polypeptides having a variant Fc region) and polypeptide variants having enhanced or reduced C1q binding are described.

Amino Acid Sequence and Nucleotide Sequence of the Antibody of the Disclosure

The present disclosure used recombinant human PD-1 protein to immunize mice, and then obtained a M944 scFv antibody clone that specifically binds to recombinant human PD-1 with a high affinity by phage antibody library screening. The nucleotide sequences encoding the heavy and light chain variable regions of the M944 scFv antibody were then assemble by PCR with those encoding the mouse IgG1 heavy chain constant region and the mouse kappa light chain constant region, respectively, and the resulting assembled sequence were inserted into the transient expression vector HEK-293 cultured for expression. The high purity murine antibody PD1-M944 was purified using a protein A purification column. ELISA showed that the murine antibody PD1-M944 was able to block the binding of PD-1 to its ligand.

Then, using the classical method for humanized CDR transplantation, the human antibody light chain or heavy chain variable region closest to the murine light chain or heavy chain variable region was elected as the template. In an embodiment, IGKV3-11*01 is elected to be the humanization temple of light chain variable region, while IGHV3-21*02, heavy chain variable region. The humanized light chain variable region (VL) and heavy chain variable region (VH) sequences were obtained by inserting each of the three CDRs of the murine antibody light chain/heavy chain into the corresponding positions of the above human templates. As the key site of the murine framework region is essential to support the activity of the CDR, the key site was reverse mutated to the sequence of the murine antibody. The amino acid sequence and nucleotide sequence of the humanized antibody PD1-H944 were obtained by sequentially splicing the light chain/heavy chain signal peptide sequence, the sequence of the variable region of the light chain/heavy chain of the reverse mutated humanized antibody, and the sequence of the human IgG4 heavy chain constant region/ human kappa light chain constant region, respectively.

Nucleic Acids of the Present Disclosure

The present disclosure also relates to nucleic acid molecules encoding antibodies or portions thereof of the present disclosure. The sequences of these nucleic acid molecules include, but are not limited to, SEQ ID NO: 3-7 and 26-33.

The nucleic acid molecules of the present disclosure are not limited to the sequences disclosed herein, but also include variants thereof. Variants in the present disclosure may be described with reference to their physical properties in hybridization. It will be recognized by those of skill in the art that using nucleic acid hybridization techniques, nucleic acids can be used to identify their complements as well as their equivalents or homologues. It will also be recognized that hybridization can occur at less than 100% complementarity. However, given the appropriate choice of conditions, hybridization techniques can be used to distinguish said DNA sequences based on the structural relevance of the DNA sequence to a particular probe. For guidance on such conditions see Sambrook et al., Molecular Cloning: A Laboratory Manual, 2nd Ed. Cold Spring Harbor Press, Cold Spring Harbor, N. Y, 1989 and Ausubel, F. M., Brent, R., Kingston, R. E., Moore, D. D., Sedman, J. G., Smith, J. A., &Struhl, K. eds. (1995). Current Protocols in Molecular Biology. New York: John Wiley and Sons.

Recombinant Vectors and Expression

The present disclosure also provides recombinant constructs comprising one or more nucleotide sequences of the present disclosure. The recombinant constructs of the disclosure can be used with vectors, said vectors, for example, being plasmid, phagemid, phage or viral vectors, and the nucleic acid molecules encoding the antibodies of the disclosure are inserted into said vectors.

The antibodies provided herein can be prepared by recombinantly expressing nucleotide sequences encoding light and heavy chains or portions thereof in a host cell. In order to recombinantly express the antibody, the host cell may be transfected with one or more recombinant expression vectors carrying nucleotide sequences encoding the light and/or heavy chains or portions thereof, so that said light and heavy chains are expressed in said host cell. Standard recombinant DNA methodologies are used to prepare and/or obtain nucleic acids encoding heavy and light chains, to incorporate these nucleic acids into recombinant expression vectors and to introduce said vectors into host cells, e.g. Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and those documented in U.S. Pat. No. 4,816,397 by Boss et al.

Furthermore, a nucleotide sequence encoding a variable region of said heavy and/or light chain may be converted into a nucleotide sequence encoding, for example, a full-length antibody chain, a Fab fragment or a ScFv: for example, a DNA fragment encoding a variable region of the light chain or a variable region of the heavy chain may be operably ligated (so that the amino acid sequences encoded by both said DNA fragments are in frame) to another DNA fragment encoding, for example, an antibody constant region or a flexible linker. The sequences of the human heavy and light chain constant regions are known in the art (see, for example, Kabat, E. A., el al. (1991) Sequences of Proteins of Immunological Interest, Fifth Edition, U.S. Department of Health and Human Services, NIH Publication No. 91-3242), and DNA fragments including these regions can be obtained by standard PCR amplification.

To express the antibodies, standard recombinant DNA expression methods can be used (see, for example, Goeddel; Gene Expression Technology. Methods in Enzymology 185, Academic Press, San Diego, Calif. (1990)). For example, a nucleotide sequence encoding the desired antibody can be inserted into an expression vector, which is subsequently transfected into a suitable host cell. Suitable host cells are prokaryotic and eukaryotic cells. Examples of prokaryotic host cells are bacteria and examples of eukaryotic host cells are yeast, insect or mammalian cells. It should be understood that the design of an expression vector including the selection of a regulatory sequence is determined by a number of factors, such as the choice of host cell, the level of expression of the desired protein and whether the expression is constitutive or inducible.

Bacterial Expression

By inserting a structural DNA sequence encoding the desired antibody together with appropriate translation initiation and termination signals and the functional promoters into an operable reading frame, an available expression vector for use in bacteria is constructed. The vector will contain one or more phenotypic selection markers and an origin of replication to ensure the maintenance of the vector and provide amplification in the host as needed. Suitable prokaryotic hosts for transformation include multiple species of *E. coli, Bacillus subtilis, Salmonella typhimurium*, as well as *Pseudomonas, Streptomyces* and *Staphylococcus*.

The bacterial vector may be, for example, phage-, plasmid- or phagemid-based. These vectors may contain selectable markers and bacterial replication origins, which are derived from commercially available plasmids that usually contain elements of the well-known cloning vector pBR322 (ATCC 37017). After transforming an appropriate host strain and growing the host strain to an appropriate cell density, the selected promoter is de-repressed/induced by an appropriate method (for example, temperature change or chemical induction), and the cells are cultured for an additional time. The cells are usually harvested by centrifugation, disrupted by physical or chemical methods, and the resulting crude extract is retained for further purification.

In a bacterial system, a variety of expression vectors can be advantageously selected according to the intended use of the expressed protein. For example, when a large number of such proteins are to be produced for antibody production or for peptide library screening, for example, a vector that directs high-level expression of a fusion protein product to be easily purified may be required.

Mammalian Expression and Purification

Preferred regulatory sequences for expression in mammalian host cells include viral elements that direct high-level protein expression in mammalian cells, such as promoters and/or enhancers derived from cytomegalovirus (CMV) (e.g., CMV promoter/enhancer), promoters and/or enhancers of simian virus 40 (SV40) (e.g. SV40 promoter/enhancer), promoters and/or enhancers of adenovirus (e.g. adenovirus major late promoter (AdMLP)) and promoters and/or enhancers of polyoma virus. For a further description of viral regulatory elements and their sequences, see, for example, U.S. Pat. No. 5,168,062 by Stinski, U.S. Pat. No. 4,510,245 by Bell et al., and U.S. Pat. No. 4,968,615 by Schaffner et al. The recombinant expression vector may also include an origin of replication and a selection marker (see, for example, U.S. Pat. Nos. 4,399,216, 4,634,665 and 5,179,017 by Axel et al). Suitable selection markers include genes that confer resistance to drugs such as G418, hygromycin, or methotrexate to host cells into which the vector has been introduced. For example, the dihydrofolate reductase (DHFR) gene confers resistance to methotrexate, while the neo gene confers resistance to G418.

The transfection of the expression vector into the host cell can be performed using standard techniques such as electroporation, calcium phosphate precipitation, and DEAE-dextran transfection.

Suitable mammalian host cells for expressing the antibodies provided herein include Chinese Hamster Ovary (CHO cells) [including dhfr-CHO cells, as described in Urlaub and Chasin, (1980) Proc. Natl. Acad. Sci. USA 77:4216-4220, DHFR selection markers are employed, as described in, for example, R. J. Kaufman and P. A. Sharp (1982) Mol. Biol. 159:601-621], NSO myeloma cells, COS cells, and SP2 cells.

The antibodies of the present disclosure can be recovered and purified from recombinant cell culture by well-known methods, said well-known methods include, but are not limited to, ammonium sulfate or ethanol precipitation, acid extraction, protein A affinity chromatography, protein G affinity chromatography, anion or cation exchange chromatography, cellulose phosphate chromatography, hydrophobic interaction chromatography, affinity chromatography, hydroxyapatite chromatography, and lectin chromatography. High performance liquid chromatography ("HPLC") can also be used for purification. See, for example, Colligan, Current Protocols in Immunology, or Current Protocols in Protein Science, John Wiley & Sons, NY, N.Y., (1997-2001), e.g., chapters 1, 4, 6, 8, 9, 10, each of which is incorporated herein by reference in its entirety.

The antibodies of the present disclosure include naturally purified products, products of chemical synthetic methods and products produced by recombinant techniques from prokaryotic and eukaryotic hosts, said eukaryotic hosts including, for example, yeast, higher plant, insect, and mammalian cells. The antibodies of the disclosure may be glycosylated or may be non-glycosylated. Such methods are documented in many standard laboratory manuals, e.g., Sambrook, above, sections 17.37-17.42; Ausubel, above, chapters 10, 12, 13, 16, 18 and 20.

Thus, embodiments of the disclosure can also be host cells comprising said vector or nucleic acid molecules, wherein said host cells may be higher eukaryotic host cells such as mammalian cells, lower eukaryotic host cells such as yeast cells, and may be prokaryotic cells such as bacterial cells.

Properties and Functions of the Antibodies of the Disclosure

Property and function analysis of said PD1-H944 antibody were performed. The analysis showed that the antibody of the present disclosure has the following advantages: (1) it is able to bind human PD-1 with high affinity and specificity and has a low dissociation rate, thus providing good anti-tumor efficacy; (2) it is able to block the binding of PD-L1 to PD-1 more completely than Nivolumab; (3) when compared with Nivolumab, it binds recombinant human PD-1 more sensitively and more specifically; comparably cross binds to recombinant monkey PD-1, while neither binds to murine PD-1; (4) it is capable of blocking the binding of recombinant human PD-1 to its ligands Pd-L1 and Pd-L2 effectively, (5) it is capable of effectively re-activating immunosuppressed T cells and activating the recombinant human PD-1 reporter cell system; (6) exhibits an excellent tumor-suppressive effect in MC38 colon cancer tumorbearing humanized PD-1 mouse model, far better than that of Nivolumab (Sino Biological, Inc.) and comparable to that of Pembrolizumab (Sino Biological, Inc.); (7) it exhibits both low ADCC and CDC activities, while its ADCC activity is lower than that of Nivolumab.

Uses

The antibodies of the present disclosure can be used to treat a variety of tumors or cancers or to prepare medicines for the treatment of a variety of tumors or cancers, specifically targeting to aberrantly expressed PD-1 receptors. Non-limiting examples of said tumors or cancers include colon cancer.

Pharmaceutical Compositions

Antibodies of the disclosure may be prepared with at least one other agent (e.g. a stabilizing compound) to form pharmaceutical compositions comprising an antibody of the disclosure and one or more pharmaceutically acceptable carriers, diluents or excipients.

Kits

The present disclosure also relates to pharmaceutical packages and kits comprising one or more containers, said containers containing the foregoing pharmaceutical compositions of the present disclosure. Associated with such containers may be specifications in the form prescribed by the governmental agency governing the manufacture, use or distribution of the drug or biological product, which reflect approval for human administration by the agency in which said product is manufactured, used or distributed.

Preparation and Storage

The pharmaceutical compositions of the present disclosure can be prepared in a manner known in the art, for example by conventional mixing, dissolution, granulation, pastille preparation, grinding, emulsification, encapsulation, embedding or lyophilization methods.

Having already prepared pharmaceutical compositions comprising compounds of the present disclosure formulated in an acceptable carrier, they may be placed in appropriate containers and labeled for the treatment of the condition indicated. Such labeling would include the amount, frequency and administration routes of the drug.

Combinations

The pharmaceutical compositions comprising the antibodies of the present disclosure described above are also combined with one or more other therapeutic agents, such as antineoplastic agents, wherein the resulting combination does not cause unacceptable adverse effects.

The following examples are used to illustrate the disclosure exemplarily and are not intended to limit the disclosure.

EXAMPLES

Example 1: Screening for Murine-Derived Antibodies Blocking PD-1 Binding to PD-L1/PD-L2 Using a Phage Antibody Display Library 1.1 Immunization of Mice Recombinant human PD-1 protein (Sino Biological, Inc, Cat. 10377-H08H) was used to immunize mice. The amino acid sequence of the extracellular region of this human PD-1 protein (UniProtKB Q15116) is Met1-Gln167 (SEQ ID NO: 1).

The recombinant human PD-1 protein was mixed with Freund's adjuvant and the mixture which administered subcutaneously at intervals of 2 weeks, 3 weeks, 2 weeks and 3 weeks was used for immunizing mice for 5 times at a dose of 20 μg each. From the second immunization onwards, blood was collected seven days after each immunization via the medial canthal plexus of the eye. The serum titer of mouse anti-PD-1 was measured by ELISA using coated recombinant human PD-1 protein. Serum titer reached 8000-fold dilution after fifth immunization, and the mice were boosted intravenously with 25 μg recombinant human PD-1 protein 9 weeks after the fifth immunization. 4 days later, the mice were executed and the spleen tissue was frozen in liquid nitrogen.

1.2 Phage—Display Library Screening

RNA was extracted from mouse spleen tissue using TriPure Isolation Reagent (Roche), and cDNA was obtained by reverse transcription using a reverse transcription kit (Invitrogen). The respective nucleotide sequences encoding the light and heavy chain variable regions of the murine antibody were amplified and assembled into the nucleotide sequence encoding the scFv thereof via the overlap extension PCR method, wherein the respective nucleotide sequences encoding the light and heavy chain variable regions were linked via a linker, TCTAGTGGTGGCGGTGGTTCGGGCGGTGGTG-GAGGTGGTAGTTCTA GATCTTCC(SEQ ID NO:2) (Ref: Rapid PCR-cloning of full-length mouse immunoglobulin variable regions; Cloning immunoglobulin variable domains for expression by the polymerase chain reaction T Joneset.al Bio/Technology 9(6):579, July 1991), then enzymatically ligated into the phage vector pComb3x (Sino Biological, Inc.) by restriction endonuclease Sfi I (Fermentas), and then electro transformed the competent X-Blue to construct a phage display scFv antibody library for immunized mice. By coating recombinant human PD-1 protein on ELISA plates, an anti-PD-1 positive antibody-enriched phage libraries was obtained following the process of phage antibody panning (Ref: Antibody Phage Display: Methods and Protocols, Philippa M. O'Brien and Robert Aitken (Eds), Humana Press, ISBN: 9780896037113).

Monoclonal phages were selected from the enriched library, expressed, and then tested their binding to recombinant human PD-1 protein by ELISA. A clone of the highly binding antibody M944 scFv specifically binding to recombinant human PD-1 was elected and commissioned a sequencing company to sequence the nucleotide sequence of the M944 scFv antibody (SEQ ID NO:3).

1.3 Production of Murine Antibody PD1-M944

The nucleotide sequences of the heavy and light chain variable regions of the M944 scFv antibody (SEQ ID NO: 4/5) were assembled with the nucleotide sequences of the mouse IgG1 heavy chain constant region (SEQ ID NO: 6) and the mouse kappa light chain constant region (SEQ ID NO: 7), respectively, by PCR. The resulting nucleotide sequences were then enzymatically cut by Hind III and Xba I (Fermentas) and inserted into the transient expression vector pSTEP2 (Sino Biological, Inc), and the plasmids were extracted and transfected into HEK-293 cells for 7 days. The culture supernatant was purified with Protein A column for high purity antibody.

1.4 Murine Antibody PD1-M944 Functional Assay (1) Blocking the Binding of Recombinant Human PD-1 to PD-L1:

Recombinant human PD-1 protein at a concentration of 1 μg/mL was coated on a 96-well plate at 100 μL per well overnight at 4° C. The plates were washed the next day and blocked at room temperature for 1 h. 100 μL of 10 μg/mL of biotinylated protein PD-L1-Fc-biotin (SinoBiological, Inc.) was co-incubated with different concentrations (0.4 μg/mL, 2 μg/mL and 10 μg/mL) of PD1-M944 or Nivolumab (Sino Biological, Inc). The plates were washed to remove unbound antibodies. The plates were incubated with antibiotic streptavidin/HRP (Beijing Zhong Shan-Golden Bridge Biological Technology Co., Ltd) and then repeatedly washed, and the substrate chromogenic solution was added for color development. OD450 was detected after termination. The results showed that the recombinant PD-L1 protein could effectively bind to the coated PD-1 protein, and the binding of recombinant PD-L1 protein to PD-1 was effectively inhibited by the addition of different concentrations of PD1-M944 or Nivolumab (FIG. 1A). This result indicates that the murine antibody PD1-M944 has a good function of blocking the binding of PD-1 to its ligand PD-L1.

(2) Blocking the Binding of Recombinant Human PD-1 to PD-L2:

Recombinant human PD-1 protein at a concentration of 1 μg/mL was coated on a 96-well plate at 100 μL per well, overnight at 4° C., overnight, washed the next day and blocked at room temperature for 1 h. 100 μL of 0.5 μg/mL of biotinylated protein PD-L2-Fc-biotin (Sino Biological, Inc.) was co-incubated with different concentrations (0.5 μg/mL, 2.5 μg/mL and 12.5 μg/mL) of PD1-M944 or Nivolumab (Sino Biological, Inc.). The plates were washed to remove unbound antibodies, incubated with antibiotic streptavidin/HRP (Beijing Zhong Shan-Golden Bridge Biological Technology Co., Ltd), repeatedly washed, and the substrate chromogenic solution was added for color development, and OD450 was detected after termination. The results showed that the recombinant PD-L2 protein could effectively bind to the coated PD-1 protein, and the binding of recombinant PD-L2 protein to PD-1 was effectively inhibited by the addition of different concentrations of PD1-M944 or Nivolumab (FIG. 1B). This result indicates that the murine antibody PD1-M944 has a good function of blocking the binding of PD-1 to its ligand PD-L2.

Example 2: Humanization of the Sequence of the Murine Antibody PD1-M944 to Produce the Sequence of the Humanized Antibody PD1-H944

2.1 Determination of the 3 CDRs for Each of the Light and Heavy Chains of the Murine Antibody PD1-M944

The nucleotide sequence of the M944 scFv antibody was determined in Example 1.2, from which the amino acid sequences of the heavy and light chain variable regions of the PD1-M944 scFv antibody were deduced, see SEQ ID NOs: 8/9.

The amino acid sequences of the 3 CDRs of each of the light and heavy chains of the murine antibody PD1-M944 were determined reference to the Kabat numbering scheme, see Table 1. The 3 CDRs of each of the aforementioned light and heavy chains were transposed and retained in the final humanized antibody PD1-H944 in the subsequent steps, see Examples 2.2 and 2.3.

TABLE 1

PD1-M944/PD1-H944 light chain and heavy chain CDR sequences

| Name | Sequences |
|---|---|
| LCDR1 | ESVDSYGNSFMH (SEQ ID NO: 10) |
| LCDR2 | AASNQGSGVPA (SEQ ID NO: 11) |
| LCDR3 | QQSKEVPWT (SEQ ID NO: 12) |
| HCDR1 | GFTFSSYGMS (SEQ ID NO: 13) |
| HCDR2 | VATISGGGRDTYYSDSVKG (SEQ ID NO: 14) |
| HCDR3 | SRQYGTVWFFN (SEQ ID NO: 15) |

2.2 Humanized CDR Transplantation of Murine Antibody PD1-M944

The humanization of the murine antibody was performed using the classical humanization method of CDR transplantation. The human antibody light or heavy chain variable region, which is closest to the mouse light or heavy chain variable region, was elected as the template, and three CDRs (Table 1) from each of the mouse light or heavy chain were inserted into the variable region of the human antibody to obtain the humanized light chain variable region (VL) and heavy chain variable region (VH) sequences. The human template for the light chain variable region of PD1-M944 is IGKV3-11*01, which is 73.48% homologous to the light chain of PD1-M944, and the human template for the heavy chain variable region is IGHV3-21*02, which is 81.94% homologous to the heavy chain of PD1-M944.

2.3 Framework Region Reverse-Mutation of the Humanized Variable Region Sequence

As key sites in the murine-derived framework region are essential to support CDR activity, the corresponding sites were reversely mutated to those shown in the sequence of the murine antibody, wherein the position 89 in the light chain was reversely mutated to M and position 91 to F, in the heavy chain, the position 44 to R and the position 78 to N.

The humanized antibody PD1-H944 was obtained by CDR humanized transplantation and framework region reverse-mutation, and its heavy and light chain amino acid sequences are shown in SEQ ID NO:16/17, respectively; its heavy and light chain amino acid sequences in the form containing the signal peptide are shown in SEQ ID NO:18/19, respectively, comprising sequentially linked heavy/light chain signal peptide sequences (SEQ ID NO:20/21); the variable region of the heavy chain/light chain of humanized antibody sequence (SEQ ID NO:22/23); and the sequence of the constant region of humanized antibody which is the human IgG4 heavy chain constant region/human kappa light chain constant region respectively (SEQ ID NOs:24/25).

TABLE 2

Amino acid sequences and nucleotide sequences of murine-derived and humanized antibodies

| NOs | Name | Sequences |
|---|---|---|
| SEQ ID NO: 1 | Amino acid sequence Met 1-Gln167 of the extracellular region of human PD-1 protein (UniProtKB Q15116) | MQIPQAPWPVVWAVLQLGWRPGW FLDSPDRPWNPPTFSPALLVVTEGDNAT FTCSFSNTSESFVLNWYRMSPSNQTDK LAAFPEDRSQPGQDCRFRVTQLPNGRD FHMSVVRARRNDSGTYLCGAISLAPKA QIKESLRAELRVTERRAEVPTAHPSPSP RPAGQFQ |
| SEQ ID NO: 2 | Linker nucleotide sequence of the murine antibody scFv used in the construction of the phage antibody library | TCTAGTGGTGGCGGTGGTTCGGGC GGTGGTGGAGGTGGTAGTTCTAGATC TTCC |
| SEQ ID NO: 3 | Nucleotide sequence of murine antibody PD1-M944 scFv | Nucleotide sequence of light chain variable region of PD1-M944 (SEQ ID NO: 5): GATATTGTGCTAACTCAATCTCCA GCTTCTTTGGCTGTGTCTCTAGGGCA GAGGGCCACCATATCCTGCAGAGCCA GTGAAAGTGTTGATAGTTATGGCAATA GTTTTATGCACTGGTACCAGCAGAAA CCAGGACAGCCACCCAAACTCCTCAT CTATGCTGCATCCAACCAAGGATCCG GGGTCCCTGCCAGGTTTAGTGGCAGT GGGTCTGGGACAGACTTCAGCCTCAA CATCCATCCTATGGAGGAGGATGATAC |

TABLE 2-continued

Amino acid sequences and nucleotide sequences of murine-derived and humanized antibodies

| NOs | Name | Sequences |
|---|---|---|
| | | TGCAATGTATTTCTGTCAGCAAAGTAA<br>GGAGGTTCCGTGGACGTTCGGTGGAG<br>GCACCAAGCTGGAAATCAAA<br>Linker (SEQ ID NO: 2)<br>TCTAGTGGTGGCGGTGGTTCGGGCGGTGGT<br>GGAGGTGGTAGTTCTAGATCTTCC<br>Nucleotide sequence of heavy chain<br>variable region of PD1-M944<br>(SEQ ID NO: 4):<br>GAGGTGCAACTGGTGGAATCTGG<br>GGGAGGCTTAGTGAAGCCTGGAGGG<br>TCCCTGAAACTCTCCTGTGCAGCCTC<br>TGGATTCACTTTCAGTTCCTATGGCAT<br>GTCTTGGGTTCGTCAGACTCCGGAGA<br>AGAGGCTGGAGTGGGTCGCGACCATT<br>AGTGGTGGTGGTCGTGACACCTACTA<br>TTCAGACAGTGTGAAGGGGCGGTTCA<br>CCGTCTCCAGAGACAATGCCAAGAAC<br>AACCTGTTCCTGCAAATGAGCAGTCT<br>GAGGTCTGAAGACACGGCCTTGTATT<br>ATTGTTCACGTCAATATGGTACGGTCT<br>GGTTTTTTAACTGGGGCCAGGGGACT<br>CTGGTCACTGTCTCTGCA |
| SEQ ID NO: 4 | Nucleotide sequence of heavy chain variable region of murine antibody PD1-M944 | GAGGTGCAACTGGTGGAATCTGG<br>GGGAGGCTTAGTGAAGCCTGGAGGG<br>TCCCTGAAACTCTCCTGTGCAGCCTC<br>TGGATTCACTTTCAGTTCCTATGGCAT<br>GTCTTGGGTTCGTCAGACTCCGGAGA<br>AGAGGCTGGAGTGGGTCGCGACCATT<br>AGTGGTGGTGGTCGTGACACCTACTA<br>TTCAGACAGTGTGAAGGGGCGGTTCA<br>CCGTCTCCAGAGACAATGCCAAGAAC<br>AACCTGTTCCTGCAAATGAGCAGTCT<br>GAGGTCTGAAGACACGGCCTTGTATT<br>ATTGTTCACGTCAATATGGTACGGTCT<br>GGTTTTTTAACTGGGGCCAGGGGACT<br>CTGGTCACTGTCTCTGCA |
| SEQ ID NO: 5 | Nucleotide sequence of light chain variable region of murine antibody PD1-M944 | GATATTGTGCTAACTCAATCTCCA<br>GCTTCTTTGGCTGTGTCTCTAGGGCA<br>GAGGGCCACCATATCCTGCAGAGCCA<br>GTGAAAGTGTTGATAGTTATGGCAATA<br>GTTTTATGCACTGGTACCAGCAGAAA<br>CCAGGACAGCCACCCAAACTCCTCAT<br>CTATGCTGCATCCAACCAAGGATCCG<br>GGGTCCCTGCCAGGTTTAGTGGCAGT<br>GGGTCTGGGACAGACTTCAGCCTCAA<br>CATCCATCCTATGGAGGAGGATGATAC<br>TGCAATGTATTTCTGTCAGCAAAGTAA<br>GGAGGTTCCGTGGACGTTCGGTGGAG<br>GCACCAAGCTGGAAATCAAA |
| SEQ ID NO: 6 | Nucleotide sequence of the heavy chain constant region of mouse IgG1 | GCCAAAACGACACCCCCATCTGTC<br>TATCCACTGGCCCCTGGATCTGCTGCC<br>CAAACTAACTCCATGGTGACCCTGGG<br>ATGCCTGGTCAAGGGCTATTTCCCTG<br>AGCCAGTGACAGTGACCTGGAACTCT<br>GGATCCCTGTCCAGCGGTGTGCACAC<br>CTTCCCAGCTGTCCTGCAGTCTGACC<br>TCTACACTCTGAGCAGCTCAGTGACT<br>GTCCCCTCCAGCACCTGGCCCAGCGA<br>GACCGTCACCTGCAACGTTGCCCACC<br>CGGCCAGCAGCACCAAGGTGGACAA<br>GAAAATTGTGCCCAGGGATTGTGGTT<br>GTAAGCCTTGCATATGTACAGTCCCAG<br>AAGTATCATCTGTCTTCATCTTCCCCC<br>CAAAGCCCAAGGATGTGCTCACCATT<br>ACTCTGACTCCTAAGGTCACGTGTGT<br>TGTGGTAGACATCAGCAAGGATGATC<br>CCGAGGTCCAGTTCAGCTGGTTTGTA<br>GATGATGTGGAGGTGCACACAGCTCA<br>GACGCAACCCCGGGAGGAGCAGTTC<br>AACAGCACTTTCCGCTCAGTCAGTGA<br>ACTTCCCATCATGCACCAGGACTGGC |

TABLE 2-continued

Amino acid sequences and nucleotide sequences of murine-derived and humanized antibodies

| NOs | Name | Sequences |
|---|---|---|
| | | TCAATGGCAAGGAGTTCAAATGCAGG<br>GTCAACAGTGCAGCTTTCCCTGCCCC<br>CATCGAGAAAACCATCTCCAAAACCA<br>AAGGCAGACCGAAGGCTCCACAGGT<br>GTACACCATTCCACCTCCCAAGGAGC<br>AGATGGCCAAGGATAAAGTCAGTCTG<br>ACCTGCATGATAACAGACTTCTTCCCT<br>GAAGACATTACTGTGGAGTGGCAGTG<br>GAATGGGCAGCCAGCGGAGAACTAC<br>AAGAACACTCAGCCCATCATGGACAC<br>AGATGGCTCTTACTTCGTCTACAGCA<br>AGCTCAATGTGCAGAAGAGCAACTG<br>GGAGGCAGGAAATACTTTCACCTGCT<br>CTGTGTTACATGAGGGCCTGCACAAC<br>CACCATACTGAGAAGAGCCTCTCCCA<br>CTCTCCTGGTAAA |
| SEQ ID NO: 7 | Nucleotide sequence of the constant region of the mouse kappa light chain | CGGGCTGATGCTGCACCAACTGTA<br>TCCATCTTCCCACCATCCAGTGAGCA<br>GTTAACATCTGGAGGTGCCTCAGTCG<br>TGTGCTTCTTGAACAACTTCTACCCC<br>AAAGACATCAATGTCAAGTGGAAGAT<br>TGATGGCAGTGAACGACAAAATGGCG<br>TCCTGAACAGTTGGACTGATCAGGAC<br>AGCAAAGACAGCACCTACAGCATGA<br>GCAGCACCCTCACGTTGACCAAGGAC<br>GAGTATGAACGACATAACAGCTATAC<br>CTGTGAGGCCACTCACAAGACATCAA<br>CTTCACCCATTGTCAAGAGCTTCAAC<br>AGGAATGAGTGT |
| SEQ ID NO: 8 | Amino acid sequence of the heavy chain variable region of murine antibody PD1-M944 | EVQLVESGGGLVKPGGSLKLSCAA<br>SGFTFSSYGMSWVRQTPEKRLEWVATI<br>SGGGRDTYYSDSVKGRFTVSRDNAKN<br>NLFLQMSSLRSEDTALYYCSRQYGTV<br>WFFNWGQGTLVTVSA |
| SEQ ID NO: 9 | Amino acid sequence of the light chain variable region of murine antibody PD1-M944 | DIVLTQSPASLAVSLGQRATISCRAS<br>ESVDSYGNSFMHWYQQKPGQPPKLLI<br>YAASNQGSGVPARFSGSGSGTDFSLNIH<br>PMEEDDTAMYFCQQSKEVPWTFGGGT<br>KLEIK |
| SEQ ID NO: 10 | Amino acid sequence of light chain CDR1 of murine antibody PD1-M944/humanized antibody PD1-H944 | ESVDSYGNSFMH |
| SEQ ID NO: 11 | Amino acid sequence of light chain CDR2 of murine antibody PD1-M944/humanized antibody PD1-H944 | AASNQGSGVPA |
| SEQ ID NO: 12 | Amino acid sequence of light chain CDR3 of murine antibody PD1-M944/humanized antibody PD1-H944 | QQSKEVPWT |
| SEQ ID NO: 13 | Amino acid sequence of heavy chain CDR1 of murine antibody PD1-M944/humanized antibody PD1-H944 | GFTFSSYGMS |
| SEQ ID NO: 14 | Amino acid sequence of heavy chain CDR2 of murine antibody PD1-M944/humanized antibody PD1-H944 | VATISGGGRDTYYSDSVKG |

TABLE 2-continued

Amino acid sequences and nucleotide sequences of murine-derived and humanized antibodies

| NOs | Name | Sequences |
| --- | --- | --- |
| SEQ ID NO: 15 | Amino acid sequence of heavy chain CDR3 of murine antibody PD1-M944/humanized antibody PD1-H944 | SRQYGTVWFFN |
| SEQ ID NO: 16 | Amino acid sequence of the heavy chain of humanized antibody PD1-H944 | Amino acid sequence of the heavy chain variable region (SEQ ID NO: 22): EVQLVESGGGLVKPGGSLRLSCAASGFTFSSY GMSWVRQAPGKRLEWVATISGGGRDTYYSDSVK GRFTISRDNAKNNLYLQMNSLRAEDTAVYYCSRQ YGTVWFFNWGQGTLVTVSS<br>Amino acid sequence of heavy chain constant region (SEQ ID NO: 24): ASTKGPSVFPLAPCSRSTSESTAALG CLVKDYFPEPVTVSWNSGALTSGVHTF PAVLQSSGLYSLSSVVTVPSSSLGTKTY TCNVDHKPSNTKVDKRVESKYGPPCPP CPAPEFLGGPSVFLFPPKPKDTLMISRTP EVTCVVVDVSQEDPEVQFNWYVDGVE VHNAKTKPREEQFNSTYRVVSVLTVLH QDWLNGKEYKCKVSNKGLPSSIEKTIS KAKGQPREPQVYTLPPSQEEMTKNQV SLTCLVKGFYPSDIAVEWESNGQPENN YKTTPPVLDSDGSFFLYSRLTVDKSRW QEGNVFSCSVMHEALHNHYTQKSLSL SLGK |
| SEQ ID NO: 17 | Amino acid sequence of the light chain of humanized antibody PD1-H944 | Amino acid sequence of the light chain variable region (SEQ ID NO: 23): EIVLTQSPATLSLSPGERATLSCRAS ESVDSYGNSFMHWYQQKPGQPPRLLI YAASNQGSGVPARFSGSGSGTDFTLTIS SLEPEDFAMYFCQQSKEVPWTFGQGT KVEIK<br>Amino acid sequence of the light chain constant region (SEQ ID NO: 25): RTVAAPSVFIFPPSDEQLKSGTASVV CLLNNFYPREAKVQWKVDNALQSGNS QESVTEQDSKDSTYSLSSTLTLSKADYE KHKVYACEVTHQGLSSPVTKSFNRGEC |
| SEQ ID NO: 18 | Amino acid sequence of the heavy chain of the humanized antibody PD1-H944 containing the signal peptide | Amino acid sequence of the heavy chain signal peptide (SEQ ID NO: 20): MGWSLILLFLVAVATRVLS<br>Amino acid sequence of the heavy chain variable region (SEQ ID NO: 22): EVQLVESGGGLVKPGGSLRLSCAAS GFTFSSYGMSWVRQAPGKRLEWVATIS GGGRDTYYSDSVKGRFTISRDNAKNN LYLQMNSLRAEDTAVYYCSRQYGTVW FFNWGQGTLVTVSS<br>Amino acid sequence of the heavy chain constant region (SEQ ID NO: 24): ASTKGPSVFPLAPCSRSTSESTAALG CLVKDYFPEPVTVSWNSGALTSGVHTF PAVLQSSGLYSLSSVVTVPSSSLGTKTY TCNVDHKPSNTKVDKRVESKYGPPCPP CPAPEFLGGPSVFLFPPKPKDTLMISRTP EVTCVVVDVSQEDPEVQFNWYVDGVE VHNAKTKPREEQFNSTYRVVSVLTVLH QDWLNGKEYKCKVSNKGLPSSIEKTIS KAKGQPREPQVYTLPPSQEEMTKNQV SLTCLVKGFYPSDIAVEWESNGQPENN YKTTPPVLDSDGSFFLYSRLTVDKSRW QEGNVFSCSVMHEALHNHYTQKSLSL SLGK |

TABLE 2-continued

Amino acid sequences and nucleotide sequences of murine-derived and humanized antibodies

| NOs | Name | Sequences |
| --- | --- | --- |
| SEQ ID NO: 19 | Amino acid sequence of the light chain of the humanized antibody PD1-H944 containing the signal peptide | Amino acid sequence of the light chain signal peptide (SEQ ID NO: 21):<br>MGWSCIILFLVATATGVHS<br>Amino acid sequence of the light chain variable region (SEQ ID NO: 23):<br>EIVLTQSPATLSLSPGERATLSCRAS<br>ESVDSYGNSFMHWYQQKPGQPPRLLI<br>YAASNQGSGVPARFSGSGSGTDFTLTIS<br>SLEPEDFAMYFCQQSKEVPWTFGQGT<br>KVEIK<br>Amino acid sequence of the light chain constant region (SEQ ID NO: 25):<br>RTVAAPSVFIFPPSDEQLKSGTASVV<br>CLLNNFYPREAKVQWKVDNALQSGNS<br>QESVTEQDSKDSTYSLSSTLTLSKADYE<br>KHKVYACEVTHQGLSSPVTKSFNRGEC |
| SEQ ID NO: 20 | Amino acid sequence of the humanized antibody PD1-H944 heavy chain signal peptide | MGWSLILLFLVAVATRVLS |
| SEQ ID NO: 21 | Amino acid sequence of the humanized antibody PD1-H944 light chain signal peptide | MGWSCIILFLVATATGVHS |
| SEQ ID NO: 22 | Amino acid sequence of the heavy chain variable region of the humanized antibody PD1-H944 | EVQLVESGGGLVKPGGSLRLSCAAS<br>GFTFSSYGMSWVRQAPGKRLEWVATIS<br>GGGRDTYYSDSVKGRFTISRDNAKNN<br>LYLQMNSLRAEDTAVYYCSRQYGTVW<br>FFNWGQGTLVTVSS |
| SEQ ID NO: 23 | Amino acid sequence of the light chain variable region of humanized antibody PD1-H944 | EIVLTQSPATLSLSPGERATLSCRAS<br>ESVDSYGNSFMHWYQQKPGQPPRLLI<br>YAASNQGSGVPARFSGSGSGTDFTLTIS<br>SLEPEDFAMYFCQQSKEVPWTFGQGT<br>KVEIK |
| SEQ ID NO: 24 | Amino acid sequence of the heavy chain constant region of humanized antibody PD1-H944 | ASTKGPSVFPLAPCSRSTSESTAALG<br>CLVKDYFPEPVTVSWNSGALTSGVHTF<br>PAVLQSSGLYSLSSVVTVPSSSLGTKTY<br>TCNVDHKPSNTKVDKRVESKYGPPCPP<br>CPAPEFLGGPSVFLFPPKPKDTLMISRTP<br>EVTCVVVDVSQEDPEVQFNWYVDGVE<br>VHNAKTKPREEQFNSTYRVVSVLTVLH<br>QDWLNGKEYKCKVSNKGLPSSIEKTIS<br>KAKGQPREPQVYTLPPSQEEMTKNQV<br>SLTCLVKGFYPSDIAVEWESNGQPENN<br>YKTTPPVLDSDGSFFLYSRLTVDKSRW<br>QEGNVFSCSVMHEALHNHYTQKSLSL<br>SLGK |
| SEQ ID NO: 25 | Amino acid sequence of the light chain constant region of humanized antibody PD1-H944 | RTVAAPSVFIFPPSDEQLKSGTASVV<br>CLLNNFYPREAKVQWKVDNALQSGNS<br>QESVTEQDSKDSTYSLSSTLTLSKADYE<br>KHKVYACEVTHQGLSSPVTKSFNRGEC |
| SEQ ID NO: 26 | Nucleotide sequence of the humanized antibody PD1-H944 heavy chain containing the signal peptide | Nucleotide sequence of heavy chain signal peptide (SEQ ID NO: 28):<br>ATGGGCTGGTCCCTGATTCTGCTG<br>TTCCTGGTGGCTGTGGCTACCAGGGT<br>GCTGTCT<br>Nucleotide sequence of heavy chain variable region (SEQ ID NO: 30:)<br>GAGGTCCAACTTGTGGAGTCTGG<br>AGGAGGACTGGTGAAGCCTGGAGGC<br>TCCCTGAGACTGTCCTGTGCTGCCTC<br>TGGCTTCACCTTCTCCTCCTATGGGAT<br>GAGTTGGGTGAGACAGGCTCCTGGG<br>AAGAGATTGGAGTGGGTGGCTACCAT |

TABLE 2-continued

Amino acid sequences and nucleotide sequences of murine-derived and humanized antibodies

| NOs | Name | Sequences |
|---|---|---|
| | | CTCTGGAGGAGGCAGGGACACCTACT<br>ACTCTGACTCTGTGAAGGGCAGGTTC<br>ACAATCAGCAGGGACAATGCCAAGA<br>ACAACCTGTACCTCCAAATGAACTCC<br>CTGAGGGCTGAGGACACAGCAGTCTA<br>CTACTGTAGCAGACAATATGGCACAG<br>TGTGGTTCTTCAACTGGGGACAAGGC<br>ACCCTGGTGACAGTGTCCTCT<br>Nucleotide sequence of the heavy chain constant region (SEQ ID NO: 32):<br>GCTAGCACCAAGGGCCCATCGGTC<br>TTCCCGCTGGCGCCCTGCTCCAGGAG<br>CACCTCCGAGAGCACAGCCGCCCTGG<br>GCTGCCTGGTCAAGGACTACTTCCCC<br>GAACCGGTGACGGTGTCGTGGAACTC<br>AGGCGCCCTGACCAGCGGCGTGCAC<br>ACCTTCCCGGCTGTCCTACAGTCCTC<br>AGGACTCTACTCCCTCAGCAGCGTGG<br>TGACCGTGCCCTCCAGCAGCTTGGGC<br>ACGAAGACCTACACCTGCAACGTAGA<br>TCACAAGCCCAGCAACACCAAGGTG<br>GACAAGAGAGTTGAGTCCAAATATGG<br>TCCCCCATGCCCACCCTGCCCAGCAC<br>CTGAGTTCCTGGGGGGACCATCAGTC<br>TTCCTGTTCCCCCCAAAACCCAAGGA<br>CACTCTCATGATCTCCCGGACCCCTG<br>AGGTCACGTGCGTGGTGGTGGACGTG<br>AGCCAGGAAGACCCCGAGGTCCAGT<br>TCAACTGGTACGTGGATGGCGTGGAG<br>GTGCATAATGCCAAGACAAAGCCGCG<br>GGAGGAGCAGTTCAACAGCACGTAC<br>CGTGTGGTCAGCGTCCTCACCGTCCT<br>GCACCAGGACTGGCTGAACGGCAAG<br>GAGTACAAGTGCAAGGTCTCCAACAA<br>AGGCCTCCCGTCCTCCATCGAGAAAA<br>CCATCTCCAAAGCCAAAGGGCAGCCC<br>CGAGAGCCACAGGTGTACACCCTGCC<br>CCCATCCCAGGAGGAGATGACCAAGA<br>ACCAGGTCAGCCTGACCTGCCTGGTC<br>AAAGGCTTCTACCCCAGCGACATCGC<br>CGTGGAGTGGGAAAGCAATGGGCAG<br>CCGGAGAACAACTACAAGACCACGC<br>CTCCCGTGCTGGACTCCGACGGCTCC<br>TTCTTCCTCTACAGCAGGCTAACCGT<br>GGACAAGAGCAGGTGGCAGGAGGGG<br>AATGTCTTCTCATGCTCCGTGATGCAT<br>GAGGCTCTGCACAACCACTACACACA<br>GAAGAGCCTCTCCCTGTCTCTGGGTA<br>AATAA |
| SEQ ID NO: 27 | Nucleotide sequence of humanized antibody PD1-H944 light chain containing signal peptide | Nucleotide sequence of the light chain signal peptide (SEQ ID NO: 29):<br>ATGGGCTGGTCCTGTATCATCCTG<br>TTCCTGGTGGCTACAGCCACAGGAGT<br>GCATTCT<br>Nucleotide sequence of the light chain variable region (SEQ ID NO: 31):<br>GAGATTGTGCTGACCCAGAGCCCT<br>GCCACCCTGTCCCTGAGCCCTGGAGA<br>GAGGGCTACCCTGTCCTGTAGGGCAT<br>CTGAGTCTGTGGACTCCTATGGCAAC<br>TCCTTTATGCACTGGTATCAACAGAAG<br>CCTGGACAACCACCAAGACTGCTGAT<br>TTATGCTGCCAGCAACCAGGGCTCTG<br>GAGTGCCTGCCAGGTTCTCTGGCTCT<br>GGCTCTGGCACAGACTTCACCCTGAC<br>CATCTCCTCCTTGGAACCTGAGGACT<br>TTGCTATGTACTTCTGTCAACAGAGCA<br>AGGAGGTGCCATGGACCTTTGGACAA<br>GGCACCAAGGTGGAGATTAAG<br>Nucleotide sequence of the light chain constant region (SEQ ID NO: 33):<br>CGTACGGTGGCTGCACCATCTGTC<br>TTCATCTTCCCGCCATCTGATGAGCAG<br>TTGAAATCTGGAACTGCCTCTGTTGT |

TABLE 2-continued

Amino acid sequences and nucleotide sequences of murine-derived and humanized antibodies

| NOs | Name | Sequences |
|---|---|---|
| | | GTGCCTGCTGAATAACTTCTATCCCAG<br>AGAGGCCAAAGTACAGTGGAAGGTG<br>GATAACGCCCTCCAATCGGGTAACTC<br>CCAGGAGAGTGTCACAGAGCAGGAC<br>AGCAAGGACAGCACCTACAGCCTCA<br>GCAGCACCCTGACGCTGAGCAAAGC<br>AGACTACGAGAAACACAAAGTCTAC<br>GCCTGCGAAGTCACCCATCAGGGCCT<br>GAGCTCGCCCGTCACAAAGAGCTTCA<br>ACAGGGGAGAGTGTTAG |
| SEQ ID NO: 28 | Nucleotide sequence of humanized antibody PD1-H944 heavy chain signal peptide | ATGGGCTGGTCCCTGATTCTGCTG<br>TTCCTGGTGGCTGTGGCTACCAGGGT<br>GCTGTCT |
| SEQ ID NO: 29 | Nucleotide sequence of the humanized antibody PD1-H944 light chain signal peptide | ATGGGCTGGTCCTGTATCATCCTG<br>TTCCTGGTGGCTACAGCCACAGGAGT<br>GCATTCT |
| SEQ ID NO: 30 | Nucleotide sequence of the heavy chain variable region of humanized antibody PD1-H944 | GAGGTCCAACTTGTGGAGTCTGG<br>AGGAGGACTGGTGAAGCCTGGAGGC<br>TCCCTGAGACTGTCCTGTGCTGCCTC<br>TGGCTTCACCTTCTCCTCCTATGGGAT<br>GAGTTGGGTGAGACAGGCTCCTGGG<br>AAGAGATTGGAGTGGGTGGCTACCAT<br>CTCTGGAGGAGGCAGGGACACCTACT<br>ACTCTGACTCTGTGAAGGGCAGGTTC<br>ACAATCAGCAGGGACAATGCCAAGA<br>ACAACCTGTACCTCCAAATGAACTCC<br>CTGAGGGCTGAGGACACAGCAGTCTA<br>CTACTGTAGCAGACAATATGGCACAG<br>TGTGGTTCTTCAACTGGGGACAAGGC<br>ACCCTGGTGACAGTGTCCTCT |
| SEQ ID NO: 31 | Nucleotide sequence of the light chain variable region of the humanized antibody PD1-H944 | GAGATTGTGCTGACCCAGAGCCCT<br>GCCACCCTGTCCCTGAGCCCTGGAGA<br>GAGGGCTACCCTGTCCTGTAGGGCAT<br>CTGAGTCTGTGGACTCCTATGGCAAC<br>TCCTTTATGCACTGGTATCAACAGAAG<br>CCTGGACAACCACCAAGACTGCTGAT<br>TTATGCTGCCAGCAACCAGGGCTCTG<br>GAGTGCCTGCCAGGTTCTCTGGCTCT<br>GGCTCTGGCACAGACTTCACCCTGAC<br>CATCTCCTCCTTGGAACCTGAGGACT<br>TTGCTATGTACTTCTGTCAACAGAGCA<br>AGGAGGTGCCATGGACCTTTGGACAA<br>GGCACCAAGGTGGAGATTAAG |
| SEQ ID NO: 32 | Nucleotide sequence of the heavy chain constant region of humanized antibody PD1-H944 | GCTAGCACCAAGGGCCCATCGGTC<br>TTCCCGCTGGCGCCCTGCTCCAGGAG<br>CACCTCCGAGAGCACAGCCGCCCTGG<br>GCTGCCTGGTCAAGGACTACTTCCCC<br>GAACCGGTGACGGTGTCGTGGAACTC<br>AGGCGCCCTGACCAGCGGCGTGCAC<br>ACCTTCCCGGCTGTCCTACAGTCCTC<br>AGGACTCTACTCCCTCAGCAGCGTGG<br>TGACCGTGCCCTCCAGCAGCTTGGGC<br>ACGAAGACCTACACCTGCAACGTAGA<br>TCACAAGCCCAGCAACACCAAGGTG<br>GACAAGAGAGTTGAGTCCAAATATGG<br>TCCCCCATGCCCACCCTGCCCAGCAC<br>CTGAGTTCCTGGGGGGACCATCAGTC<br>TTCCTGTTCCCCCCAAAACCCAAGGA<br>CACTCTCATGATCTCCCGGACCCCTG<br>AGGTCACGTGCGTGGTGGTGGACGTG<br>AGCCAGGAAGACCCCGAGGTCCAGT<br>TCAACTGGTACGTGGATGGCGTGGAG<br>GTGCATAATGCCAAGACAAAGCCGCG<br>GGAGGAGCAGTTCAACAGCACGTAC<br>CGTGTGGTCAGCGTCCTCACCGTCCT<br>GCACCAGGACTGGCTGAACGGCAAG<br>GAGTACAAGTGCAAGGTCTCCAACAA<br>AGGCCTCCCGTCCTCCATCGAGAAAA |

TABLE 2-continued

Amino acid sequences and nucleotide sequences of murine-derived and humanized antibodies

| NOs | Name | Sequences |
|---|---|---|
| | | CCATCTCCAAAGCCAAAGGGCAGCCC<br>CGAGAGCCACAGGTGTACACCCTGCC<br>CCCATCCCAGGAGGAGATGACCAAGA<br>ACCAGGTCAGCCTGACCTGCCTGGTC<br>AAAGGCTTCTACCCCAGCGACATCGC<br>CGTGGAGTGGGAAAGCAATGGGCAG<br>CCGGAGAACAACTACAAGACCACGC<br>CTCCCGTGCTGGACTCCGACGGCTCC<br>TTCTTCCTCTACAGCAGGCTAACCGT<br>GGACAAGAGCAGGTGGCAGGAGGGG<br>AATGTCTTCTCATGCTCCGTGATGCAT<br>GAGGCTCTGCACAACCACTACACACA<br>GAAGAGCCTCTCCCTGTCTCTGGGTA<br>AATAA |
| SEQ ID NO: 33 | Nucleotide sequence of the light chain constant region of humanized antibody PD1-H944 | CGTACGGTGGCTGCACCATCTGTC<br>TTCATCTTCCCGCCATCTGATGAGCAG<br>TTGAAATCTGGAACTGCCTCTGTTGT<br>GTGCCTGCTGAATAACTTCTATCCCAG<br>AGAGGCCAAAGTACAGTGGAAGGTG<br>GATAACGCCCTCCAATCGGGTAACTC<br>CCAGGAGAGTGTCACAGAGCAGGAC<br>AGCAAGGACAGCACCTACAGCCTCA<br>GCAGCACCCTGACGCTGAGCAAAGC<br>AGACTACGAGAAACACAAAGTCTAC<br>GCCTGCGAAGTCACCCATCAGGGCCT<br>GAGCTCGCCCGTCACAAAGAGCTTCA<br>ACAGGGGAGAGTGTTAG |
| SEQ ID NO: 34 | Amino acid sequence of murine antibody PD1-M944 Scfv | Amino acid sequence of PD1-M944 light chain variable region (SEQ ID NO: 9):<br>DIVLTQSPASLAVSLGQRATISCRAS<br>ESVDSYGNSFMHWYQQKPGQPPKLLI<br>YAASNQGSGVPARFSGSGSGTDFSLNIH<br>PMEEDDTAMYFCQQSKEVPWTFGGGT<br>KLEIK<br>Linker (SEQ ID NO: 35):<br>SSGGGGSGGGGGSSRSS<br>Amino acid sequence of PD1-M944 heavy chain variable region (SEQ ID NO: 8):<br>EVQLVESGGGLVKPGGSLKLSCAA<br>SGFTFSSYGMSWVRQTPEKRLEWVATI<br>SGGGRDTYYSDSVKGRFTVSRDNAKN<br>NLFLQMSSLRSEDTALYYCSRQYGTV<br>WFFNWGQGTLVTVSA |
| SEQ ID NO: 35 | Linker amino acid sequence of the murine antibody scFv used in the construction of the phage antibody library | SSGGGGSGGGGGSSRSS |

Example 3: Production of Humanized Antibody PD1-H944

After PCR amplification, the respective above heavy/light chain nucleotide sequences encoding the signal peptide containing PD1-H944 antibody (SEQ ID NO:26/27), which contains the nucleotide sequence coding for the sequentially linked heavy/light chain signal peptide (SEQ ID NO:28/29), the heavy/light chain variable region of the humanized antibody (SEQ ID NO:30/31) and the human IgG4 heavy chain constant region/human kappa light chain constant region (SEQ ID NO:32/33), respectively, were double digested with restriction endonucleases Hind III and Xba I (Fermentas) then inserted into the commercial vector pcDNA3 (Invitrogen). After plasmid extraction, a 1.8 kb fragment was obtained by triple digestion of pCDNA3 light chain vector with NruI+NaeI+Dra I then inserted into the CHO/dhfr system expression vector pSSE (Sino Biological, Inc), then a 2.5 kb fragment was obtained by triple digestion of the pCDNA3 heavy chain vector with NruI+NaeI+Dra I (Fermentas). Then also inserted to the pSSE (Sino Biological, Inc) light chain vector constructed in the previous step to obtain the complete vector. The expression vector is a eukaryotic expression vector containing the DNA amplification element dhfr gene, the NeoR resistance gene and the expression elements of the antibody light and heavy chains. The expression vector was transfected into dhfr-DG44 cells, PD1-H944 positive cell lines were obtained by G418 screening, PD1-H944 high expression cell lines were obtained by MTX stepwise pressure screening, and then domesticated in serum-free culture for clonal screening. At each step, the clone with high antibody expression were selected on the ground of ELISA assay outcomes, together with cell growth status and the key quality attributes of the antibody drug.

The PD1-H944 producing CHO cell line was cultured in serum-free supplement suspension culture to obtain PD1-H944 antibody of high purity and quality.

Example 4: Characterization of the Humanized Antibody PD1-H944

Figure 2:
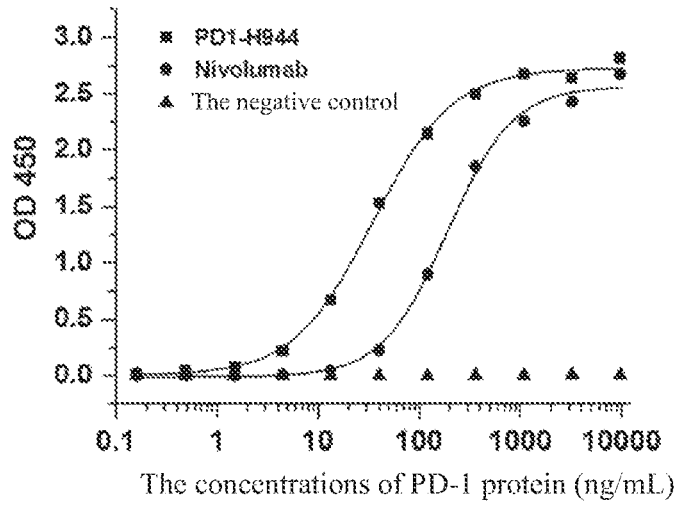
FIG. 2: ELISA detection of the binding of humanized antibody PD1-H944 to recombinant human PD-1 protein (A, B, C, n=3).
Figure 2:
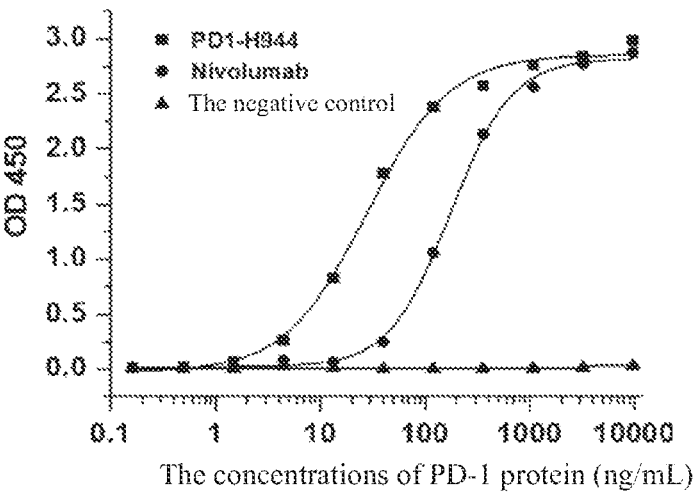
Figure 2:
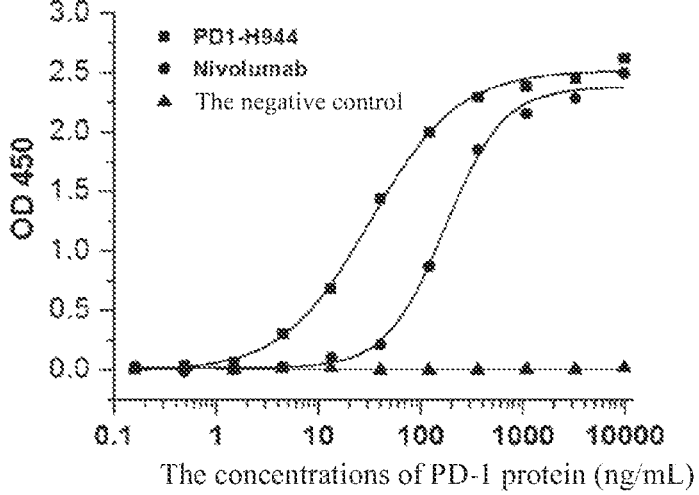

4.1 Assay of the Binding Affinity of PD1-H944 to Human, Mouse and Monkey PD-1 Antigen (1) Binding Ability of PD1-H944 to Recombinant Human PD-1 Protein An indirect ELISA was used to detect the specific binding of PD1-H944 to recombinant human PD-1 protein. Different concentrations (0.16 ng/mL, 0.49 ng/mL, 1.48 ng/mL, 4.44 ng/mL, 13.33 ng/mL, 40 ng/mL, 120 ng/mL, 360 ng/mL, 1080 ng/mL, 3240 ng/mL and 9720 ng/mL) of recombinant human PD-1 protein was coated on 96-well plates overnight at 4° C. On the next day, the plates were washed and blocked at room temperature for 1 h. After incubation with 100 μL of 2 μg/mL of PD1-H944, Nivolumab (Bristol-Myers Squibb) and negative control antibody H7N9-R1-IgG4 (Sino Biological, Inc.) respectively, the plates were washed to remove unbound antibody, then incubated with goat anti-human IgG F(ab)2/HRP (JACKSON) and washed repeatedly, and the substrate chromogenic solution was added for color development and detection of OD450. EC50 of PD-1-H944 and Nivolumab binding to recombinant human PD-1 protein was 31.5 ng/mL, $R^2$=0.998 and 179.0 ng/mL, $R^2$=0.997, respectively. This indicates that PD1-H944 binds recombinant human PD-1 protein significantly better than Nivolumab (FIG. 2A-C).

(2) Binding Ability of PD1-H944 to Recombinant Jurkat/PD-1 Cells

Figure 3:
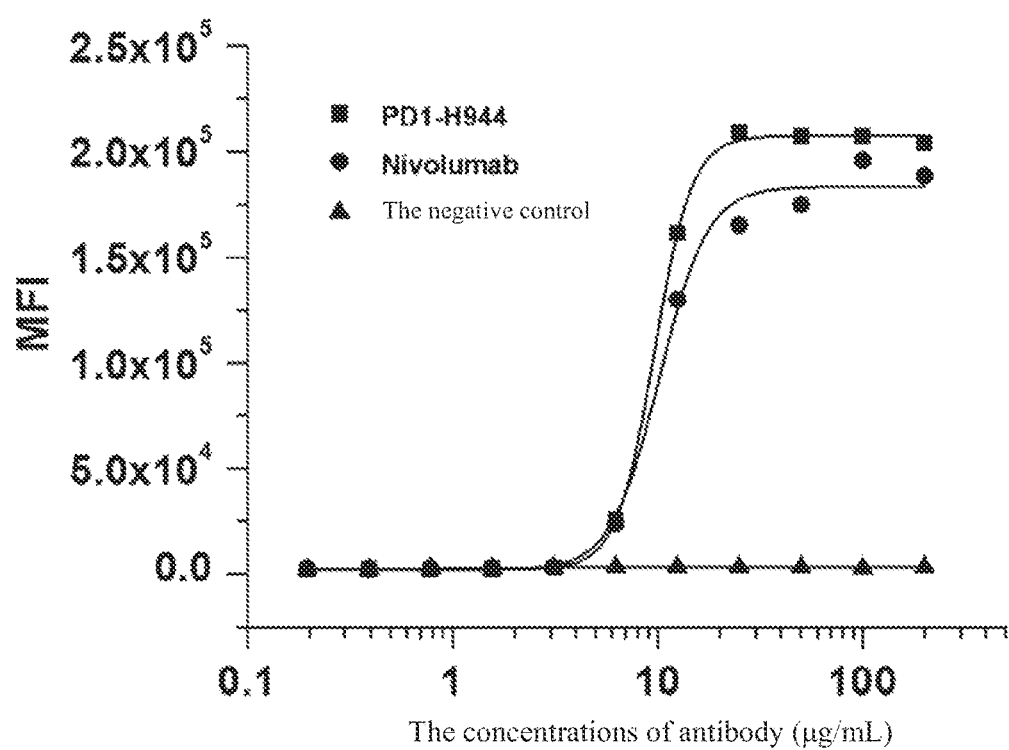
FIG. 3: FACS detection of the binding of PD1-H944 to recombinant Jurkat/PD-1 cells.

The binding ability of PD1-H944 to recombinant Jurkat/PD-1 cells was measured by flow cytometry using the recombinant human PD-1 stable expression cell line Jurkat/PD-1 (SinoCellTech Ltd) as the experiment material. PD1-H944, Nivolumab and the negative control antibody H7N9-R1-IgG4 in different concentrations (0.195 μg/mL, 0.391 μg/mL, 0.781 μg/mL, 1.562 μg/mL, 3.125 μg/mL, 6.25 μg/mL, 12.5 μg/mL, 25 μg/mL, 50 μg/mL, 100 μg/mL and 200 μg/mL) were added to $5 \times 10^5$/tube recombinant Jurkat/PD-1 cells in logarithmic growth phase, mixed and incubated at 4° C. and then washed and centrifuged to remove unbound antibody. The binding of the antibody to the cells was detected by adding goat anti-human IgG Fc-FITC (Sino Biological, Inc.). The results showed that PD1-H944 specifically bound to Jurkat/PD-1 cells with $EC_{50}$ of 9.63 μg/mL, $R^2$=1.000, Nivolumab specifically bound to Jurkat/PD-1 cells with $EC_{50}$ of 10.18 μg/mL, $R^2$=0.994, and the negative control antibody H7N9-R1-IgG4 did not bind to Jurkat/PD-1 cells (FIG. 3). This indicates that PD1-H944 has a good capability to bind to PD-1 expressed by Jurkat/PD-1 cells and that its binding capacity is slightly better than that of Nivolumab.

(3) Binding Affinity of PD1-H944 to Recombinant Human PD-1 Protein

Figure 4:
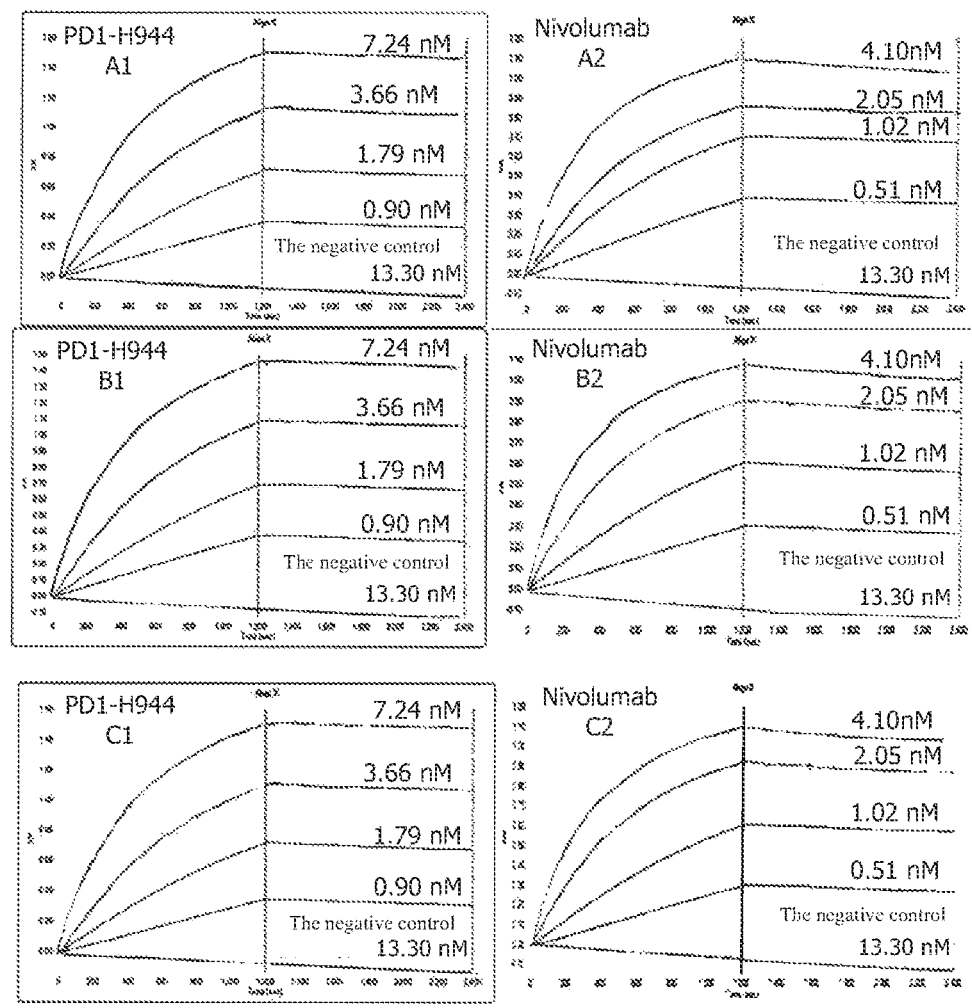
FIG. 4A: Octet assay for affinity of PD1-H944 (A1, n=3) and Nivolumab (A2, n=3) to recombinant human PD-1 protein.
FIG. 4B: Octet assay for affinity of PD1-H944 (B1, n=3) and Nivolumab (B2, n=3) to recombinant human PD-1 protein.
FIG. 4C: Octet assay for affinity of PD1-H944 (C1, n=3) and Nivolumab (C2, n=3) to recombinant human PD-1 protein.

The affinity of PD1-H944 (0.90 nM, 1.79 nM, 3.66 nM, 7.24 nM), Nivolumab (0.51 nM, 1.02 nM, 2.05 nM, 4.10 nM) to PD-1 was determined using the Octet Biomolecular Interaction Assay System, with H7N9-R1-IgG4 (13.30 nM) as the negative control antibody. The results showed that the mean KD binding affinity of PD1-H944 to recombinant human PD-1 protein was 64.8 pM, the mean association rate constant $k_{on}$ was 3.01E+05 $M^{-1}s^{-1}$ and the mean dissociation rate constant $k_{off}$ was 1.95E-05 $s^{-1}$; the mean KD binding affinity of Nivolumab to PD-1 protein was 74.1 pM, with a mean binding rate constant $k_{on}$ of 6.92E+05 $M^{-1}s^{-1}$ and a mean dissociation rate constant $k_{off}$ of 5.12E-05 $s^{-1}$ (FIGS. 4A-4C). PD1-H944 has a stronger affinity than Nivolumab, which is approximately 1.14 times of that of Nivolumab, and PD1-H944 has a lower dissociation rate, so PD1-H944 has a stronger ability to bind PD-1 protein than Nivolumab.

(4) Binding Ability of PD1-H944 to Recombinant Monkey and Mouse PD-1 Protein

Figure 5:
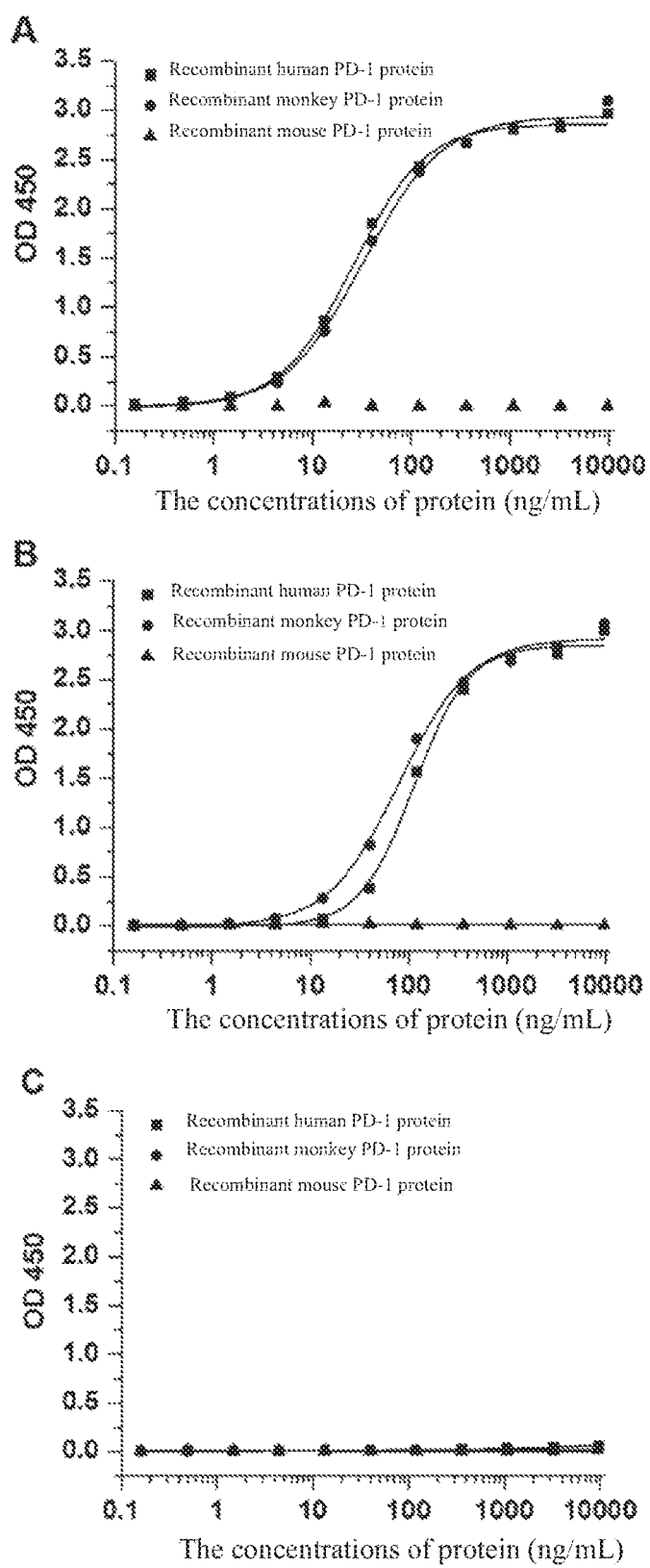
FIG. 5: ELISA for the binding of PD1-H944 (A), Nivolumab (B) and negative control (C) to recombinant human, monkey and mouse PD-1 protein.

An indirect ELISA was used to detect the specific binding of PD1-H944 to recombinant monkey and mouse PD-1 protein. recombinant human, monkey and mouse PD-1 proteins (Sino Biological, Inc.) with different concentrations (0.16 ng/mL, 0.49 ng/mL, 1.48 ng/mL, 4.44 ng/mL, 13.33 ng/mL, 40 ng/mL, 120 ng/mL, 360 ng/mL, 1080 ng/mL, 3240 ng/mL and 9720 ng/mL) were coated on 96-well plates, 100 μL per well, coated overnight at 4° C. Washed the next day and blocked at room temperature for 1 h. After incubation with 100 μL of PD1-H944, Nivolumab and the negative control antibody H7N9-R1-IgG4 (all in 2 μg/mL), the plates were washed and the secondary antibody, goat anti-human IgG F(ab)2/HRP, was added for color developement, $OD_{450}$ was detected, the assay was in triplet. The results showed that PD1-H944 could bind recombinant human PD-1 protein and recombinant monkey PD-1 protein with antigenic $EC_{50}$ of 25.8 ng/mL ($R^2$=0.999) and 32.7 ng/mL ($R^2$=0.997), respectively, while did not cross bind to recombinant mouse PD-1 protein (FIG. 5A); Nivolumab could bind recombinant human PD-1 protein and recombinant monkey PD-1 protein with $EC_{50}$ of 113.2 ng/mL ($R^2$=0.997) and 80.2 ng/mL ($R^2$=0.997), respectively, and did not bind to mouse PD-1 protein (FIG. 5B); the negative control antibody did not bind to recombinant human PD-1 protein, recombinant monkey PD-1 protein or recombinant mouse PD-1 protein (FIG. 5C). The good binding of PD1-H944 to monkey PD-1 supports the use of monkeys for the safety evaluation of this drug.

(5) Binding Affinity of PD1-H944 to Recombinant Monkey and Mouse PD-1 Protein

Figure 6:
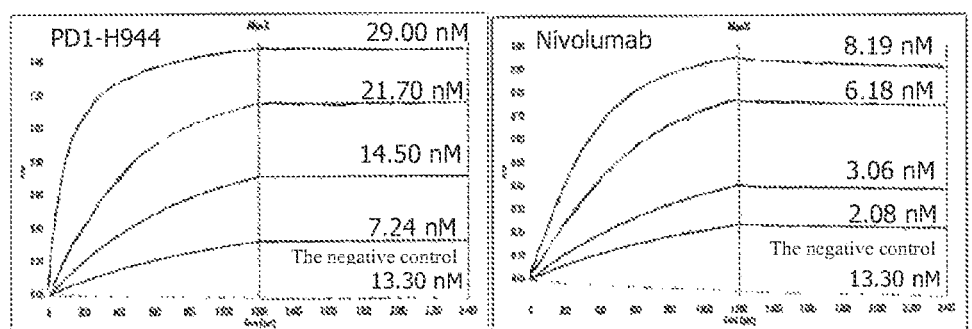
FIG. 6A: Binding of PD1-H944 and Nivolumab at different concentrations to monkey PD-1 protein.
FIG. 6B: Binding of PD1-H944 and Nivolumab at different concentrations to mouse PD-1 protein.
Figure 6:
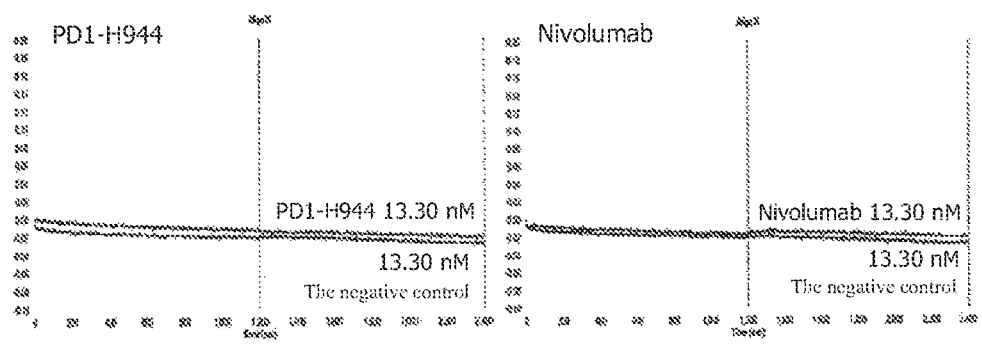

The affinity of PD1-H944 and Nivolumab to biotinylated monkey and mouse PD-1 proteins (Sino Biological, Inc.) at different concentration gradients (see FIG. 6A-B) was measured using Octet and analyzed to obtain KD values. The results showed that the affinity KD value of PD1-H944 with recombinant monkey PD-1 protein was 108 pM and the affinity KD value of Nivolumab with recombinant monkey PD-1 protein was 131 pM, which were comparable (FIG. 6A). Both PD1-H944 and Nivolumab did not bind to recombinant mouse PD-1 protein (FIG. 6B).

Figure 7:
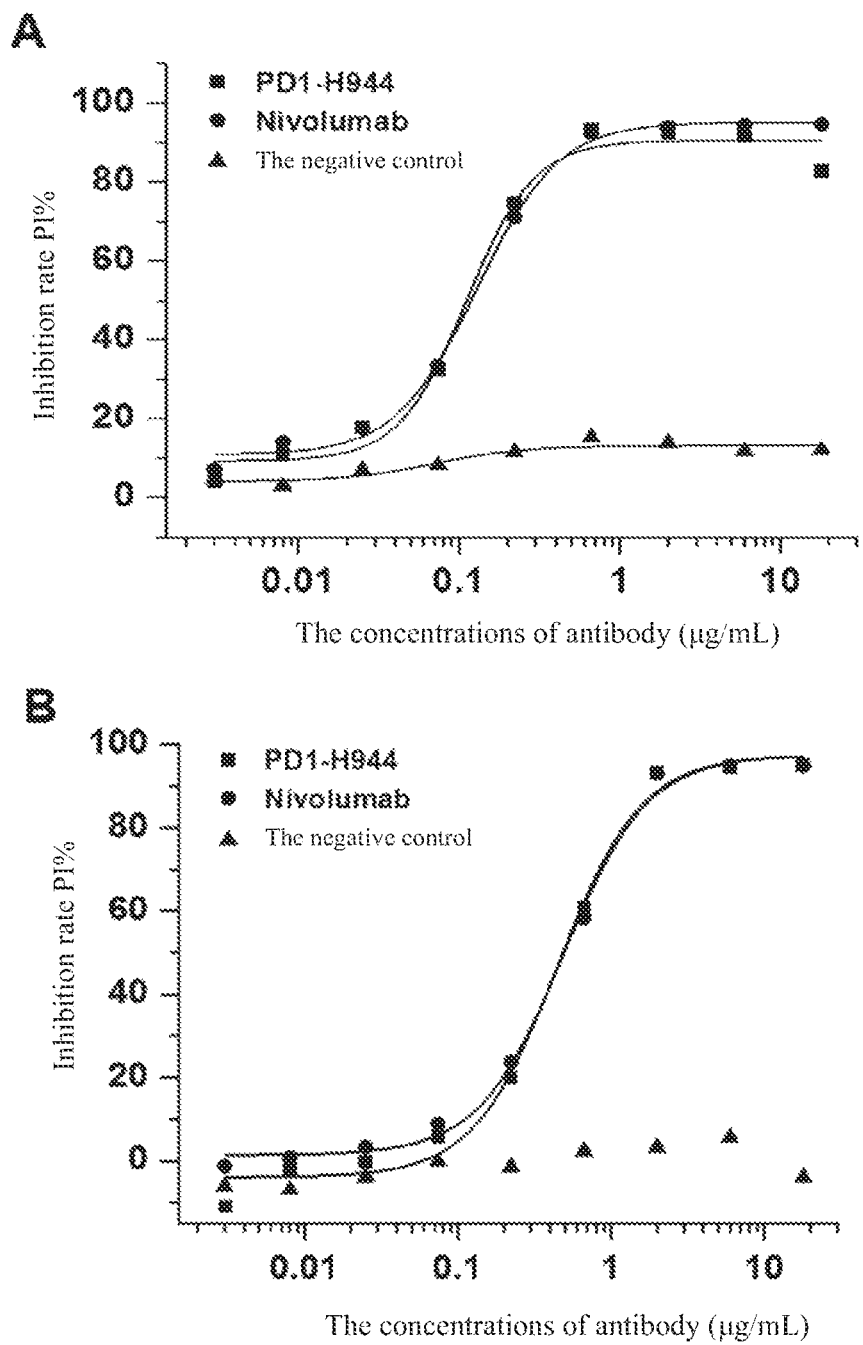
FIG. 7: ELISA detection of the blocking on the binding of human PD-L1 (A) and human PD-L2 (B) to recombinant human PD-1 protein by PD1-H944.

4.2 PD1-H944 Blocks the Binding of Human PD-1 Ligands (PD-L1 and PD-L2) to Human PD-1 Protein The recombinant human PD-1 protein was coated on a 96-well plate at 100 μL per well and left overnight at 4° C. The plate was washed the next day and blocked at room temperature for 1 hour before 1 μg/mL of human PD-L1-biotin (Sino Biological, Inc.) or 2 μg/mL of human PD-L2-biotin (Sino Biological, Inc.) was added. Then PD1-H944, Nivolumab or negative control antibody H7N9-R1-IgG4 in different concentrations (0.003 μg/mL, 0.008 μg/mL, 0.025 μg/mL, 0.074 μg/mL, 0.222 μg/mL, 0.667 μg/mL, 2 μg/mL, 6 μg/mL, 18 μg/mL) was added, incubated, antibiotic streptavidin/HRP was added, incubated, and $OD_{450}$ was detected. For each group, the test is performed in doublet. The results showed that biotinylated recombinant human PD-L1 and PD-L2 proteins could effectively bind coated human PD-1 protein, and the addition of different concentrations of PD1-H944 and Nivolumab both effectively inhibited the binding of recombinant human PD-L1 protein (FIG. 7A) and recombinant human PD-L2 protein (FIG. 7B) to human PD-1. PD1-H944 and Nivolumab inhibited recombinant human PD-L1 at $IC_{50}$ of 0.116 μg/mL ($R^2$=0.995) and 0.129 μg/mL ($R^2$=0.997), respectively, and recombinant human PD-L2 at $IC_{50}$ of 0.446 μg/mL ($R^2$=0.994) and 0.486 μg/mL ($R^2$=0.996), respectively. The ability of PD1-H944 to inhibit the binding of human PD-1 to human PD-L1 or human PD-L2 was not significantly different from that of Nivolumab, and no significant inhibition was observed for the negative control antibody.

Figure 8:
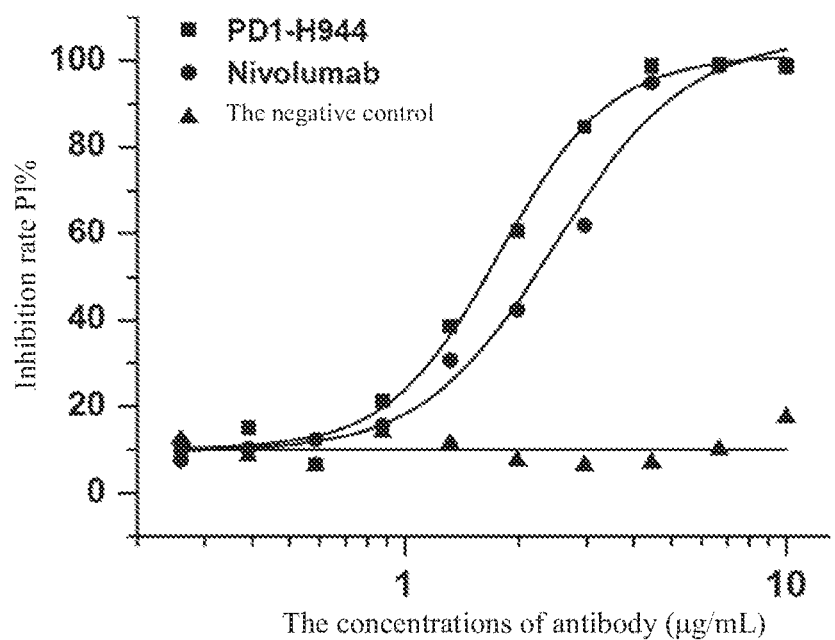
FIG. 8: FACS assay of the blocking on the binding of human PD-L1 to human Jurkat/PD-1 cells by PD1-H944.

4.3 PD1-H944 Blocks the Binding of Human PD-1 Ligand (PD-L1) to Human PD-1 Expressing Cells $5\times10^5$ cells/tube of recombinant human PD-1 stably expressing Jurkat/PD-1 cells in logarithmic growth phase were added with PD1-H944, Nivolumab and the negative control antibody H7N9-R1-IgG4 in different concentrations (0.260 μg/mL, 0.390 μg/mL, 0.585 μg/mL, 0.878 μg/mL, 1.317 μg/mL, 1.975 μg/mL, 2.963 μg/mL, 4.444 μg/mL, 6.667 μg/mL or 10.000 μg/mL) and incubated at 4° C. Add 10 μL of 0.4 μg/mL of B7H1-Fc-Biotin (Sino Biological, Inc.), wash with PBS and remove unbound antibody by centrifugation. Streptavidin Alexa Fluor® 488 Conjugate (Life Technologies) was added, incubated at 4° C. for 20 minutes, repeated washed and centrifuged, and 200 μL of PBS was added to re-suspend the cells for detection on a flow cytometer. The results showed that the recombinant human PD-L1 protein could effectively bind to Jurkat/PD-1 cells, and the binding of recombinant human PD-L1 protein to Jurkat/PD-1 cells was effectively inhibited when different concentrations of PD1-H944 and Nivolumab were added (FIG. 8). The inhibitory concentrations $IC_{50}$ were 1.78 μg/mL ($R^2$=0.994) and 2.48 μg/mL ($R^2$=0.989), respectively. PD1-H944 inhibited the binding of human PD-1 and human PD-L1 slightly better than Nivolumab, and no significant inhibition was observed for the negative control antibody.

4.4 Binding of PD1-H944 to CD16a

The affinity receptor CD16a (FcγRIIIa) protein is the major Fc receptor mediating the effects of ADCC wherein a CD16a containing the V158 SNP site has a relatively high affinity. The binding of PD1-H944 to the recombinant CD16a (V158) protein was measured by ELISA to assess the potentiality of PD1-H944 in regard to antibody dependent cell-mediated cytotoxicity (ADCC) effects.

The positive control PD1-H944-1-IgG1 (o) used in this assay is the variable region of PD1-H944 linked to natural IgG1, and the negative control PD1-H944-1-IgG1 is the variable region of PD1-H944 linked to N297A mutant IgG1 whose Fc fragment is deprived of the ability to bind to CD16a due to N-glycoside deletion. Recombinant human PD-1 protein (10 μg/mL, 100 μL/well) was coated on 96-well plates overnight at 4° C., washed the next day and blocked at room temperature for 1 h. PD1-H944, Nivolumab, positive control antibody PD1-H944-1-IgG1 (o)(Sino Biological, Inc.) and the negative control antibody PD1-H944-1-IgG1 (Sino Biological, Inc.) at different concentrations (0.020 μg/mL, 0.078 μg/mL, 0.3125 μg/mL, 1.25 μg/mL, 5 μg/mL, 20 μg/mL and 80 μg/mL) were added (see FIG. 9), and the plates were washed to remove unbound antibody after incubation. 10 μg/mL of recombinant CD16a-AVI-His (V158)+BirA protein (Sino Biological, Inc.) was added to the wells after incubation with 1 μg/mL of streptavidin/HRP, and $OD_{450}$ was detected by color development after incubation.

Figure 9:
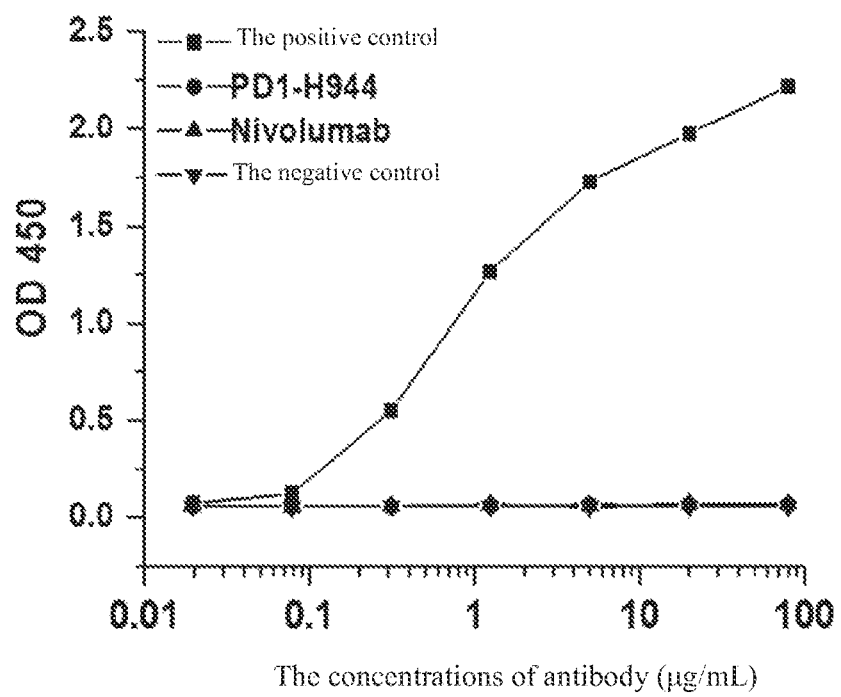
FIG. 9: ELISA of the binding of PD1-H944 to recombinant CD16a protein.

The results showed that binding of the positive control antibody to recombinant CD16a protein increased with antibody concentration. PD1-H944, Nivolumab and the negative control antibody did not bind to recombinant CD16a protein at any of the tested concentrations (FIG. 9). This suggests that both PD1-H944 constructed as IgG4 subtype antibodies, and Nivolumab have a very low ability to bind CD16a, predicting that PD1-H944 has no or very low ADCC effect.

4.5 Binding of PD1-H944 to C1q

The binding of PD1-H944 to recombinant C1q protein was measured by ELISA, thereby assessing the potentiality of PD1-H944 of complement-dependent cytotoxicity (CDC) effects.

PD1-H944-1-IgG1 (o), obtained by linking the variable region of PD1-H944 to natural IgG1, was used as the positive control antibody (Sino Biological, Inc.) and H7N9-R1-IgG4 (Sino Biological, Inc.) was used as the isotype control antibody. Different concentrations (20 μg/mL, 10 μg/mL, 5 μg/mL, 2.5 μg/mL, 1.25 μg/mL, 0.625 μg/mL, 0.313 μg/mL, 0.156 μg/mL and 0.078 μg/mL) (see FIG. 10) of PD1-H944, Nivolumab, positive control antibody and isotype control antibody were coated on 96-well plates at 100 μL per well overnight at 4° C. The next day, the plates were washed, blocked at room temperature for 1 hour, and 100 μL of 5 μg/mL of recombinant C1q protein (Quidel Corporation) was added respectively and the plates were incubated for 3 hours. 100 μL of secondary antibody anti-C1q/HRP (Abcam) at 1:400 dilution fold, was added, incubated for 1 hour, developed color and detected $OD_{450}$.

Figure 10:
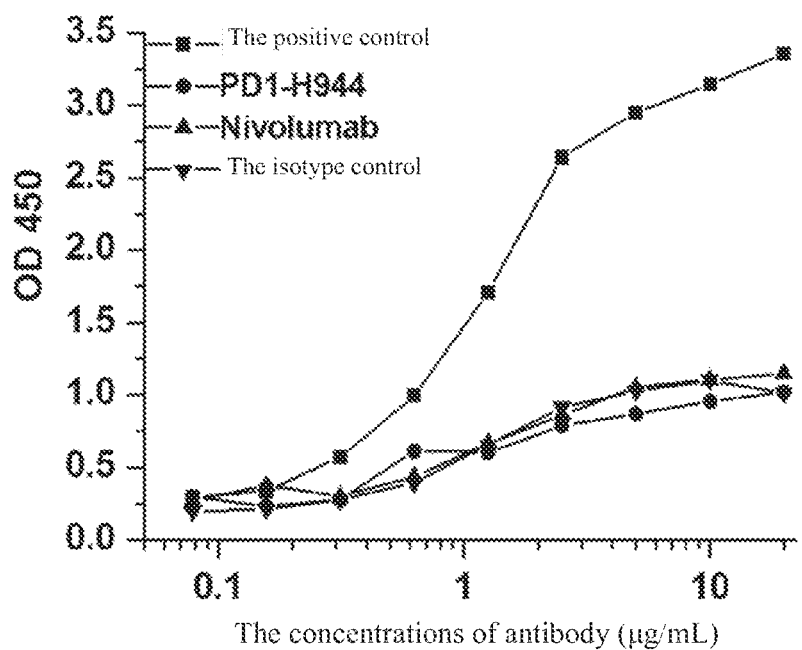
FIG. 10: ELISA of the binding of PD1-H944 to recombinant C1q protein.

The results showed that binding of positive control antibodies to recombinant C1q protein increased with antibody concentration. PD1-H944, Nivolumab and isotype control antibodies had comparable binding capacity to recombinant C1q protein, with significantly lower binding capacity than IgG1-type positive controls (FIG. 10).

4.6 Binding of PD1-H944 to FcRn

The binding of PD1-H944 to recombinant human Fc receptor (FcRn) protein was measured by ELISA and thus the pharmacokinetics of PD1-H944 in humans was assessed.

Anti-biotin protein Avidin (Thermo Fisher Scientific) at a concentration of 10 μg/mL was coated onto 96-well plates at 100 μL per well and incubated overnight at 4° C. and washed the next day, blocked at room temperature for 1 hour and incubated with 10 μg/mL of biotinylated FCGRT-His+B2M protein (Sino Biological, Inc.) for 1 hour, then PD1-H944, Nivolumab or isotype control antibody H7N9-R1-IgG4 (Sino Biological, Inc.) in different concentrations (0.123 μg/mL, 0.37 μg/mL, 1.11 μg/mL, 3.33 μg/mL, 10 μg/mL, 30 μg/mL, 90 μg/mL, 270 μg/mL) was added respectively (see FIG. 11), incubated for 1 h, washed and 250 ng/mL of goat anti-human IgG Fc/HRP (Sino Biological Inc.) was added. The process from antibody dilution to secondary antibody incubation was maintained at pH 6.0, and $OD_{450}$ was measured.

Figure 11:
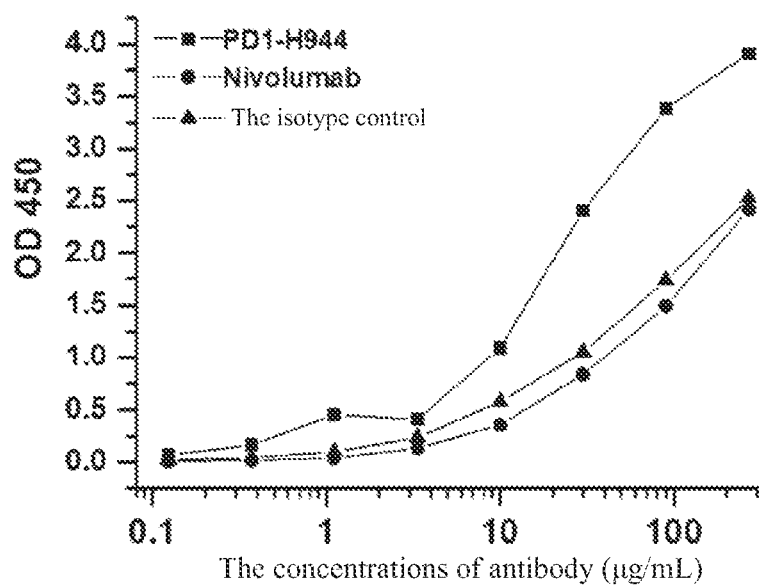
FIG. 11: ELISA of the binding of PD1-H944 to human FcRn protein.

The results showed that PD1-H944 and Nivolumab were able to bind to recombinant human FcRn protein, and the binding capacity increased with concentration; at high concentrations (270 μg/mL), the binding of PD1-H944 to recombinant human FcRn protein was approximately 1.62 times of that of Nivolumab (FIG. 11). Based on this result, it is hypothesized that PD1-H944 has good pharmacokinetics in humans.

Example 5: Function Analysis of the Humanized Antibody PD1-H944

5.1 Activation of CD4$^+$ T Cells in Mixed Lymphoid Responses Stimulated by PD1-H944

The neutralizing activity of anti-human PD-1 antibody was detected by the mixing assay of CD4$^+$ T lymphocytes with DCs. Human peripheral blood mononuclear cells (PBMCs) were isolated by Ficoll density gradient centrifugation, and then mononuclear cells were obtained by the adhesion culture method, 1640 cell culture medium (GIBCO) (containing 10% FBS, 100 units/mL penicillin, 100 μg/mL streptomycin) containing 160 ng/mL rhIL-4 (Sino Biological, Inc.) and 20 ng/mL rhGM-CSF (R&D Systems) was added to the resulting mononuclear cells and incubated in a CO$_2$ incubator until the third day, then a half volume of culture medium was changed. After 6 days of incubation, the suspending cells were collected, which are known as DCs. The density of DCs was adjusted to 2×10$^6$ cells/mL, mitomycin at a final concentration of 50 μg/mL was added, treated at 37° C. for 20 minutes, washed three times with the 1640 medium for further steps. CD4$^+$ T lymphocytes were sorted from PBMC isolated from the peripheral blood of another person using a CD4$^+$ T lymphocyte sorting kit (MiltenyiBiotec). CD4$^+$ T lymphocytes from each of the three blood donors were used in each of batches of this assay. The sorted CD4$^+$ T lymphocytes were mixed with DCs previously treated with 50 μg/mL mitomycin in a 10:1 ratio, and 10$^5$ cell/well were evenly inoculated in 96-well plates with PD1-H944, Nivolumab, and the negative control antibody H7N9-R1-IgG4 (Sino Biological, Inc.), respectively, and another mixed lymphocyte control group, i.e. the group with only CD4$^+$ T lymphocytes and DCs mixture without antibody, DC cells control group, i.e. the group with only DC cells without antibody and CD4$^+$ T lymphocytes, CD4$^+$ T cells control group, i.e. the group with only CD4$^+$ T cells without antibody and DCs cells, with the same volume of sample diluent 1640 medium, the final concentration gradient of each antibody was 1 μg/mL, 0.1 μg/mL, 0.01 μg/mL, and incubated in a CO$_2$ incubator at 37° C. and 5% CO$_2$ for 5 days. The culture supernatants were collected and the expression levels of IL-2 and IFN-γ in the culture supernatants were measured by ELISA.

Figure 12:
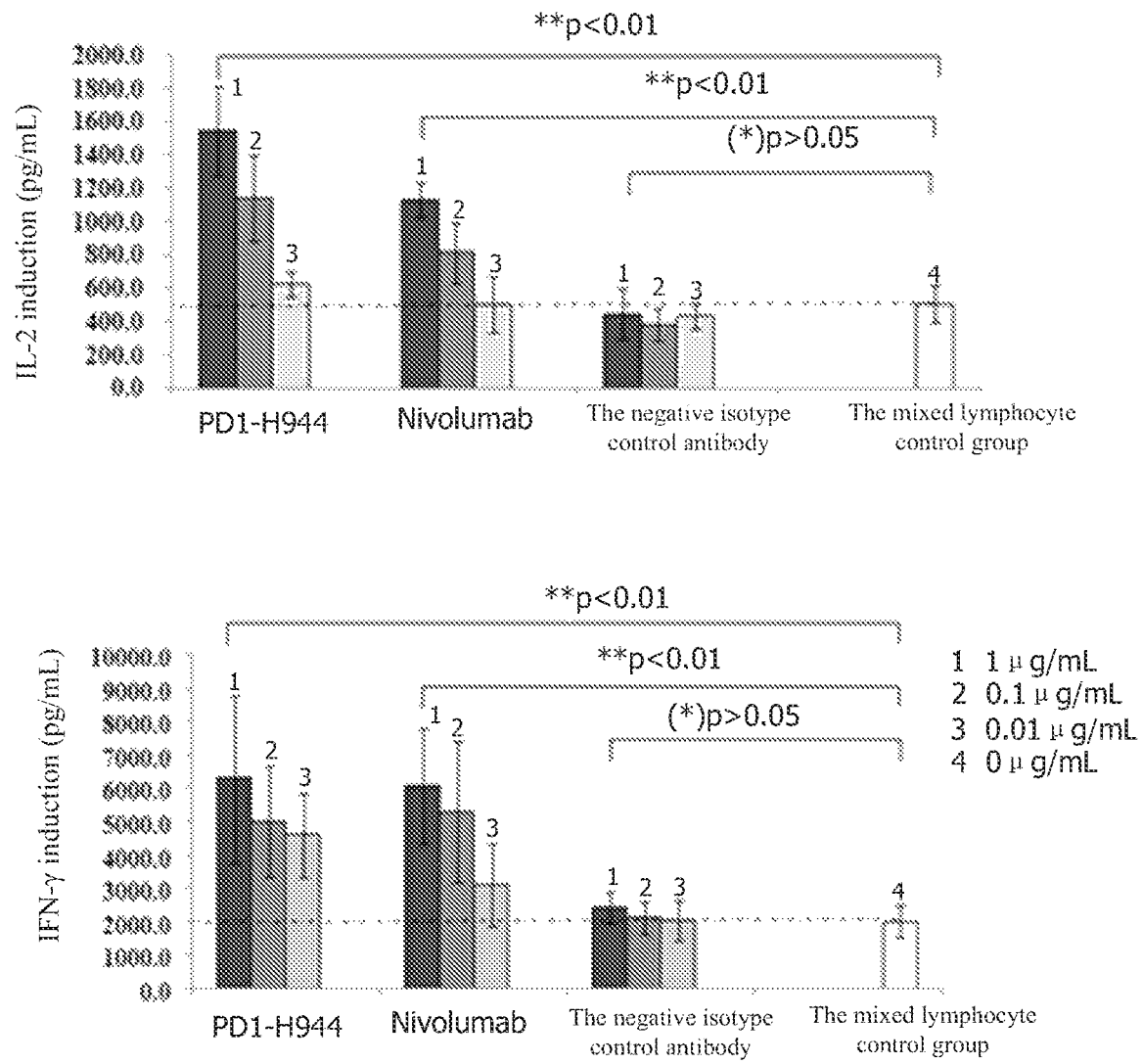
FIG. 12A: Promoted IL-2 (top) and IFN-γ (bottom) secretion in a mixed lymph assay (A are CD4$^+$ T cells from 3 donors) by PD-1 antibody.
FIG. 12B: Promoted IL-2 (top) and IFN-γ (bottom) secretion in a mixed lymph assay (B are CD4$^+$ T cells from 3 donors) by PD-1 antibody.
FIG. 12C: Promoted IL-2 (top) and IFN-γ (bottom) secretion in a mixed lymph assay (C are CD4$^+$ T cells from 3 donors) by PD-1 antibody.
Figure 12:
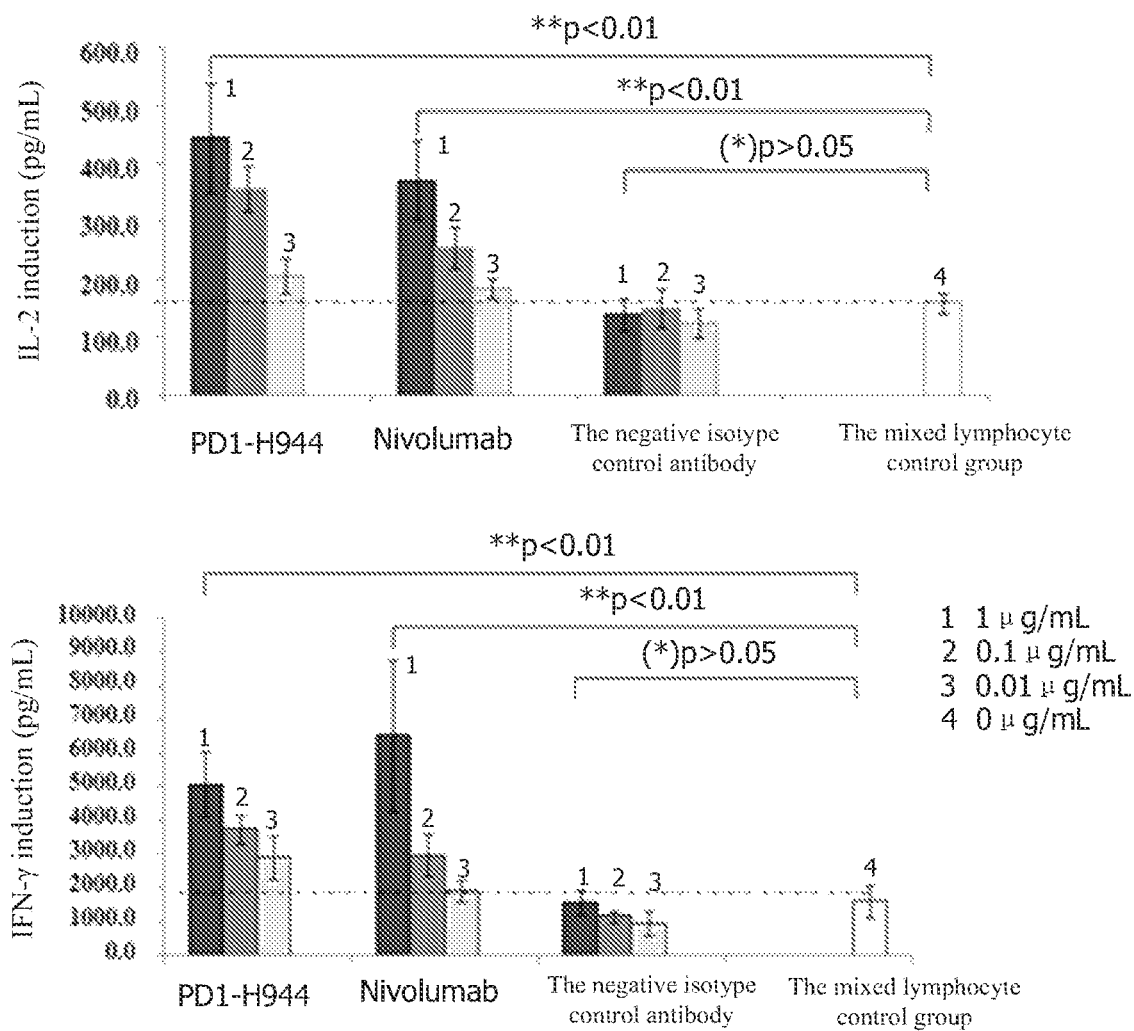
Figure 12:
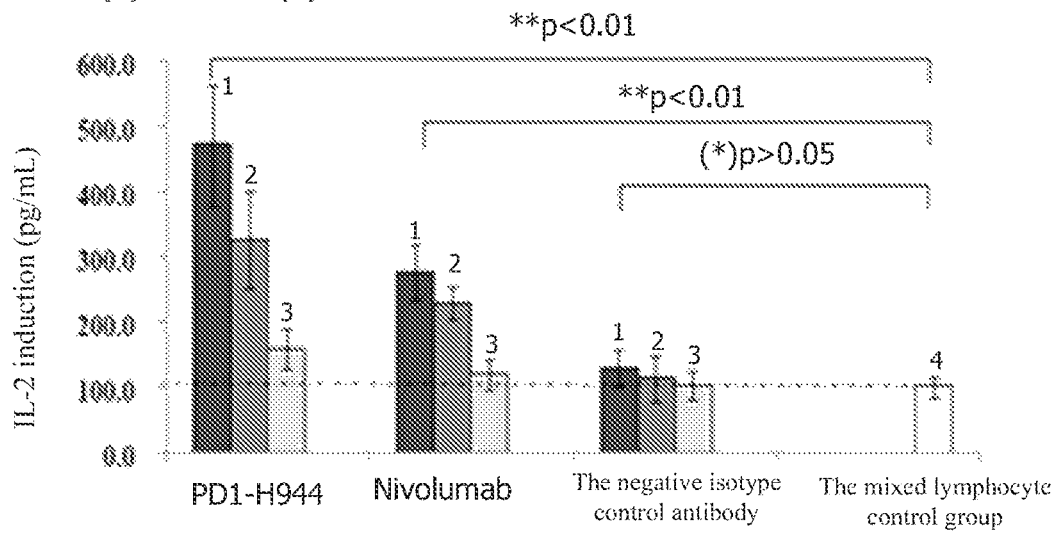
Figure 12:
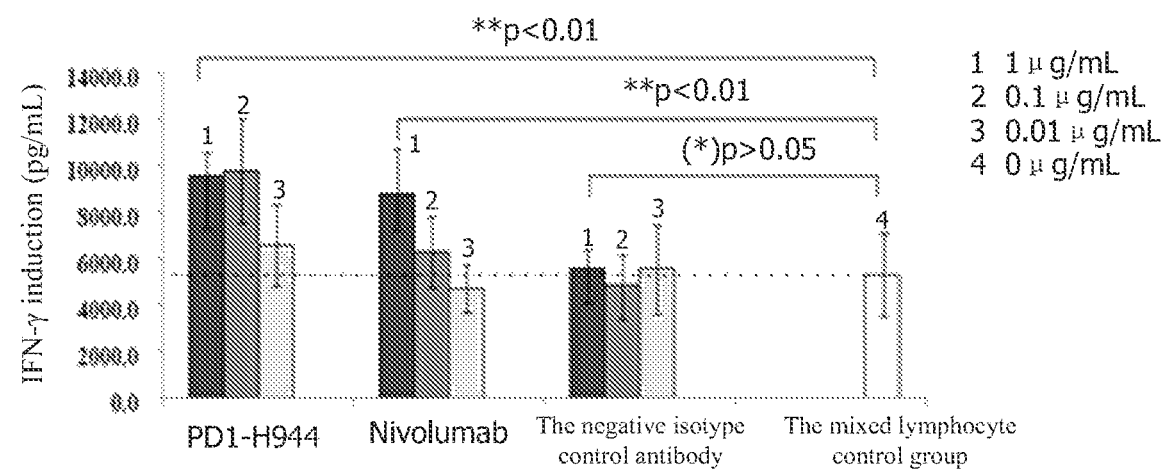

The results showed that IFN-γ and IL-2 secretion could not be detected in the supernatants of CD4$^+$ T cell cultures without DCs mixing, while in the mixed lymphocyte control group, the mixing of CD4$^+$ T cells and DCs significantly increased the IFN-γ and IL-2 secretion of CD4$^+$ T cells. When anti-PD-1 antibody was added to the mixed lymphocyte system, the activation of CD4$^+$ T cells in the mixed lymphatic response of CD4$^+$ T and DCs significantly promoted with higher IFN-γ and IL-2 secretion. Rather contrary to both PD1-H944 and Nivolumab, which had a significant effect, the negative control antibody did not show this effect. The results are shown in FIGS. 12A-12C, suggesting that PD1-H944 has better functional activity than that of Nivolumab and can effectively reactivate immunosuppressed T cells.

5.2 PD1-H944 Stimulates the Activation of Reporter Genes in the IL2 Signalling Pathway Downstream of PD1

In this assay, effector cells Jurkat-NFAT-Luc2p-PD-1 (SinoCellTech Ltd) and target cells CHO-K1-PD-L1-CD3E (SinoCellTech Ltd) were used as experiment materials. The PD-1/PD-L1 interaction resulted by co-culture of these two cells inhibits TCR signaling and NFAT-RE-mediated bioluminescence, and the addition of PD-1 antibody blocked the PD-1/PD-L1 interaction and thus released this inhibition. The activation function of PD1-H944 in the recombinant human PD-1 reporter cell system was determined by measuring the intensity of bioluminescence (RLU) in effector cells. Target cells CHO-K1-PD-L1-CD3E cells were inoculated at 2×10$^4$/well in 96-well plates and cultured overnight in DMEM medium containing 10% FBS, then the supernatant was removed. PD1-H944, Nivolumab and the negative control antibody H7N9-R1-IgG4 (Sino Biological, Inc.) in different concentrations (0.007 μg/mL, 0.023 μg/mL, 0.082 μg/mL, 0.286 μg/mL, 1.000 μg/mL, 3.499 μg/mL, 12.245 μg/mL, 42.857 μg/mL, 150 μg/mL) were added at 40 μL/well (see FIG. 13). 7.5×10$^4$ effector cells Jurkat-NFAT-Luc2p-PD-1 were subsequently added at 40 μL/well and incubated in a CO$_2$ incubator for 6 hours. Each assay was performed in triplet on target cells, effector cells and negative control M. After 6 hr incubation, passive lysis 5X buffer (Promega) was added at 20 μL/well and the 96-well plate was then placed in a −80° C. frigerator for further detection. For the assay, the 96-well plates placed in the −80° C. Thawed to room temperature, being shaken and 20 μL of supernatant per well was transferred to a 96-well white bottom plate for luminescence detection by the LB960-Microplate Luminol Assay.

Figure 13:
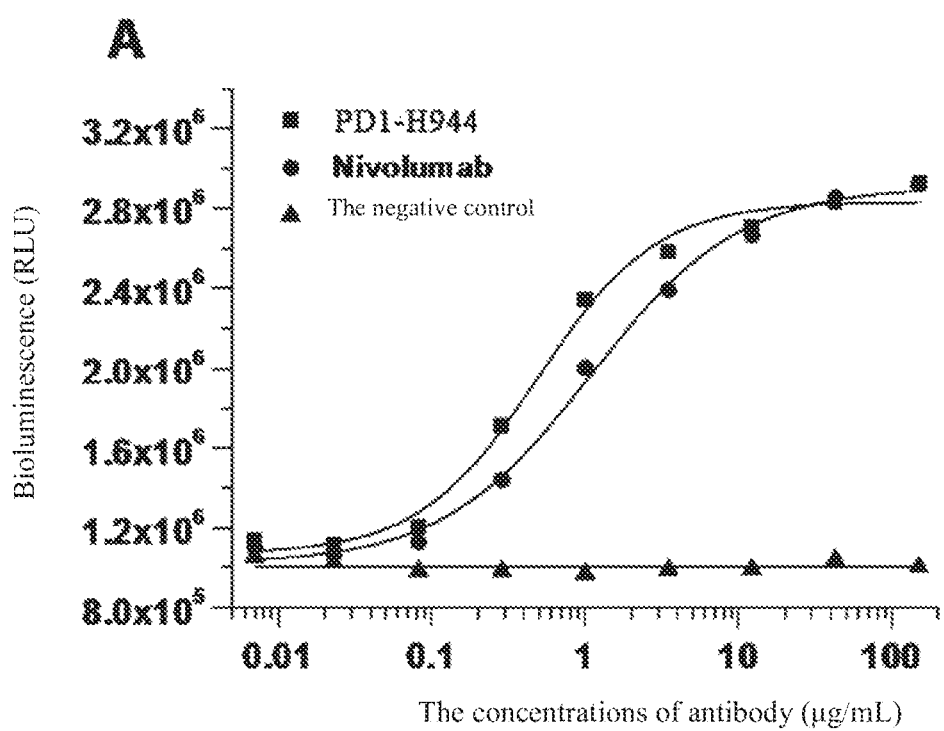
FIG. 13: Activation function of PD1-H944 in a recombinant human PD-1 reporter gene cell system.

The results showed that both PD1-H944 and the control antibody Nivolumab had a significant activation of the recombinant human PD-1 reporter gene cell system, as shown in FIG. 13. In the concentration range of 0.007-150 μg/mL, the EC$_{50}$ f of PD1-H944 was 0.49 μg/mL and that of Nivolumab was 1.08 μg/mL. PD1-H944 had an EC$_{50}$ significantly lower than that of Nivolumab, its activity is 2.21 times of that of Nivolumab. The negative control antibody had no activating function in the recombinant human PD-1 reporter gene cell system.

5.3 PD1-H944 does not Significantly Stimulate the ADCC Function of the Fc Receptor CD16a Pathway In this assay, the effector cell Jurkat-NFAT-Luc2p-CD16A (SinoCellTech Ltd) and the target cell CHO-PD-1 (SinoCellTech Ltd) were used as assay materials to measure the PD1-H944-mediated ADCC effect by the recombinant highly active CD16a (V158) reporter gene system method. The mechanism is that when two cells are co-cultured and PD1-H944 is added simultaneously, the Fab fragment of PD1-H944 binds to PD-1 overexpressed target cells, thus make its Fc fragment bind to effector cells carrying Fcγ receptor CD16A, consequently activates effector cells Jurkat-NFAT-Luc2p-CD16A and promoting NFAT-RE-mediated chemiluminescence. Target CHO-PD-1 cells were inoculated at 2×10$^4$/well in a 96-well plate and cultured overnight in DMEM medium containing 10% FBS, and the supernatant was removed. The plates were washed twice with RPMI 1640 (phenol red-free) medium containing 0.1% BSA, and then positive control antibody PD1-H944-1-IgG1 (o), PD1-H944, Nivolumab and negative control antibody H7N9-R1-IgG4 (Sino Biological, Inc.) were added at different concentrations (see FIGS. 14A-B) at 40 μL/well, 1×10$^6$ effector cells Jurkat-NFAT-Luc2p-CD16A at 40 μL/well were added, and placed in a CO$_2$ incubator at 37° C. and 5% CO$_2$ for 4 hours. Each assay was performed in triplet on target cells, effector cells and negative control. At the end of 4 hrs, 20 μL/well of passive lysis 5X buffer (Promega) was added and the 96-well plate was placed in a −80° C. refrigerator for testing. For the assay, the 96-well plates were thawed to room temperature, shaken and 20 μL of supernatant per well was transferred to a 96-well white plate for luminescence detection by the LB960-Microplate Luminal Assay.

Figure 14:
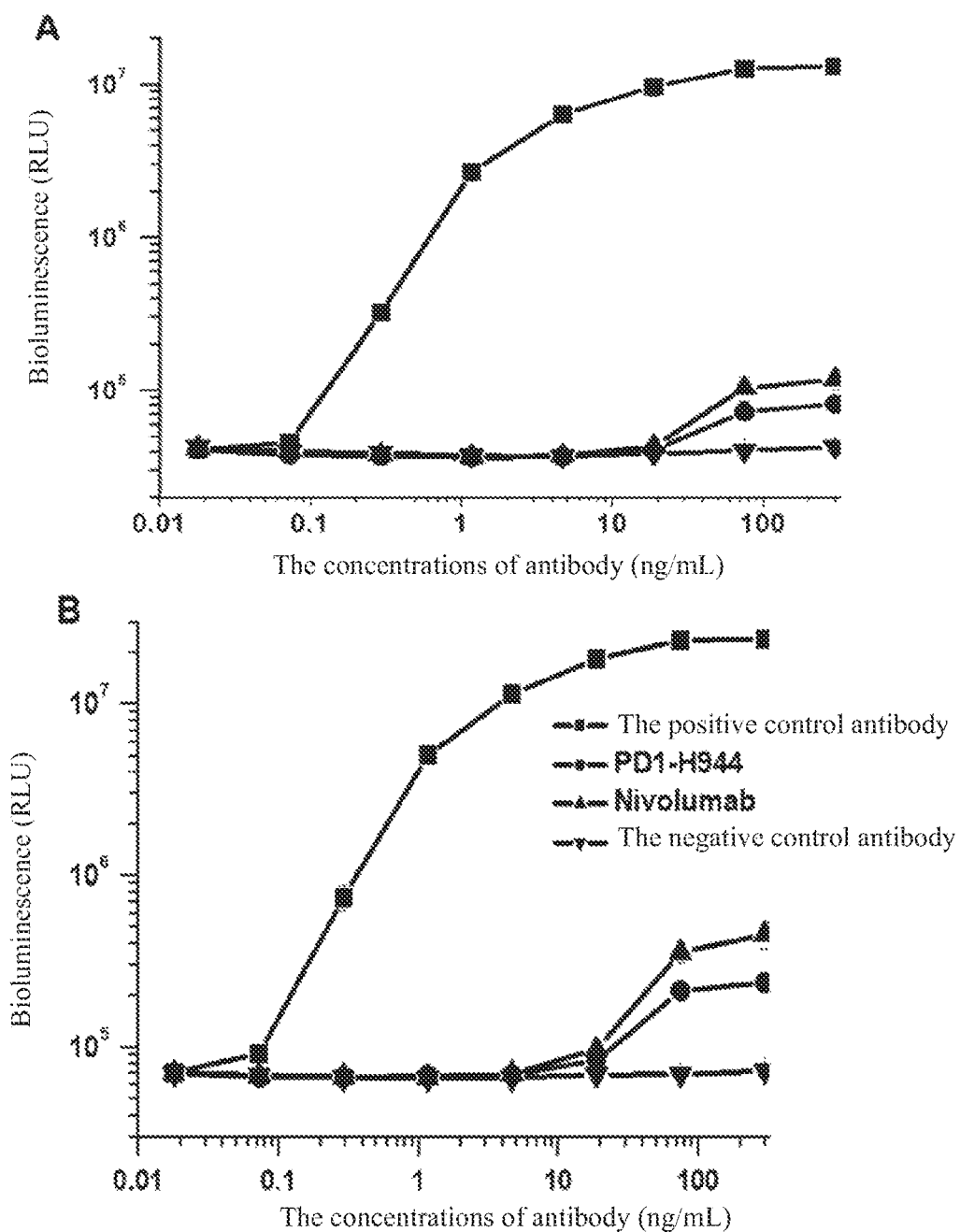
FIG. 14A: ADCC function of PD1-H944 detected by the recombinant CD16a reporter gene system (A includes the results of different assay batches; ** indicates P<0.01).
FIG. 14B: ADCC function of PD1-H944 detected by the recombinant CD16a reporter gene system (B includes the results of different assay batches; ** indicates P<0.01).
FIG. 14C: ADCC function of PD1-H944 detected by the recombinant CD16a reporter gene system (C includes the bioluminescence intensity values at the highest antibody concentration; ** indicates P<0.01).
FIG. 14D: ADCC function of PD1-H944 detected by the recombinant CD16a reporter gene system (D includes the bioluminescence intensity values at the highest antibody concentration; ** indicates P<0.01).
Figure 14:
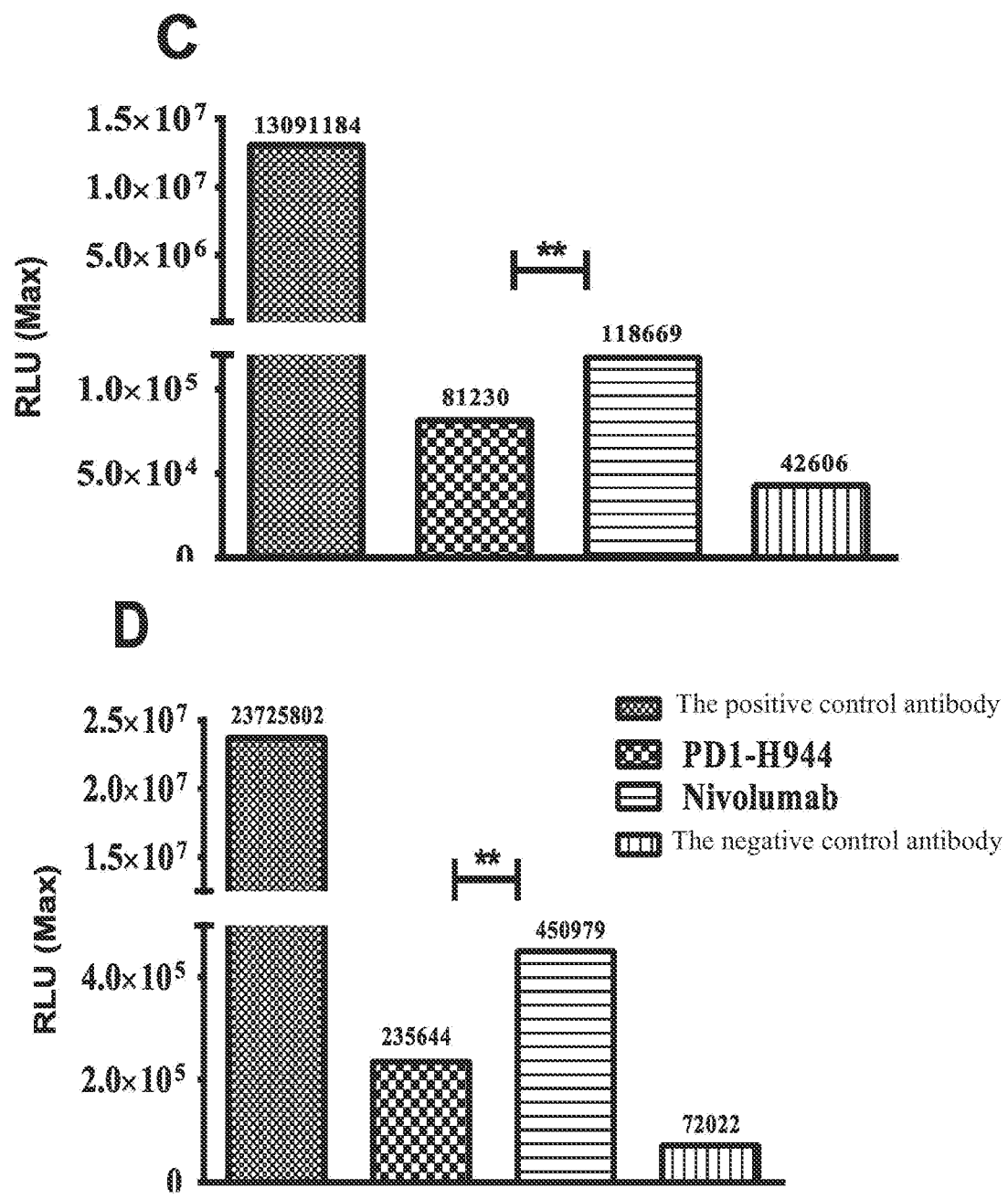

The results showed that the positive control antibody PD1-H944-1-IgG1 (o) had a significant ADCC mediating effect, Nivolumab had a weaker ADCC effect while PD1-H944 had an even weaker ADCC effect than Nivolumab in the concentration range of 0.018-300 ng/mL (p<0.01). FIG. 14A and FIG. 14B show the results of different batches of assays. FIGS. 14C and 14D indicate the bioluminescence intensity (RLU) corresponding to the highest antibody concentration point (300 ng/mL) in A and B, respectively. In this sensitive ADCC functional assay, the cellular activation triggered by PD1-H944 binding to CD16a was significantly lower than that of Nivolumab and the results were repeatable. The low ADCC activity of the PD1-H944 drug is a good support for the efficacy and safety of this antibody in the clinic.

5.4 PD1-H944 does not Significantly Activate the CDC Function of the Complement C1q Pathway After its binding to PD-1 overexpressed tumor cells, PD1-H944 could activate the classical complement pathway to kill tumor cells, leading to the death thereof. In this assay, the CDC effect of PD1-H944 was investigated using the WST-8 method. CHO-PD-1 cells were re-suspended in RPMI 1640 medium containing 0.1% BSA (SinoCellTech Ltd) and inoculated uniformly in 96-well plates at $5 \times 10^4$/well, followed by the addition of antibodies at different concentrations (FIG. 15) at 50 μL/well and then complement C1q at a 1:4 dilution at 50 μL/well (One lambda). The antibodies were the positive control antibody PD1-H944-1-IgG1 (o) (Sino Biological, Inc.), PD1-H944, Nivolumab and the negative control antibody PD1-H944-1-IgG1 (Sino Biological, Inc.), with assay blank well B (no cells) and negative control M (with cells but no antibody). After incubation for 3 hours at 37° C., 15 μL of WST-8 color development solution was added to each well and the absorbance was measured at 450 nm and 630 nm on ELISA Analyzer after the color development was stabilized. Results were calculated using absorbance values $OD_{450}$-$OD_{630}$ with the value of blank well subtracted. % kill=(OD of negative control M−OD of sample)/OD of negative control M×100%.

Figure 15:
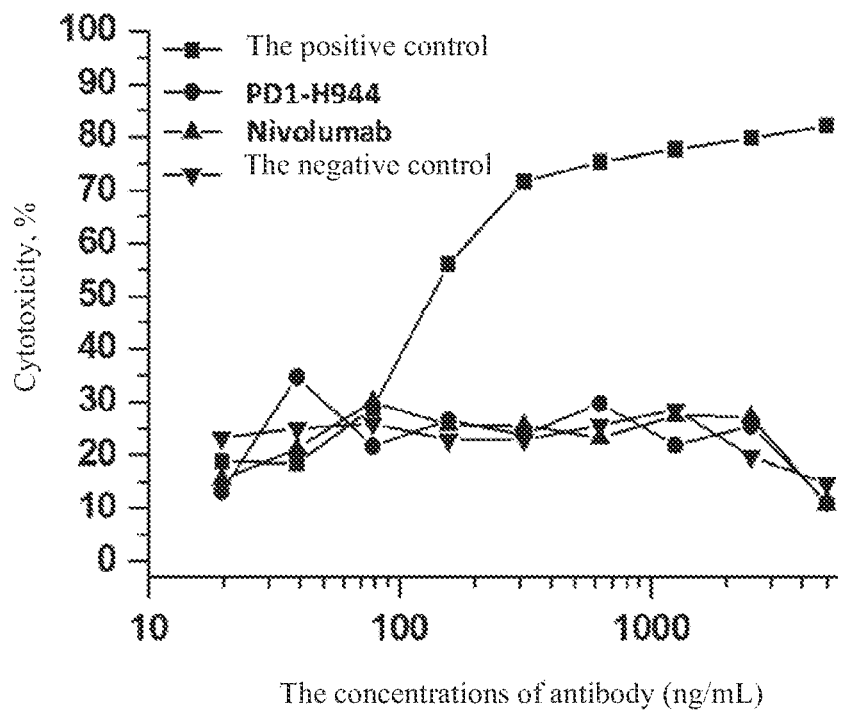
FIG. 15: CDC effect of PD1-H944 on CHO-PD-1 cells.

The results showed that PD1-H944, Nivolumab and the negative control antibody had no CDC effect on CHO-PD-1, a tumor cell overexpressing PD-1, while the positive control antibody had killing effect on CHO-PD-1 with a maximum killing rate of 82.1%, the results are shown in FIG. 15. CDC assay also confirmed that PD1-H944 had no CDC effect on PD-1-expressing target cells demonstrating the antibody's good safety.

5.5 PD1-H944 Effectively Inhibits the Growth of MC38 Colon Cancer Subcutaneous Transplant Tumor Model in Humanized PD-1 Mice In Vivo (1) Pharmacodynamics Study I of PD1-H944 in a Humanized PD-1 Mouse Model with MC38 Colon Cancer Subcutaneous Transplantation Tumor MC38 cells at logarithmic growth stage (Sun Ran Shanghai Biotechnology Co., Ltd.) were used for tumor inoculation. MC38 cells re-suspended in PBS were inoculated at $5 \times 10^5$ cells/0.1 mL in B-hPD-1 humanized mice (Biocytogen) (obtained by replacing part of exon 2 of the PD-1 gene of C57BL/6 mice with the corresponding part of the human PD-1 genome) subcutaneously on the right side of the lateral thorax of mice, 47 mice in total. When the tumor volume grew into about 100 mm$^3$, the mice were elected according to their individual tumor volume, randomly assigned to 5 groups using excel software, 8 animals in each group. Groups 4 and 5 were administered with other anti-PD-1 antibodies irrelevant to this application, so their data are not presented herein. Dosing was started on the day of grouping. The mice were administered by intraperitoneal injection (I.P.), once every 3 days for 6 consecutive doses, executed 10 days after the last dose and tumor tissue were removed for weighing. The specific dosing regimen was shown in Table 3 below. Anti-tumor effect of the drug was evaluated by calculating the tumor growth inhibition rate TGI (%). TGI (%)<60% was considered ineffective; TGI (%)≥60% and the tumor volume of the treated group was statistically significantly lower than that of the solvent control group (P<0.05) was considered effective, i.e. it had a significant inhibitory effect on tumor growth. the TGI (%) was calculated as follows.

TGI(%)=[1−(Ti−T0)/(Vi−V0)]×100, where

Ti: the mean tumor volume in the treatment group on day i.

T0: the mean tumor volume in the treatment group on day 0.

Vi: the mean tumor volume of the solvent control group on day i.

V0: mean tumor volume of the solvent control group on day 0.

The animals were executed at the end of the assay, weighed for tumor weight and the tumor weight inhibition rate $IR_{TW}$% was calculated, with $IR_{TW}$%>60% as the reference index of effectiveness, calculated as follows.

Inhibition rate of Tumor weight $IR_{TW}$(%)=($W$ solvent control−$W$ treatment group)/$W$ solvent control×100, $W$ is tumor weight.

TABLE 3

Groups and dosing regimens

| Group | No of animals | Drugs | Dose (mg/kg)$^a$ | Route of administration | Treatment schedule |
|---|---|---|---|---|---|
| 1 | 8 | Solvent control | — | I.P. | Q3d × 6 |
| 2 | 8 | Nivolumab | 20 | I.P. | Q3d × 6 |
| 3 | 8 | PD1-H944 | 20 | I.P. | Q3d × 6 |

Note:
$^a$The volume of administration is calculated at 10 μL/based on the body weight of the tested animal.

Figure 16:
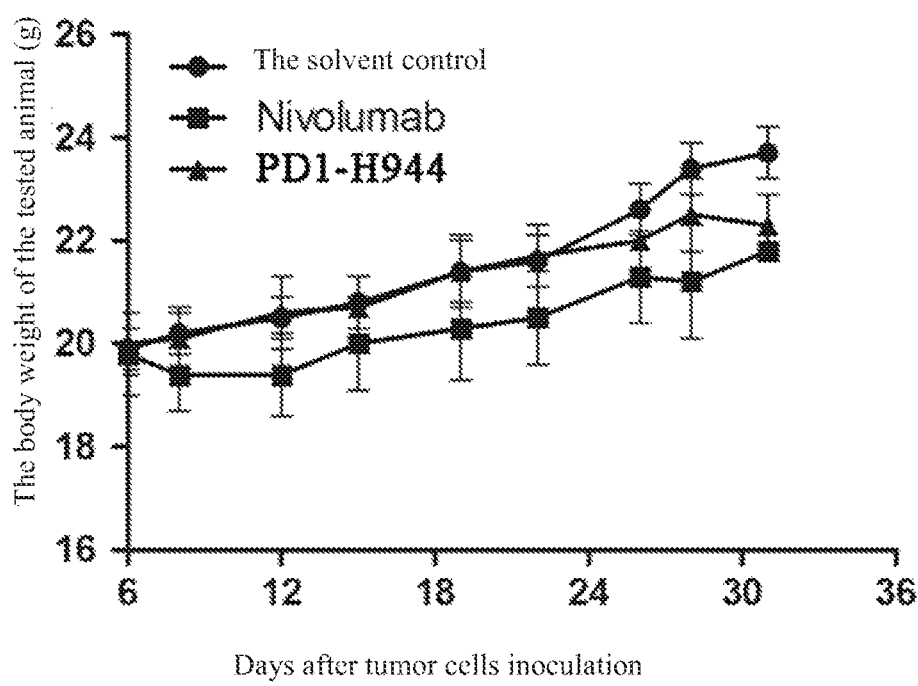
FIG. 16: Trend of changes in animal body weight after administration.

All test animals were in good general condition in terms of activity and feeding during the dosing period, and their body weight increased to some extent. There was no significant difference (P>0.05) in the body weight of the animals after the administration of the test drug (group 3) and the control drug (group 2). The changes in body weight of all animals are shown in FIG. 16 and Table 4.

TABLE 4

Effect of PD1-H944 on body weight in MC38 colon cancer transplanted B-hPD-1 humanized mice

| Group | No. of animals [c] | Body weight (g)[a] Before administration | Body weight (g)[a] 25 days after first dose | P[b] | Weight change after 25 days of administration (g) |
|---|---|---|---|---|---|
| Group 1: Solvent control | 8 | 19.9 ± 0.4 | 23.7 ± 0.5 | — | +3.8 |
| Group 2: Nivolumab 20 mg/kg | 8 | 19.8 ± 0.8 | 21.8 ± 1.1 | 0.105 | +2.0 |
| Group 3: PD1-H944 20 mg/kg | 8 | 20.0 ± 0.6 | 22.3 ± 0.6 | 0.074 | +2.3 |

[a] mean ± standard error.
[b] statistical comparison of body weight in the treatment group with that of the solvent control group 25 days after administration, t-test.
[c] Group 2 had 7 mice at end of the experiment.

Figure 17:
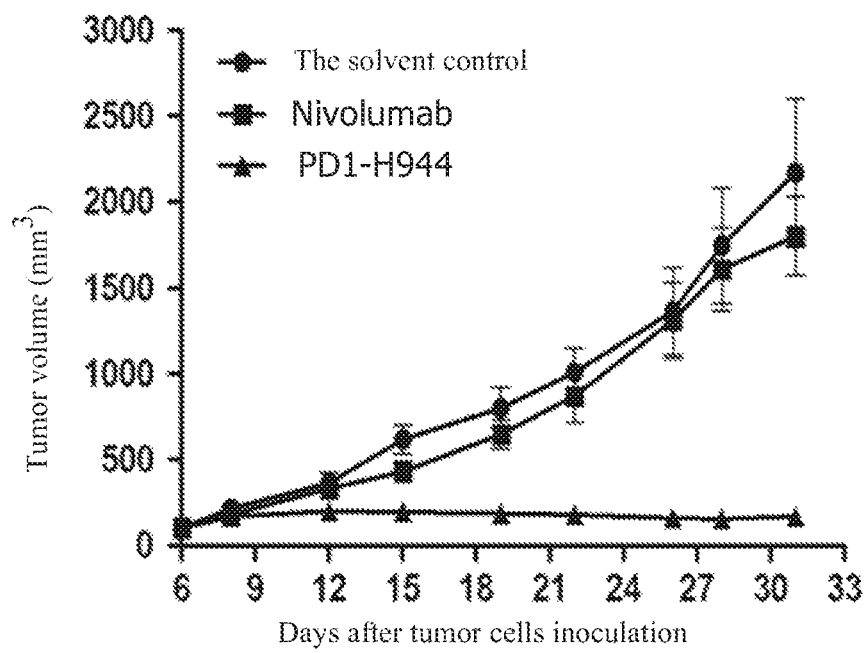
FIG. 17: Trend of tumor volume growth after administration.

The tumor volume results for each group in the trial are shown in Table 5 and FIG. 17.

TABLE 5

Effect of PD1-H944 on tumor volume in MC38 colon cancer transplanted B-hPD-1 humanized mice

| Days | Solvent control Tumor volume (mm³) | Nivolumab Tumor volume (mm³) | Nivolumab TGI (%) | PD1-H944 Tumor volume (mm³) | PD1-H944 TGI (%) |
|---|---|---|---|---|---|
| 6 | 104 ± 7 | 104 ± 7 | / | 103 ± 7 | / |
| 8 | 215 ± 23 | 181 ± 21 | 30.4 | 170 ± 19 | 39.5 |
| 12 | 367 ± 59 | 333 ± 39 | 13.0 | 202 ± 26*$^{\Psi\Psi}$ | 62.3 |
| 15 | 618 ± 84 | 432 ± 58 | 36.1 | 195 ± 33**$^{\Psi\Psi}$ | 82.2 |
| 19 | 802 ± 118 | 648 ± 85 | 22.0 | 189 ± 40**$^{\Psi\Psi}$ | 87.7 |
| 22 | 1009 ± 143 | 870 ± 152 | 15.4 | 182 ± 40**$^{\Psi\Psi}$ | 91.3 |
| 26 | 1363 ± 252 | 1310 ± 221 | 4.3 | 162 ± 47**$^{\Psi\Psi}$ | 95.3 |
| 28 | 1745 ± 339 | 1608 ± 240 | 8.3 | 156 ± 45**$^{\Psi\Psi}$ | 96.8 |
| 31 | 2171 ± 430 | 1802 ± 228 | 17.8 | 171 ± 51**$^{\Psi\Psi}$ | 96.7 |

Figure 18:
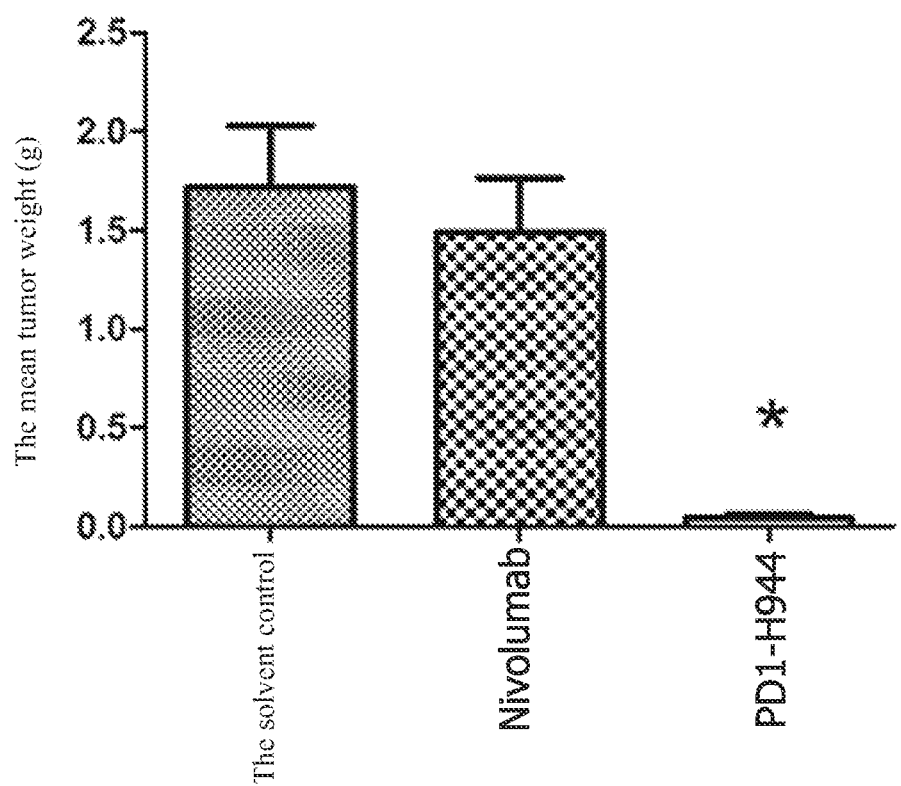
FIG. 18: Tumor weight plot at the end of the assay (*P<0.05).

Note:
*$P < 0.05$,
**$P < 0.01$ compared to solvent control;
$P^{\Psi} < 0.05$,
$P^{\Psi\Psi} < 0.01$ compared to Nivolumab group.
Days: Number of days after cell inoculation 25 days after the first dose, all animals were euthanized and the tumors were stripped, weighed and photographed. Tumor weights were statistically compared between groups and the results are summarized in Table 6 and FIG. 18.

TABLE 6

Effect of PD1-H944 on tumor weight in MC38 colon cancer transplanted B-hPD-1 humanized mice

| Group | No. of animals | Tumor weight (g) | Tumor weight inhibition rate IR$_{TW}$ (%) |
|---|---|---|---|
| Group 1: Solvent control | 8 | 1.719 ± 0.310 | — |
| Group 2: Nivolumab | 7 | 1.492 ± 0.274 | 13.2 |
| Group 3: PD1-H944 | 8 | 0.044 ± 0.017**$^{\Psi\Psi}$ | 97.4 |

Note:
*$P < 0.05$,
**$P < 0.01$ compared to solvent control;
$P^{\Psi} < 0.05$,
$P^{\Psi\Psi} < 0.01$ compared to Nivolumab group Consistent with the tumor volume results, Nivolumab did not significantly inhibit tumors in this model, while the mean tumor weight of the PD1-H944 group was 0.044±0.017 g. Its inhibition rate of tumor weight (IR$_{TW}$) reached 97.4%. Data analysis showed tumors of the PD1-H944 group were significantly different from that of solvent controls (P<0.05), demonstrating the significant anti-tumor efficacy of PD1-H944.

At the end of the assay, the mean tumor volume of the solvent control group was 2171±430 mm³ and the tumor weight was 1.719±0.310 g. The mean tumor volume of the positive control group Nivolumab (20 mg/kg) was 1802±228 mm³, the TGI % was 17.8% and the tumor weight was 1.492±0.274 g. The inhibition rate of tumor weight IR$_T$w was 13.2%, which was not significantly different from the tumor volume of the solvent control group (P=0.480). In contrast, the mean tumor volume of PD1-H944 was 171±51 mm³, TGI % was 96.7%, tumor weight was 0.044±0.017 g and inhibition rate of tumor weight IR$_{TW}$ was 97.4%, which was significantly different compared to the tumor volume of the solvent control (P<0.05), indicating that the donor antibody PD1-H944 bound to PD-1 epitope was effective and showed significant inhibition of MC38 colon cancer subcutaneous graft tumors at a dose level of 20 mg/kg.

(2) Pharmacodynamics Study II of PD1-H944 in a Humanized PD-1 Mouse with MC38 Colon Cancer Subcutaneous Transplantation Tumor MC38 cells at logarithmic growth stage (Sun Ran Shanghai Biotechnology Co., Ltd.) were used for tumor inoculation. MC38 cells re-suspended in PBS were inoculated at 5×10⁵ cells/0.1 mL in B-hPD-1 humanized mice (Biocytogen) (mice obtained by replacing part of exon 2 of the PD-1 gene of C57BL/6 mice with the corresponding part of the human PD-1 genome). A total of 80 mice were inoculated subcutaneously on the right side of the lateral thorax. When the tumor volume grew into about 100 mm³, the mice were elected according to their individual tumor volume, randomly assigned to 8 groups using excel software, 8 animals in each group. Groups 3, 4, 7 and 8 were administered with other anti-PD-1 antibodies irrelevant to this application, so their data were not presented herein. Dosing was started on the day of grouping. The mice were and administered by intraperitoneal injection (I.P.), once every 3 days for 6 consecutive doses, with mice executed 10 days after the last dose and tumor tissue removed for weighing. The specific dosing regimen is shown in Table 7 below.

TABLE 7

Trial groups and dosing

| Group | No. of animals | Drugs under test | Dose (mg/kg)[a] | Route of administration | Treatment schedule |
|---|---|---|---|---|---|
| 1 | 8 | Solvent control | — | I.P. | Q3d × 6 |
| 2 | 8 | Pembrolizumab[b] | 20 | I.P. | Q3d × 6 |
| 5 | 8 | PD1-H944 | 8 | I.P. | Q3d × 6 |
| 6 | 8 | PD1-H944 | 2 | I.P. | Q3d × 6 |

Note:
[a]The volume of administration was calculated based on the body weight of the animal at 10 μL/g;
[b]Pembrolizumab: Sino Biological, Inc.

The anti-tumor effect of the drug was evaluated by calculating the tumor growth inhibition rate TGI (%). TGI (%)<60% was considered ineffective; TGI (%)≥60% and the tumor volume of the treated group statistically lower than that of the solvent control group (p<0.05) was considered effective, i.e. it had a significant inhibitory effect on tumor growth. the TGI (%) was calculated as follows.

$$TGI(\%)=[1-(Ti-T0)/(Vi-V0)]\times 100, \text{ where}$$

Ti: the mean tumor volume of the treatment group on day i.
T0: the mean tumor volume of the treatment group on day 0.
Vi: the mean tumor volume of the solvent control group on day i.
V0: mean tumor volume of the solvent control group on day 0.

The animals were executed at the end of the assay, tumor were weighed and the tumor weight inhibition rate $IR_{TW}\%$ was calculated, with $IR_{TW}\% \geq 60\%$ as the reference index of effectiveness, calculated using the following formula, $$\text{Tumor weight inhibition rate } IR_{TW}(\%) = (W \text{ solvent control} - W \text{ treatment group})/W \text{ solvent control} \times 100, W \text{ is tumor weight.}$$

Figure 19:
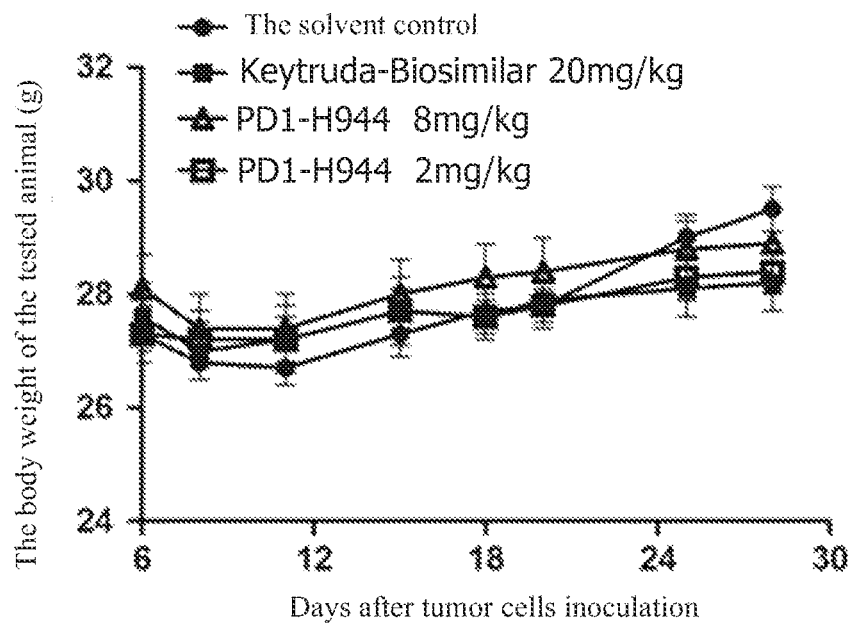
FIG. 19: Graph on the trend of animal body weight after administration.

All test animals were in good general condition in terms of activity and feeding during the administration of the drug, and to some extent, their body weight increased. There was no significant difference in the body weight of the animals after the administration of the test and control drugs (P>0.05) (Table 8 and FIG. 19).

TABLE 8

Effect of PD1-H944 on body weight of MC38 colon cancer transplanted B-hPD-1 humanized mice

| Group | No. of animals | Body weight (g)[a] Before administration | Body weight (g)[a] 23 days after the first dose | P[b] | Weight change after 23 days of dosing (g) |
|---|---|---|---|---|---|
| Group 1: Solvent control | 8 | 27.3 ± 0.5 | 29.5 ± 0.4 | — | +2.2 |
| Group 2: Pembrolizumab 20 mg/kg | 8 | 27.6 ± 0.6 | 28.2 ± 0.5 | 0.062 | +0.6 |
| Group 5: PD1-H944 8 mg/kg | 8 | 28.1 ± 0.6 | 28.9 ± 0.6 | 0.421 | +0.8 |
| Group 6: PD1-H944 2 mg/kg | 8 | 27.3 ± 0.5 | 28.4 ± 0.4 | 0.070 | +1.1 |

Note:
[a]mean ± standard error.
[b]statistical comparison of treatment group body weight with solvent control group body weight 23 days after dosing, t-test.

Figure 20:
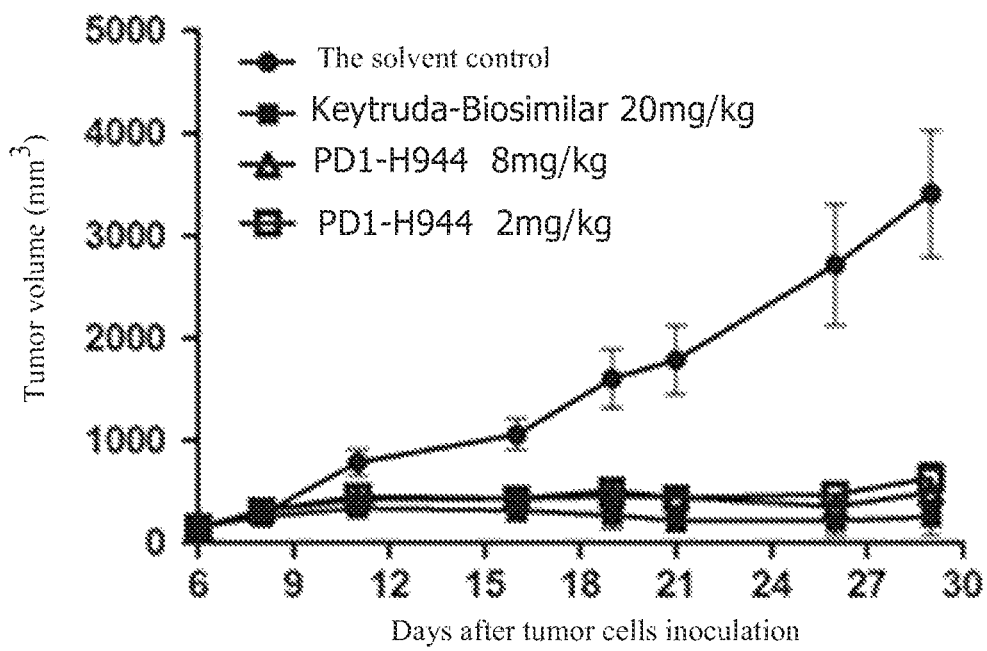
FIG. 20: Graph on the trend tumor volume growth after drug administration.

The tumor volumes for each group in the assay were shown in Table 9 and FIG. 20.

TABLE 9

Effect of PD1-H944 on tumor volume in MC38 colon cancer transplanted B-hPD-1 humanized mice (mean ± standard error)

| Day | Solvent control group Tumor volume (mm³) | N | Pembrolizumab 20 mg/kg group Tumor volume (mm³) | N | TGI (%) | PD1-H944 8 mg/kg group Tumor volume (mm³) | N | TGI (%) | PD1-H944 2 mg/kg group Tumor volume (mm³) | N | TGI (%) |
|---|---|---|---|---|---|---|---|---|---|---|---|
| 6 | 148 ± 11 | 8 | 152 ± 14 | 8 | / | 148 ± 15 | 8 | / | 146 ± 12 | 8 | / |
| 8 | 274 ± 29 | 8 | 248 ± 20 | 8 | 23.6 | 308 ± 22 | 8 | −26.3 | 312 ± 24 | 8 | −31.2 |
| 11 | 782 ± 129 | 8 | 334 ± 33** | 8 | 71.2 | 415 ± 61* | 8 | 57.9 | 454 ± 31* | 8 | 51.4 |
| 16 | 1052 ± 148 | 8 | 309 ± 103** | 8 | 82.6 | 428 ± 88** | 8 | 69.0 | 429 ± 47** | 8 | 68.7 |
| 19 | 1597 ± 286 | 8 | 263 ± 134** | 8 | 92.3 | 448 ± 111** | 8 | 79.3 | 509 ± 91** | 8 | 75.0 |
| 21 | 1783 ± 339 | 8 | 213 ± 110** | 8 | 96.3 | 441 ± 95** | 8 | 82.1 | 435 ± 88** | 8 | 82.3 |
| 26 | 2712 ± 590 | 8 | 212 ± 149** | 8 | 97.7 | 350 ± 111** | 8 | 92.1 | 470 ± 120** | 8 | 87.3 |
| 29 | 3405 ± 624 | 8 | 248 ± 176** | 8 | 97.0 | 484 ± 82** | 8 | 89.7 | 626 ± 150** | 8 | 85.3 |

Figure 21:
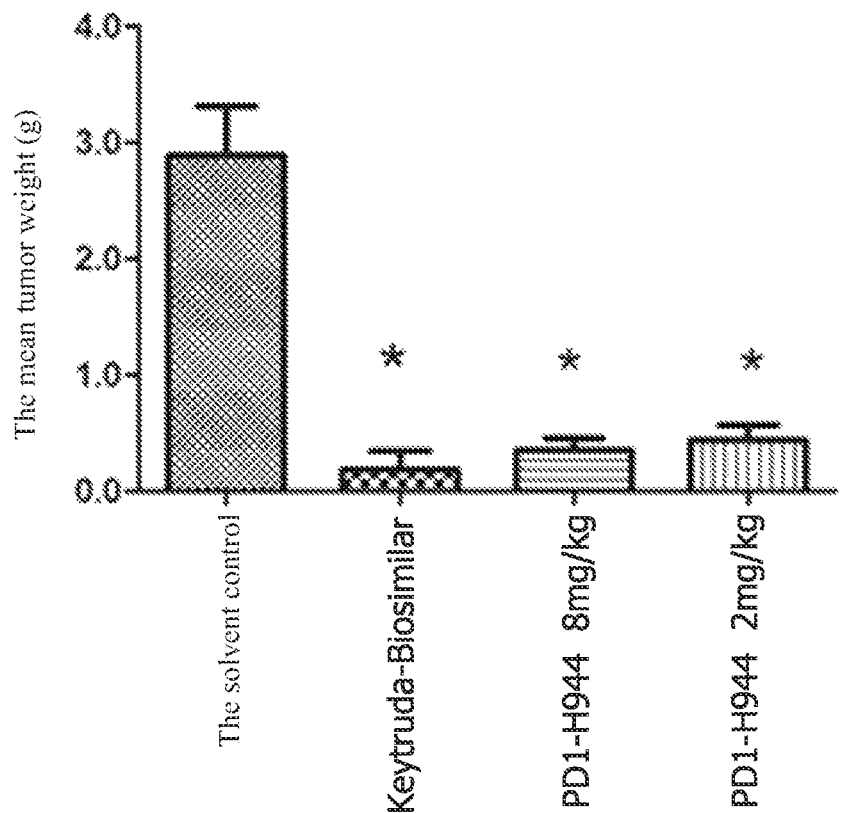
FIG. 21: Graph of tumor weight at the endpoint of the assay.

Note:
*P < 0.05,
**P < 0.01 compared to solvent control.
Days: number of days after cell inoculation;
N: number of animals in the group included in statistics 24 days after the first dose, all animals were euthanized and the tumors were stripped, weighed and photographed. Tumor weights were statistically compared between groups and the results are summarized in Table 10 and FIG. 21.

TABLE 10

Effect of PD1-H944 on tumor weight in MC38 colon cancer transplanted B-hPD-1 humanized mice (mean ± standard error)

| Group | No. of animals | Tumor weight (g) | Tumor $IR_{TW}$(%) |
|---|---|---|---|
| Solvent control group | 8 | 2.888 ± 0.426 | — |
| Pembrolizumab 20 mg/kg group | 8 | 0.186 ± 0.158** | 93.5 |
| PD1-H944 8 mg/kg group | 8 | 0.352 ± 0.106** | 87.8 |
| PD1-H944 2 mg/kg group | 8 | 0.441 ± 0.129** | 84.7 |

Note:
*P < 0.05,
**P < 0.01 compared to solvent control group.

For the solvent control group: tumor volume continued to grow after grouping and the mean tumor volume at the end of the trial was 3405±624 mm³.

For the positive control group: after Pembrolizumab administration at 20 mg/kg, tumor volume increased slowly compared to the solvent control group, with a significant difference in tumor volume from day 5 of administration (P<0.05); the TGI % at the end of the trial was 97.0% and the inhibition rate of tumor weight was 93.5%, P<0.05 compared to the solvent control group. Pembrolizumab showed obvious tumor inhibition on this efficacy model, indicating that this model can be used for the efficacy evaluation of Keytruda epitope binding antibody drug.

For the PD1-H9448 mg/kg group: After PD1-H944 administration at 8 mg/kg, the tumor volume increased slowly compared to the solvent control group, and the tumor volume showed a significant difference from the 5th day of administration (P<0.05); the TGI % at the end of the trial was 89.7% and the inhibition rate of tumor weight was 87.8%, P<0.05 compared to the solvent control group.

For the PD1-H9442 mg/kg group: After PD1-H944 administered at 2 mg/kg, tumor volume increased slowly compared to the solvent control group, with a significant difference in tumor volume from day 5 (p<0.05); the TGI % at the end of the trial was 85.3% and the tumor weight inhibition rate was 84.7%, p<0.05 compared to the solvent control group. This again suggests that the subjected PD1-H944 antibody binding to the PD-1 epitope is effective in this model, displaying a significant tumor-suppressive effect on MC38 colon cancer subcutaneous graft tumors displaying dose correlation. The anti-tumor efficacy of PD1-H944 and Pembrolizumab in this assay was also confirmed in terms of tumor weight.

The results of this assay showed that intraperitoneal administration of PD1-H9448 mg/kg or 2 mg/kg every 3 days for 6 consecutive doses significantly inhibited the growth of MC38 transplanted tumors in PD-1 humanized mice (P<0.05), and the animal characterization and body weights of the administered groups were not different from those of the model group. Considering the preference of the model design for different epitopes of antibodies, this assay did not evaluate the efficacy difference between PD1-H944 and Pembrolizumab.

The in vivo pharmacodynamics study investigated the anti-tumor effect of PD1-H944 alone on subcutaneous transplanted MC38 colon cancer in humanized PD-1 C57BL/6 mouse as the animal model. The B-hPD-1 humanized mouse is a C57BL/6 mouse whose PD-1 gene had been humanized, making the mouse suitable for in vivo evaluation of the efficacy of anti-human PD-1 antibody drugs. The model was selective for the efficacy of different epitopes of PD-1 antibodies, and Pembrolizumab showed significant tumor inhibition in this model. The results showed that PD1-H944 alone (2, 8 and 20 mg/kg administered every 3 days for 6 consecutive doses) significantly inhibited the growth of MC38 transplanted tumors and summary data are presented in Tables 11 and 12.

TABLE 11

Antitumor effect of PD1-H944 on MC38 colon cancer transplanted B-hPD-1 humanized mice

| | | | At the end of the assay | |
|---|---|---|---|---|
| Subgroups n = 7-8 | Duration and frequency of administration | Route of administration | Inhibition rate of Tumor volume TGI (%) | Tumor $IR_{TW}$(%) |
| Solvent control group | 3 days/dose × 6 times, observed for 10 days after stopping the drug | Intraperitoneal injection | 0.0 | 0.0 |
| Nivolumab 20 mg/kg | | | 17.8 | 13.2 |
| PD1-H944 20 mg/kg | | | 96.7 | 97.4 |

TABLE 12

Antitumor effects of different doses of PD1-H944 on humanized PD-1 mouse with colon cancer transplant tumors

| | | | At the end of the assay | |
|---|---|---|---|---|
| Subgroups n = 7-8 | Duration and frequency of administration | Route of administration | Tumor volume inhibition rate TGI (%) | Tumor $IR_{TW}$ (%) |
| Solvent control group | 3 days/dose × 6 times, observed for 9 days after stopping the drug | Intraperitoneal injection | 0.0 | 0.0 |
| Pembrolizumab 20 mg/kg | | | 97.0 | 93.5 |
| PD1-H944 2 mg/kg | | | 85.3 | 84.7 |
| PD1-H944 8 mg/kg | | | 89.7 | 87.8 |

Example 6 Identification of amino acid sites specifically bound by PD1-H944

Data from Example 4.2 show that PD1-H944 effectively competes with PD-L1 (FIG. 7A) or PD-L2 (FIG. 7B) for binding to PD-1 protein, demonstrating the overlapping between the binding epitope on PD-1 targeted byPD1-H944 and that targeted by the PD-L1 orPD-L2 ligand.

6.1 Molecular simulation predicting PD1-H944 conformational epitopes

Figure 22:
FIG. 22: Homology modelling of PD1-H944 docked to the crystal structure of PD1.

In order to investigate the interaction between PD1-H944-PD-1 protein interface, in this example ZDOCK docking of PD1-H944 and PD-1 protein was performed. Based on the fact that the PD-1 protein binding epitope targeted by PD1-H944 overlaps that targeted by the ligand PD-L1, homology modelling for PD1-H944 was performed using the Antibody model program in DS 4.0 (Accelrys Software Inc.), and the final model construct validity was tested by Ramachandran map. The PD-1 protein 3-dimensional structure was download from the PDB database (PDB ID: 4ZQK) and initialized by the Protein Preparation program. The binding model of PD1-H944 model and the PD-1 structure was docked by ZDOCK program. The top ten in scoring were then RDOCK optimized. The best model was further analyzed by the Protein Interface Analysis program (FIG. 22). The docking model interface interaction showed that the main peptide sequences bound by PD1-H944 to PD-1 protein were the CC" and FG sheets (Table 13)

TABLE 13 the main peptide sequences in PD1-H944 bind to PD-1 protein (underlined) predicted by molecular simulations

| Location | Sequences |
|---|---|
| CC' sheet | $^{60}$SESFV$^{64}$ |
|  | $^{78}$KLAAFPEDRSOP$^{89}$ |
| FG sheet | $^{128}$LAPKAQI$^{134}$ |

TABLE 14

Design of mutants in the extracellular region of recombinant PD-1 protein

| Distribution | Mutation sites |
|---|---|
| N-loop | D29A\R30A, R30A |
| CC' sheet | E61A, N66A, K78A, D85A, D85A\S87A |
| FG sheet | P130A, P130A\K131A, E136A\R139A |

Figure 24:
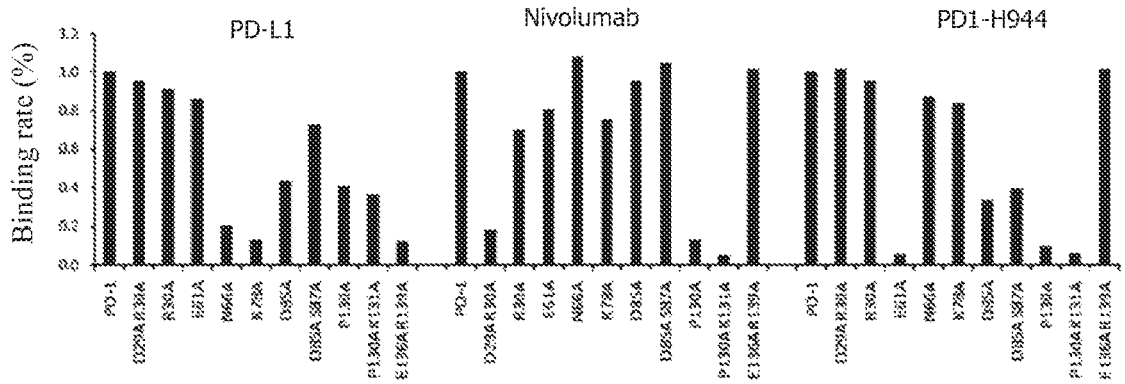
FIG. 24: The binding of PD-1 protein mutants to PD-L1, Nivolumab, and PD1-H944.

The binding of each mutant in Table 14 to PD1-H944 was determined by ELISA according to the method of Example 4.2. The mutants have a different degree of decrease in binding compared to the non-mutated PD-1 protein. Data were analyzed and plotted using Excel 2007 with PD-1 protein mutant profile as the horizontal coordinate and binding rate as the vertical coordinate [binding rate=$OD_{(PD\text{-}1\ protein\ mutant)}/OD_{(PD\text{-}1\ protein)} \times 100\%$]. The results showed that the main binding sites of PD-1 protein for the ligand PD-L1 were Site 2, Site 3, Site 4 and Site 5 on the CC" and FG sheets of PD-1 protein, which were consistent with the crystals complex (PDB ID: 4ZQK). The binding sites for the positive control Nivolumab binding to PD-1 protein were mainly located on Site 1 and Site 4 of its N-loop and FG sheets, and this result was also consistent with the analysis of its complex crystals (PDB ID: 5WT9); the main binding sites forPD1-H944binding to PD-1 protein were E61, K78, D85 and P130 on Site 3 and Site 4. The results were also consistent with those of the docking model in the above example (FIG. 24 and Table 15), and validated the accuracy of the docking model between PD1-H944 and PD-1 proteins.

TABLE 15

Binding of PD-L1, Nivolumab and PD1-H944 to each PD-1 mutant

|  | N loop | | CC' Sheets | | | | | FG sheets | | | |
|---|---|---|---|---|---|---|---|---|---|---|---|
|  | Site 1 | | | Site3 | | | | Site4 | | Site5 | |
|  | D29A | | Site2 | D85A | | | | P130A | | E136A | |
|  | R30A | R30A | N66A | K78A | D85A | S87A | E61A | P130A | K131A | R139A | PD-1 |
| PD-L1 | + | + | − | − | − | +/− | + | − | − | − | + |
| Nivolumab | − | +/− | + | +/− | + | + | +/− | − | − | + | + |
| PD-1-H944 | + | + | + | +/− | − | − | − | − | − | + | + |

Note:
+: represents binding rate >85%, none sensitive binding sites; +/−: represents 85% ≥ binding rate >50%, partly sensitive binding sites; −: represents binding rate ≤50%, sensitive binding sites.

6.2 Validation of PD1-H944 binding epitopes tested by PD-1 protein mutants

Figure 23:
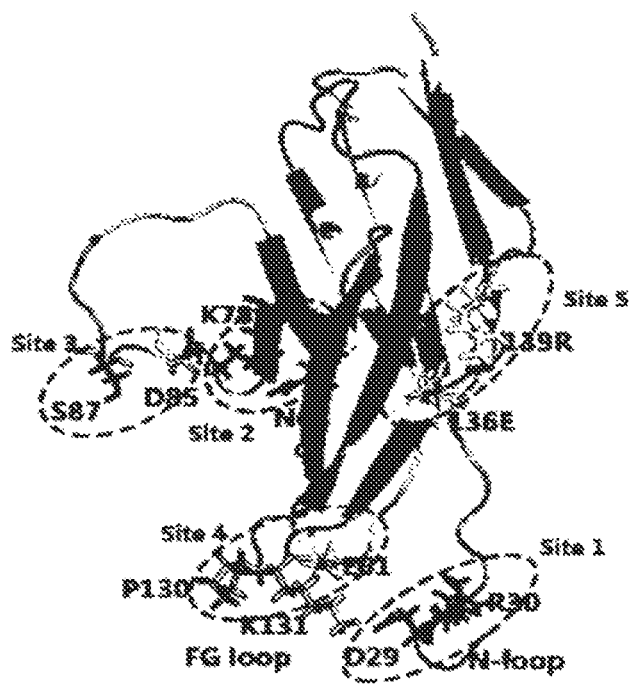
FIG. 23: A model of the PD1 protein showing the mutation site.

To further confirm the functional epitope of PD1-H944, based on the peptide sequences predicted to be the main sites for PD1-H944 binding to PD-1 protein in Table 13, a series of alanine mutated PD-1 protein mutants were prepared and analyzed by ELISA assays. To validate the accuracy of the model, several sites outside of the model of Example 6.1 were also elected for this study (Table 14), and these mutant sites were broadly grouped into five spatial conformational epitopes (FIG. 23).

Figure 25:
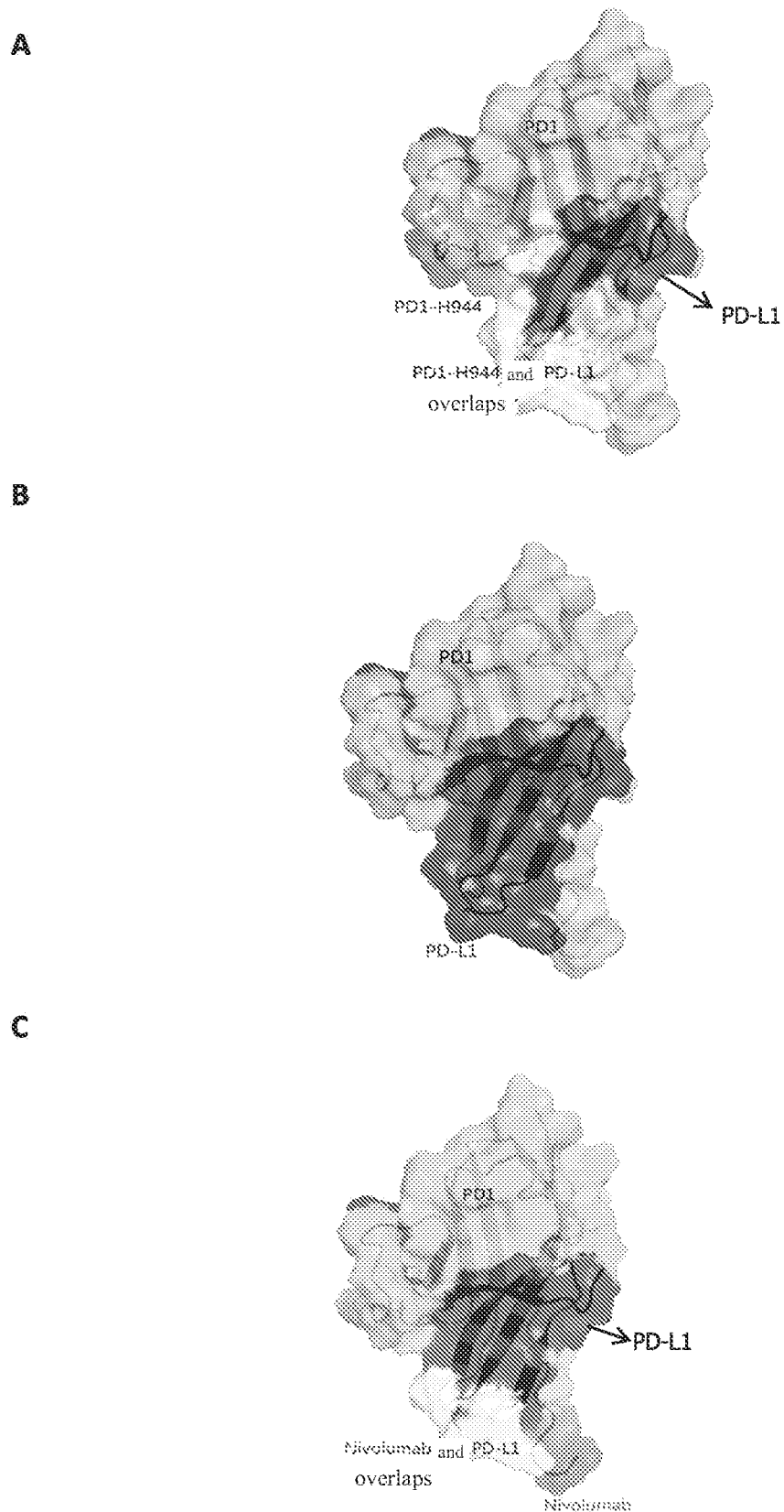
Fig.25A-C: The amino acid sites where PD1-H944, PD-L1 and Nivolumab specifically bind to PD-1.

The docking model between PD1-H944 and PD-1 protein shows that binding epitope on the PD-1 protein targeted by PD1-H944 overlaps with that by the ligand PD-L1. This fact supports the idea that PD1-H944 acts through direct space steric hindrance. Meanwhile, the overlap between the epitope targeted by both PD1-H944 and Nivolumab suggested that PD1-H944 has a larger region for blocking the binding of PD-L1 to epitopes (FIG. 25A-C). Therefore PD1-H944 may have superior therapeutic efficacy in oncology treatment. The sequences in Table 13 correspond to the labeled amino acid residues of SEQ ID NO: 1.

The invention claimed is:

1. An isolated PD-1 antibody or antigen-binding fragment thereof comprising:
   a light chain variable region or portion thereof; and
   a heavy chain variable region or portion thereof;
   wherein the light chain variable region or portion thereof comprises:
      a light chain CDR1 having an amino acid sequence of SEQ ID NO: 10,
      a light chain CDR2 having an amino acid sequence of SEQ ID NO: 11, and
      a light chain CDR3 having an amino acid sequence of SEQ ID NO: 12; and
         wherein the heavy chain variable region or portion thereof comprises:
      a heavy chain CDR1 having amino acid sequence of SEQ ID NO: 13,
      a heavy chain CDR2 having amino acid sequence of SEQ ID NO: 14, and
      a heavy chain CDR3 having amino acid sequence of SEQ ID NO: 15.

2. The isolated PD-1 antibody or antigen-binding fragment thereof of claim 1, wherein the PD-1 antibody or antigen-binding fragment thereof further comprises: an amino acid sequence having at least 90%, 92%, 95%, 98% or 100% sequence identity to the PD-1 antibody light chain variable region sequence of SEQ ID NO:23, and an amino acid sequence having at least 90%, 92%, 95%, 98% or 100% sequence identity to the PD-1 antibody heavy chain variable region sequence of SEQ ID NO:22.

3. The isolated PD-1 antibody or antigen-binding fragment thereof of claim 1, wherein said antibody further comprises a light chain constant region and a heavy chain constant region, said light chain constant region has an amino acid sequence having at least 90%, 92%, 95%, 98% or 100% sequence identity to the kappa light chain constant region of SEQ ID NO:25, and/or said heavy chain constant region has an amino acid sequence having at least 90%, 92%, 95%, 98% or 100% sequence identity to the IgG4 heavy chain constant region of SEQ ID NO:24.

4. The isolated PD-1 antibody or antigen-binding fragment thereof of claim 1, wherein the PD-1 antibody is an IgG antibody.

5. The isolated PD-1 antibody or antigen binding fragment thereof of claim 1, wherein the PD-1 antibody is an IgG4 antibody.

6. The isolated PD-1 antibody or antigen binding fragment thereof of claim 1, wherein the PD-1 antibody is a monoclonal antibody.

7. The isolated PD-1 antibody or antigen-binding fragment thereof of claim 1, wherein the PD-1 antibody or antigen-binding fragment thereof binds to a recombinant human PD-1 protein with an affinity in KD average of 20-200 pM.

8. The isolated PD-1 antibody or antigen-binding fragment thereof of claim 1, wherein the PD-1 antibody or antigen-binding fragment thereof binds to a recombinant human PD-1 protein with an affinity in KD average of 60-70 pM.

9. The isolated PD-1 antibody or antigen-binding fragment thereof of claim 1, wherein the PD-1 antibody or antigen-binding fragment thereof binds to a recombinant human PD-1 protein with an affinity in KD average of 64.8 pM.

10. The isolated PD-1 antibody or antigen-binding fragment thereof of claim 1, wherein the PD-1 antibody or antigen-binding fragment thereof specifically binds to a PD-1 protein molecule comprising the amino acid sequence of SEQ ID NO:1.

11. The isolated PD-1 antibody or antigen-binding fragment thereof of claim 1, wherein the PD-1 antibody or antigen-binding fragment thereof specifically binds to a protein molecule having an amino acid sequence having at least 90%, 92%, 95%, 98% or 100% sequence identity to SEQ ID NO:1.

12. The isolated PD-1 antibody or antigen-binding fragment thereof of claim 1, wherein the PD-1 antibody or antigen-binding fragment is in the form of Fv, Fab, Fab', Fab'-SH, F(ab')2, and single chain antibody molecule.

13. The isolated PD-1 antibody or antigen-binding fragment thereof of claim 1, wherein the PD-1 antibody or antigen-binding fragment is in the form of a single chain antibody selected from the group consisting of scFv, di-scFv, tri-scFv, diabody, and scFab.

14. A modified drug molecule comprising:
   one of a small molecule and a biomacromolecule; and
   an isolated PD-1 antibody or antigen-binding fragment comprising:
      a light chain variable region or portion thereof; and
      a heavy chain variable region or portion thereof;
      wherein the light chain variable region or portion thereof comprises:
         a light chain CDR1 having an amino acid sequence of SEQ ID NO: 10,
         a light chain CDR2 having an amino acid sequence of SEQ ID NO: 11, and
         a light chain CDR3 having an amino acid sequence of SEQ ID NO: 12; and
      wherein the heavy chain variable region or portion thereof comprises:
         a heavy chain CDR1 having amino acid sequence of SEQ ID NO: 13,
         a heavy chain CDR2 having amino acid sequence of SEQ ID NO: 14, and
         a heavy chain CDR3 having amino acid sequence of SEQ ID NO: 15, wherein the modified drug molecule is one of a covalent conjugate, a non-covalent conjugate, and a recombinant multi-target fusion drug.

15. The modified drug molecule of claim 14,
wherein the light chain variable region or portion thereof comprises an amino acid sequence having at least 90%, 92%, 95%, 98% or 100% sequence identity to the PD-1 antibody light chain variable region sequence of SEQ ID NO:23,
wherein the heavy chain variable region or portion thereof comprises an amino acid sequence having at least 90%, 92%, 95%, 98% or 100% sequence identity to the PD-1 antibody heavy chain variable region sequence of SEQ ID NO:22.

16. A pharmaceutical composition comprising one of: (a) an isolated PD-1 antibody or antigen-binding fragment thereof comprising: a light chain variable region or portion thereof; and a heavy chain variable region or portion thereof; wherein the light chain variable region or portion thereof comprises: a light chain CDR1 having an amino acid sequence of SEQ ID NO: 10, a light chain CDR2 having an amino acid sequence of SEQ ID NO: 11, and a light chain CDR3 having an amino acid sequence of SEQ ID NO: 12; and
wherein the heavy chain variable region or portion thereof comprises: a heavy chain CDR1 having amino acid sequence of SEQ ID NO: 13, a heavy chain CDR2 having amino acid sequence of SEQ ID NO: 14, and a heavy chain CDR3 having amino acid sequence of SEQ ID NO: 15; and (b) a modified drug molecule comprising: one of a small molecule and a biomacromolecule; and an isolated PD-1 antibody or antigen-binding fragment comprising: a light chain variable region or portion thereof; and a heavy chain variable region or portion thereof; wherein the light chain variable region or portion thereof comprises: a light chain CDR1 having an amino acid sequence of SEQ ID NO: 10, a light chain CDR2 having an amino acid sequence of SEQ ID NO: 11, and a light chain CDR3 having an amino acid sequence of SEQ ID NO: 12; and
wherein the heavy chain variable region or portion thereof comprises: a heavy chain CDR1 having amino acid sequence of SEQ ID NO: 13, a heavy chain CDR2 having amino acid sequence of SEQ ID NO: 14, and a heavy chain CDR3 having amino acid sequence of SEQ ID NO: 15, wherein the modified drug molecule is one of a covalent conjugate, a non-covalent conjugate, and a recombinant multi-target fusion drug.

17. The pharmaceutical composition according to claim 16, further comprising a therapeutic agent.

18. The pharmaceutical composition according to claim 16, wherein the PD-1 antibody or antigen-binding fragment thereof further comprises: an amino acid sequence having at least 90%, 92%, 95%, 98% or 100% sequence identity to the PD-1 antibody light chain variable region sequence of SEQ ID NO:23, and an amino acid sequence having at least 90%, 92%, 95%, 98% or 100% sequence identity to the PD-1 antibody heavy chain variable region sequence of SEQ ID NO:22.

19. The pharmaceutical composition according to claim 16, wherein the PD-1 antibody or antigen-binding fragment thereof binds to a recombinant human PD-1 protein with an affinity in KD average of 20-200 pM.

20. The pharmaceutical composition according to claim 16, wherein the PD-1 antibody or antigen-binding fragment thereof specifically binds to a PD-1 protein molecule comprising the amino acid sequence of SEQ ID NO:1.

21. The pharmaceutical composition according to claim 16, wherein the PD-1 antibody or antigen-binding fragment is in the form of Fv, Fab, Fab', Fab'-SH, F(ab')2, and single chain antibody molecule.

22. A pharmaceutical combination, comprising one of: (a) an isolated PD-1 antibody or antigen-binding fragment thereof comprising: a light chain variable region or portion thereof; and a heavy chain variable region or portion thereof; wherein the light chain variable region or portion thereof comprises: a light chain CDR1 having an amino acid sequence of SEQ ID NO: 10, a light chain CDR2 having an amino acid sequence of SEQ ID NO: 11, and a light chain CDR3 having an amino acid sequence of SEQ ID NO: 12; and
wherein the heavy chain variable region or portion thereof comprises: a heavy chain CDR1 having amino acid sequence of SEQ ID NO: 13, a heavy chain CDR2 having amino acid sequence of SEQ ID NO: 14, and a heavy chain CDR3 having amino acid sequence of SEQ ID NO: 15; and (b) a modified drug molecule comprising: one of a small molecule and a biomacromolecule; and an isolated PD-1 antibody or antigen-binding fragment comprising: a light chain variable region or portion thereof; and a heavy chain variable region or portion thereof; wherein the light chain variable region or portion thereof comprises: a light chain CDR1 having an amino acid sequence of SEQ ID NO: 10, a light chain CDR2 having an amino acid sequence of SEQ ID NO: 11, and a light chain CDR3 having an amino acid sequence of SEQ ID NO: 12; and
wherein the heavy chain variable region or portion thereof comprises: a heavy chain CDR1 having amino acid sequence of SEQ ID NO: 13; a heavy chain CDR2 having amino acid sequence of SEQ ID NO: 14; and a heavy chain CDR3 having amino acid sequence of SEQ ID NO: 15, wherein the modified drug molecule is one of a covalent conjugate, a non-covalent conjugate, and a recombinant multi-target fusion drug, and wherein the pharmaceutical composition further comprises a therapeutic agent.

* * * * *

SEQUENCE LISTING

<160> NUMBER OF SEQ ID NOS: 38

<210> SEQ ID NO 1
<211> LENGTH: 167
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln
                165

<210> SEQ ID NO 2
<211> LENGTH: 54
<212> TYPE: DNA
<213> ORGANISM: Mus musculus

<400> SEQUENCE: 2
tctagtggtg gcggtggttc gggcggtggt ggaggtggta gttctagatc ttcc      54

<210> SEQ ID NO 3
<211> LENGTH: 741
<212> TYPE: DNA
<213> ORGANISM: Mus musculus

<400> SEQUENCE: 3
gatattgtgc taactcaatc tccagcttct ttggctgtgt ctctagggca gagggccacc      60
atatcctgca gagccagtga aagtgttgat agtyatggca atagttttat gcactggtac     120
cagcagaaac caggacagcc acccaaactc ctcatctatg ctgcatccaa ccaaggatcc     180
ggggtccctg ccaggtttag tggcagtggg tctgggacag acttcagcct caacatccat     240
cctatggagg aggatgatac tgcaatgtat ttctgtcagc aaagtaagga ggttccgtgg     300
acgttcggtg gaggcaccaa gctggaaatc aaatctagtg gtggcggtgg ttcgggcggt     360
ggtggaggtg gtagttctag atcttccgag gtgcaactgg tggaatctgg gggaggctta     420
gtgaagcctg gagggtccct gaaactctcc tgtgcagcct ctggattcac tttcagttcc     480
tatggcatgt cttgggttcg tcagactccg gagaagaggc tggagtgggt cgcgaccatt     540

```
agtggtggtg gtcgtgacac ctactattca gacagtgtga aggggcggtt caccgtctcc    600
agagacaatg ccaagaacaa cctgttcctg caaatgagca gtctgaggtc tgaagacacg    660
gccttgtatt attgttcacg tcaatatggt acggtctggt tttttaactg gggccagggg    720
actctggtca ctgtctctgc a                                              741

<210> SEQ ID NO 4
<211> LENGTH: 354
<212> TYPE: DNA
<213> ORGANISM: Mus musculus

<400> SEQUENCE: 4
gaggtgcaac tggtggaatc tgggggaggc ttagtgaagc ctggagggtc cctgaaactc     60
tcctgtgcag cctctggatt cactttcagt cctatggca tgtcttgggt tcgtcagact    120
ccggagaaga ggctggagtg ggtcgcgacc attagtggtg gtggtcgtga cacctactat    180
tcagacagtg tgaaggggcg gttcaccgtc tccagagaca tgccaagaa caacctgttc    240 ctgcaaatga gcagtctgag gtctgaagac acggccttgt attattgttc acgtcaatat    300
ggtacggtct ggttttttaa ctggggccag gggactctgg tcactgtctc tgca          354

<210> SEQ ID NO 5
<211> LENGTH: 333
<212> TYPE: DNA
<213> ORGANISM: Mus musculus

<400> SEQUENCE: 5
gatattgtgc taactcaatc tccagcttct ttggctgtgt ctctagggca gagggccacc     60
atatcctgca gagccagtga aagtgttgat agttatggca atagttttat gcactggtac    120
cagcagaaac caggacagcc acccaaactc ctcatctatg ctgcatccaa ccaaggatcc    180
ggggtccctg ccaggtttag tggcagtggg tctgggacag acttcagcct caacatccat    240
cctatggagg aggatgatac tgcaatgtat ttctgtcagc aaagtaagga ggttccgtgg    300
acgttcggtg gaggcaccaa gctggaaatc aaa                                 333

<210> SEQ ID NO 6
<211> LENGTH: 972
<212> TYPE: DNA
<213> ORGANISM: Mus musculus

<400> SEQUENCE: 6
gccaaaacga cacccccatc tgtctatcca ctggcccctg gatctgctgc ccaaactaac     60
tccatggtga cctgggatg cctggtcaag ggctatttcc ctgagccagt gacagtgacc    120
tggaactctg gatccctgtc cagcggtgtg cacaccttcc cagctgtcct gcagtctgac    180
ctctacactc tgagcagctc agtgactgtc ccctccagca cctggcccag cgagaccgtc    240
acctgcaacg ttgcccaccc ggccagcagc accaaggtgg acaagaaaat tgtgcccagg    300
gattgtggtt gtaagccttg catatgtaca gtcccagaag tatcatctgt cttcatcttc    360
cccccaaagc ccaaggatgt gctcaccatt actctgactc ctaaggtcac gtgtgttgtg    420
gtagacatca gcaaggatga tcccgaggtc cagttcagct ggtttgtaga tgatgtggag    480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaccaa aggcagaccg    660 aaggctccac aggtgtacac cattccacct cccaaggagc agatggccaa ggataaagtc    720
```

-continued

```
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aa                                                        972
```

<210> SEQ ID NO 7
<211> LENGTH: 321
<212> TYPE: DNA
<213> ORGANISM: Mus musculus

<400> SEQUENCE: 7

```
cgggctgatg ctgcaccaac tgtatccatc ttcccaccat ccagtgagca gttaacatct     60
ggaggtgcct cagtcgtgtg cttcttgaac aacttctacc ccaaagacat caatgtcaag    120
tggaagattg atggcagtga acgacaaaat ggcgtcctga acgttggac tgatcaggac    180 agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg t                                              321
```

<210> SEQ ID NO 8
<211> LENGTH: 118
<212> TYPE: PRT
<213> ORGANISM: Mus musculus

<400> SEQUENCE: 8

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Ser Asp Ser Val
    50                  55                  60

Lys Gly Arg Phe Thr Val Ser Arg Asp Asn Ala Lys Asn Asn Leu Phe
65                  70                  75                  80

Leu Gln Met Ser Ser Leu Arg Ser Glu Asp Thr Ala Leu Tyr Tyr Cys
                85                  90                  95

Ser Arg Gln Tyr Gly Thr Val Trp Phe Phe Asn Trp Gly Gln Gly Thr
            100                 105                 110

Leu Val Thr Val Ser Ala
        115
```

<210> SEQ ID NO 9
<211> LENGTH: 111
<212> TYPE: PRT
<213> ORGANISM: Mus musculus

<400> SEQUENCE: 9

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45
```

```
Lys Leu Leu Ile Tyr Ala Ala Ser Asn Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Trp Thr Phe Gly Gly Gly Thr Lys Leu Glu Ile Lys
            100                 105                 110

<210> SEQ ID NO 10
<211> LENGTH: 12
<212> TYPE: PRT
<213> ORGANISM: Mus musculus

<400> SEQUENCE: 10

Glu Ser Val Asp Ser Tyr Gly Asn Ser Phe Met His
1               5                   10

<210> SEQ ID NO 11
<211> LENGTH: 11
<212> TYPE: PRT
<213> ORGANISM: Mus musculus

<400> SEQUENCE: 11

Ala Ala Ser Asn Gln Gly Ser Gly Val Pro Ala
1               5                   10

<210> SEQ ID NO 12
<211> LENGTH: 9
<212> TYPE: PRT
<213> ORGANISM: Mus musculus

<400> SEQUENCE: 12

Gln Gln Ser Lys Glu Val Pro Trp Thr
1               5

<210> SEQ ID NO 13
<211> LENGTH: 10
<212> TYPE: PRT
<213> ORGANISM: Mus musculus

<400> SEQUENCE: 13

Gly Phe Thr Phe Ser Ser Tyr Gly Met Ser
1               5                   10

<210> SEQ ID NO 14
<211> LENGTH: 19
<212> TYPE: PRT
<213> ORGANISM: Mus musculus

<400> SEQUENCE: 14

Val Ala Thr Ile Ser Gly Gly Gly Arg Asp Thr Tyr Tyr Ser Asp Ser
1               5                   10                  15

Val Lys Gly

<210> SEQ ID NO 15
<211> LENGTH: 11
<212> TYPE: PRT
<213> ORGANISM: Mus musculus

<400> SEQUENCE: 15

Ser Arg Gln Tyr Gly Thr Val Trp Phe Phe Asn
```

<210> SEQ ID NO 16
<211> LENGTH: 445
<212> TYPE: PRT
<213> ORGANISM: Homo sapiens

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Arg Leu Glu Trp Val
        35                  40                  45

Ala Thr Ile Ser Gly Gly Gly Arg Asp Thr Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Tyr Cys
                85                  90                  95

Ser Arg Gln Tyr Gly Thr Val Trp Phe Phe Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

```
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 17
<211> LENGTH: 218
<212> TYPE: PRT
<213> ORGANISM: Homo sapiens

<400> SEQUENCE: 17

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Glu Ser Val Asp Ser Tyr
            20                  25                  30
Gly Asn Ser Phe Met His Trp Tyr Gln Gln Lys Pro Gly Gln Pro Pro
        35                  40                  45
Arg Leu Leu Ile Tyr Ala Ala Ser Asn Gln Gly Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Met Tyr Phe Cys Gln Gln Ser Lys
                85                  90                  95
Glu Val Pro Trp Thr Phe Gly Gln Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 18
<211> LENGTH: 464
<212> TYPE: PRT
<213> ORGANISM: Homo sapiens

<400> SEQUENCE: 18

Met Gly Trp Ser Leu Ile Leu Leu Phe Leu Val Ala Val Ala Thr Arg
1               5                   10                  15
Val Leu Ser Glu Val Gln Leu Val Glu Ser Gly Gly Gly Leu Val Lys
            20                  25                  30
```

-continued

```
Pro Gly Gly Ser Leu Arg Leu Ser Cys Ala Ala Ser Gly Phe Thr Phe
            35                  40                  45

Ser Ser Tyr Gly Met Ser Trp Val Arg Gln Ala Pro Gly Lys Arg Leu
 50                  55                  60

Glu Trp Val Ala Thr Ile Ser Gly Gly Gly Arg Asp Thr Tyr Tyr Ser
 65                  70                  75                  80

Asp Ser Val Lys Gly Arg Phe Thr Ile Ser Arg Asp Asn Ala Lys Asn
                 85                  90                  95

Asn Leu Tyr Leu Gln Met Asn Ser Leu Arg Ala Glu Asp Thr Ala Val
                100                 105                 110

Tyr Tyr Cys Ser Arg Gln Tyr Gly Thr Val Trp Phe Phe Asn Trp Gly
            115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser Gln Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Val Leu Asp
                405                 410                 415

Ser Asp Gly Ser Phe Phe Leu Tyr Ser Arg Leu Thr Val Asp Lys Ser
                420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
```

<210> SEQ ID NO 19
<211> LENGTH: 237
<212> TYPE: PRT
<213> ORGANISM: Homo sapiens

<400> SEQUENCE: 19

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Glu Ser Val
        35                  40                  45

Asp Ser Tyr Gly Asn Ser Phe Met His Trp Tyr Gln Gln Lys Pro Gly
    50                  55                  60

Gln Pro Pro Arg Leu Leu Ile Tyr Ala Ala Ser Asn Gln Gly Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Met Tyr Phe Cys Gln
            100                 105                 110

Gln Ser Lys Glu Val Pro Trp Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 20
<211> LENGTH: 19
<212> TYPE: PRT
<213> ORGANISM: Homo sapiens

<400> SEQUENCE: 20

Met Gly Trp Ser Leu Ile Leu Leu Phe Leu Val Ala Val Ala Thr Arg
1               5                   10                  15

Val Leu Ser

<210> SEQ ID NO 21
<211> LENGTH: 19
<212> TYPE: PRT
<213> ORGANISM: Homo sapiens

<400> SEQUENCE: 21

Met Gly Trp Ser Cys Ile Ile Leu Phe Leu Val Ala Thr Ala Thr Gly
1               5                   10                  15

Val His Ser

<210> SEQ ID NO 22
<211> LENGTH: 118
<212> TYPE: PRT
<213> ORGANISM: Homo sapiens

<400> SEQUENCE: 22

Glu Val Gln Leu Val Glu Ser Gly Gly Gly Leu Val Lys Pro Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Arg Leu Glu Trp Val
        35                  40                  45

Ala Thr Ile Ser Gly Gly Gly Arg Asp Thr Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Tyr Cys
                85                  90                  95

Ser Arg Gln Tyr Gly Thr Val Trp Phe Phe Asn Trp Gly Gln Gly Thr
            100                 105                 110

Leu Val Thr Val Ser Ser
        115

<210> SEQ ID NO 23
<211> LENGTH: 111
<212> TYPE: PRT
<213> ORGANISM: Homo sapiens

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Gly Asn Ser Phe Met His Trp Tyr Gln Gln Lys Pro Gly Gln Pro Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Met Tyr Phe Cys Gln Gln Ser Lys
                85                  90                  95

Glu Val Pro Trp Thr Phe Gly Gln Gly Thr Lys Val Glu Ile Lys
            100                 105                 110

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 25
<211> LENGTH: 107
<212> TYPE: PRT
<213> ORGANISM: Homo sapiens

<400> SEQUENCE: 25

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
```

```
            85                  90                  95
Pro Val Thr Lys Ser Phe Asn Arg Gly Glu Cys
            100                 105

<210> SEQ ID NO 26
<211> LENGTH: 1395
<212> TYPE: DNA
<213> ORGANISM: Homo sapiens

<400> SEQUENCE: 26
atgggctggt ccctgattct gctgttcctg gtggctgtgg ctaccagggt gctgtctgag      60
gtccaacttg tggagtctgg aggaggactg gtgaagcctg gaggctccct gagactgtcc     120
tgtgctgcct ctggcttcac cttctcctcc tatgggatga gttgggtgag acaggctcct     180
gggaagagat ggagtggggt ggctaccatc tctggaggag caggacacac ctactactct     240
gactctgtga agggcaggtt cacaatcagc aggacaatg ccaagaacaa cctgtacctc      300
caaatgaact ccctgagggc tgaggacaca gcagtctact actgtagcag acaatatggc     360
acagtgtggt tcttcaactg gggacaaggc accctggtga cagtgtcctc tgctagcacc     420
aagggcccat cggtcttccc gctggcgccc tgctccagga gcacctccga gagcacagcc     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacgaagac ctacacctgc     660
aacgtagatc acaagcccag caacaccaag gtggacaaga gagttgagtc caaatatggt     720
cccccatgcc caccctgccc agcacctgag ttcctggggg gaccatcagt cttcctgttc     780
cccccaaaac ccaaggacac tctcatgatc tcccggaccc ctgaggtcac gtgcgtggtg     840
gtggacgtga gccaggaaga ccccgaggtc cagttcaact ggtacgtgga tggcgtggag     900
gtgcataatg ccaagacaaa gccgcgggag gagcagttca acagcacgta ccgtgtggtc     960
agcgtcctca ccgtcctgca ccaggactgg ctgaacggca aggagtacaa gtgcaaggtc    1020
tccaacaaag gcctcccgtc ctccatcgag aaaaccatct ccaaagccaa agggcagccc    1080
cgagagccac aggtgtacac cctgccccca tcccaggagg agatgaccaa gaaccaggtc    1140
agcctgacct gcctggtcaa aggcttctac cccagcgaca tcgccgtgga gtgggaaagc    1200
aatgggcagc cggagaacaa ctacaagacc acgcctcccg tgctggactc cgacggctcc    1260
ttcttcctct acagcaggct aaccgtggac aagagcaggt ggcaggaggg gaatgtcttc    1320
tcatgctccg tgatgcatga ggctctgcac aaccactaca cacagaagag cctctccctg    1380
tctctgggta aataa                                                     1395

<210> SEQ ID NO 27
<211> LENGTH: 714
<212> TYPE: DNA
<213> ORGANISM: Homo sapiens

<400> SEQUENCE: 27
atgggctggt cctgtatcat cctgttcctg gtggctacag ccacaggagt gcattctgag      60
attgtgctga cccagagccc tgccaccctg tccctgagcc tggagagag gctaccctg       120 tcctgtaggg catctgagtc tgtggactcc tatggcaact cctttatgca ctggtatcaa     180
cagaagcctg gacaaccacc aagactgctg atttatgctg ccagcaacca gggctctgga     240
gtgcctgcca ggttctctgg ctctggctct ggcacagact tcaccctgac catctcctcc    300
```

```
ttggaacctg aggactttgc tatgtacttc tgtcaacaga gcaaggaggt gccatggacc    360
tttggacaag gcaccaaggt ggagattaag cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttag          714
```

<210> SEQ ID NO 28
<211> LENGTH: 57
<212> TYPE: DNA
<213> ORGANISM: Homo sapiens

<400> SEQUENCE: 28

```
atgggctggt ccctgattct gctgttcctg gtggctgtgg ctaccagggt gctgtct    57
```

<210> SEQ ID NO 29
<211> LENGTH: 57
<212> TYPE: DNA
<213> ORGANISM: Homo sapiens

<400> SEQUENCE: 29

```
atgggctggt cctgtatcat cctgttcctg gtggctacag ccacaggagt gcattct    57
```

<210> SEQ ID NO 30
<211> LENGTH: 354
<212> TYPE: DNA
<213> ORGANISM: Homo sapiens

<400> SEQUENCE: 30

```
gaggtccaac ttgtggagtc tggaggagga ctggtgaagc ctggaggctc cctgagactg    60
tcctgtgctg cctctggctt caccttctcc tcctatggga tgagttgggt gagacaggct    120
cctgggaaga gattggagtg ggtggctacc atctctggag gaggcaggga cacctactac    180
tctgactctg tgaagggcag gttcacaatc agcagggaca tgccaagaa caacctgtac    240 ctccaaatga actccctgag ggctgaggac acagcagtct actactgtag cagacaatat    300
ggcacagtgt ggttcttcaa ctggggacaa ggcaccctgg tgacagtgtc ctct          354
```

<210> SEQ ID NO 31
<211> LENGTH: 333
<212> TYPE: DNA
<213> ORGANISM: Homo sapiens

<400> SEQUENCE: 31

```
gagattgtgc tgacccagag ccctgccacc ctgtccctga gccctggaga gagggctacc    60
ctgtcctgta gggcatctga gtctgtggac tcctatggca actcctttat gcactggtat    120
caacagaagc ctggacaacc accaagactg ctgatttatg ctgccagcaa ccagggctct    180
ggagtgcctg ccaggttctc tggctctggc tctggcacag acttcaccct gaccatctcc    240
tccttggaac tgaggacttt gctatgtac ttctgtcaac agagcaagga ggtgccatgg    300
acctttggac aaggcaccaa ggtggagatt aag                                  333
```

<210> SEQ ID NO 32
<211> LENGTH: 984
<212> TYPE: DNA
<213> ORGANISM: Homo sapiens

<400> SEQUENCE: 32

```
gctagcacca agggcccatc ggtcttcccg ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accctgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggaaagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa ataa                                            984
```

<210> SEQ ID NO 33
<211> LENGTH: 324
<212> TYPE: DNA
<213> ORGANISM: Homo sapiens

<400> SEQUENCE: 33

```
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324
```

<210> SEQ ID NO 34
<211> LENGTH: 247
<212> TYPE: PRT
<213> ORGANISM: Mus musculus

<400> SEQUENCE: 34

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80
```

-continued

```
Pro Met Glu Glu Asp Asp Thr Ala Met Tyr Phe Cys Gln Gln Ser Lys
                 85                  90                  95
Glu Val Pro Trp Thr Phe Gly Gly Gly Thr Lys Leu Glu Ile Lys Ser
            100                 105                 110
Ser Gly Gly Gly Gly Ser Gly Gly Gly Gly Ser Ser Arg Ser
        115                 120                 125
Ser Glu Val Gln Leu Val Glu Ser Gly Gly Leu Val Lys Pro Gly
    130                 135                 140
Gly Ser Leu Lys Leu Ser Cys Ala Ala Ser Gly Phe Thr Phe Ser Ser
145                 150                 155                 160
Tyr Gly Met Ser Trp Val Arg Gln Thr Pro Glu Lys Arg Leu Glu Trp
                165                 170                 175
Val Ala Thr Ile Ser Gly Gly Gly Arg Asp Thr Tyr Tyr Ser Asp Ser
                180                 185                 190
Val Lys Gly Arg Phe Thr Val Ser Arg Asp Asn Ala Lys Asn Asn Leu
            195                 200                 205
Phe Leu Gln Met Ser Ser Leu Arg Ser Glu Asp Thr Ala Leu Tyr Tyr
    210                 215                 220
Cys Ser Arg Gln Tyr Gly Thr Val Trp Phe Phe Asn Trp Gly Gln Gly
225                 230                 235                 240
Thr Leu Val Thr Val Ser Ala
                245

<210> SEQ ID NO 35
<211> LENGTH: 18
<212> TYPE: PRT
<213> ORGANISM: Mus musculus

<400> SEQUENCE: 35

Ser Ser Gly Gly Gly Gly Ser Gly Gly Gly Gly Ser Ser Arg
1               5                   10                  15

Ser Ser

<210> SEQ ID NO 36
<211> LENGTH: 5
<212> TYPE: PRT
<213> ORGANISM: Homo sapiens

<400> SEQUENCE: 36

Ser Glu Ser Phe Val
1               5

<210> SEQ ID NO 37
<211> LENGTH: 12
<212> TYPE: PRT
<213> ORGANISM: Homo sapiens

<400> SEQUENCE: 37

Lys Leu Ala Ala Phe Pro Glu Asp Arg Ser Gln Pro
1               5                   10
```

```
<210> SEQ ID NO 38
<211> LENGTH: 7
<212> TYPE: PRT
<213> ORGANISM: Homo sapiens

<400> SEQUENCE: 38

Leu Ala Pro Lys Ala Gln Ile
1               5
```